(12) United States Patent
Nam et al.

(10) Patent No.: US 10,604,572 B2
(45) Date of Patent: *Mar. 31, 2020

(54) ANTIBODY TO HUMAN AND MOUSE SEMA3A AND USE THEREOF

(71) Applicants: SAMSUNG LIFE PUBLIC WELFARE FOUNDATION, Seoul (KR); PANGEN BIOTECH INC., Gyeonggi-Do (KR)

(72) Inventors: Do Hyun Nam, Seoul (KR); Yong Jae Shin, Gyeonggi-do (KR); Jae Hyun Lee, Gyeonggi-Do (KR)

(73) Assignees: SAMSUNG LIFE PUBLIC WELFARE FOUNDATION, Seoul (KR); PANGEN BIOTECH INC., Gyeonggi-Do (KR)

( * ) Notice: Subject to any disclaimer, the term of this patent is extended or adjusted under 35 U.S.C. 154(b) by 112 days.

This patent is subject to a terminal disclaimer.

(21) Appl. No.: 15/964,648

(22) Filed: Apr. 27, 2018

(65) Prior Publication Data
US 2018/0244776 A1    Aug. 30, 2018

Related U.S. Application Data

(63) Continuation of application No. 15/771,488, filed as application No. PCT/KR2016/012072 on Oct. 26, 2016.

(30) Foreign Application Priority Data

Oct. 27, 2015    (KR) .................. 10-2015-0149272
Sep. 26, 2016    (KR) .................. 10-2016-0123233

(51) Int. Cl.
| | | |
|---|---|---|
| *A61K 39/395* | (2006.01) | |
| *C07K 16/28* | (2006.01) | |
| *A61P 35/00* | (2006.01) | |
| *A61P 35/04* | (2006.01) | |
| *A61K 39/00* | (2006.01) | |

(52) U.S. Cl.
CPC .......... *C07K 16/2803* (2013.01); *A61P 35/00* (2018.01); *A61P 35/04* (2018.01); *A61K 2039/505* (2013.01); *C07K 2317/33* (2013.01); *C07K 2317/56* (2013.01); *C07K 2317/565* (2013.01); *C07K 2317/567* (2013.01); *C07K 2317/622* (2013.01); *C07K 2317/73* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | | |
|---|---|---|---|---|
| 6,623,738 B1 * | 9/2003 | Tessier-Lavigne | ......................... | C07K 14/7056 424/139.1 |
| 7,888,066 B2 * | 2/2011 | Good | ................. | C07K 16/44 435/69.1 |
| 10,139,412 B2 * | 11/2018 | Vadasz | ............. | G01N 33/57434 |
| 2014/0349311 A1 | 11/2014 | Kumanogoh | | |

FOREIGN PATENT DOCUMENTS

| | | |
|---|---|---|
| EP | 2955195 A1 | 12/2015 |
| WO | WO-03/007803 A2 | 1/2003 |
| WO | WO-2011/055550 A1 | 5/2011 |
| WO | WO-2011/066284 A1 | 6/2011 |
| WO | WO-2014/123186 A1 | 8/2014 |
| WO | WO-2014/127479 A1 | 8/2014 |
| WO | WO-2015/083156 A1 | 6/2015 |

OTHER PUBLICATIONS

Yamashita et al (International Immunology, 2015, 27:459-466, available Apr. 7, 2015).*
1st Examination Report from corresponding Australian Patent Application No. 2016346595, dated Mar. 31, 2019.
Office Action from corresponding Japanese Patent Applicatin No. 2018-542072, dated May 21, 2019.
Shen, W., et al.; "Breast cancer cells promote osteoblastic differentiation via Sema 3A signaling pathway in vitro", Int J Clin Exp Pathol 2015;8(2):1584-1593.

(Continued)

*Primary Examiner* — Laura B Goddard
(74) *Attorney, Agent, or Firm* — Harness, Dickey & Pierce, P.L.C.

(57) ABSTRACT

The present invention provides an antibody having cross-linking ability against human Sema3A and mouse Sema3A. The antibody of the present invention can be used as therapeutic antibody drugs for inhibiting Sema3A in various cancers in which Sema3A expression is high, such as glioblastoma, pancreatic cancer and liver cancer. Since Sema3A is considered to be a therapeutic target of diabetic retinopathy, autoimmune arthritis, neuropathic pain and osteoporosis, the antibody of the present invention or an antigen binding fragment thereof can be used as a therapeutic agent for associated diseases in addition to an anti-cancer drug. The antibody of the present invention inhibits the growth of cancer cells derived from various carcinomas through inhibition of Sema3A function due to high anti-Sema3A binding, and inhibits the movement of cancer cells through inhibition of phosphorylation of ERK among Sema3A lower signaling substances.

6 Claims, 30 Drawing Sheets

Specification includes a Sequence Listing.

(56) References Cited

OTHER PUBLICATIONS

Maione, F.; et al.; "Semaphorin 3A overcomes cancer hypoxia and metastatic dissemination induced by antiangiogenic treatment in mice", The Journal of Clinical Investigation, vol. 122, No. 5, May 2012, pp. 1832-1848.
International Search Report from corresponding PCT Application No. PCT/KR2016/012072 dated Feb. 8, 2017 and it's English translation.
Shirvan, A., et al.; "Anti Sema3A antibodies rescue retinal ganglion cells from cell death following optic nerve axotomy", Journal of Biological Chemistry, American Society for Biochemistry and Molecular Biology, vol. 277, No. 51, Dec. 20, 2002, pp. 49799-49807.
Extended European Search Report from corresponding European Patent Application No. 16860196.1, dated Jul. 23, 2019.
Voskoglou-Nomikos (Clin. Can. Res. 9:4227-4239(2003)).
Dennis (Nature 442:739-741(2006)).
Cespdes et al. (Clin. Transl. Oncol. 8(5):318-329(2006)).
Talmadge et al. (Am. J. Pathol 170(3):793-804(2007)).
Fujimori et al (J. Nuc. Med. 31:1191-1198(1990)).
Beckman et al. (Can. 109:170-179(2007)).
Thurber et al. (Adv. Drug Deliv. Rev. 60:1421-1434(2008)).
Rudnick et al (Can. Biotherp. & Radiopharm. 24: 155-162(2009)).
Huang et al. (Appl Microbiol Biotechnol(2010)87:401-410).
Lee et al. (Anticancer Res. 38(5):2803-2810;May 2018).
Lee et al. (Cancer Res Treat. 50(3): 1009-1022;Jul. 2018).
Office Action from corresponding U.S. Appl. No. 15/771,488 dated Nov. 21, 2019.

\* cited by examiner

SEQUENCE LISTING

```
<160> NUMBER OF SEQ ID NOS: 110

<210> SEQ ID NO 1
<211> LENGTH: 8
<212> TYPE: PRT
<213> ORGANISM: Artificial Sequence
<220> FEATURE:
<223> OTHER INFORMATION: A08 heavy chain CDR1

<400> SEQUENCE: 1

Gly Phe Thr Phe Ser Asp Tyr Ala
1               5

<210> SEQ ID NO 2
```

```
<211> LENGTH: 8
<212> TYPE: PRT
<213> ORGANISM: Artificial Sequence
<220> FEATURE:
<223> OTHER INFORMATION: A08 heavy chain CDR2

<400> SEQUENCE: 2

Ile Tyr Tyr Asp Asp Ser Ser Gln
1               5

<210> SEQ ID NO 3
<211> LENGTH: 9
<212> TYPE: PRT
<213> ORGANISM: Artificial Sequence
<220> FEATURE:
<223> OTHER INFORMATION: A08 heavy chain CDR3

<400> SEQUENCE: 3

Ala Lys Asn Leu Gly Arg Phe Asp Tyr
1               5

<210> SEQ ID NO 4
<211> LENGTH: 8
<212> TYPE: PRT
<213> ORGANISM: Artificial Sequence
<220> FEATURE:
<223> OTHER INFORMATION: A08 light chain CDR1

<400> SEQUENCE: 4

Ser Ser Asn Ile Gly Ser Asn Ala
1               5

<210> SEQ ID NO 5
<211> LENGTH: 3
<212> TYPE: PRT
<213> ORGANISM: Artificial Sequence
<220> FEATURE:
<223> OTHER INFORMATION: A08 light chain CDR2

<400> SEQUENCE: 5

Asp Asp Asn
1

<210> SEQ ID NO 6
<211> LENGTH: 11
<212> TYPE: PRT
<213> ORGANISM: Artificial Sequence
<220> FEATURE:
<223> OTHER INFORMATION: A08 light chain CDR3

<400> SEQUENCE: 6

Gly Ala Trp Asp Asp Ser Leu Ser Ala Tyr Val
1               5                   10

<210> SEQ ID NO 7
<211> LENGTH: 8
<212> TYPE: PRT
<213> ORGANISM: Artificial Sequence
<220> FEATURE:
<223> OTHER INFORMATION: C10 heavy chain CDR1

<400> SEQUENCE: 7

Gly Phe Thr Phe Ser Asp Tyr Ala
1               5

<210> SEQ ID NO 8
<211> LENGTH: 8
```

```
<212> TYPE: PRT
<213> ORGANISM: Artificial Sequence
<220> FEATURE:
<223> OTHER INFORMATION: C10 heavy chain CDR2

<400> SEQUENCE: 8

Ile Tyr Tyr Asp Asp Ser Ser Gln
1               5

<210> SEQ ID NO 9
<211> LENGTH: 9
<212> TYPE: PRT
<213> ORGANISM: Artificial Sequence
<220> FEATURE:
<223> OTHER INFORMATION: C10 heavy chain CDR3

<400> SEQUENCE: 9

Ala Arg Tyr Leu Gly Leu Phe Asp Tyr
1               5

<210> SEQ ID NO 10
<211> LENGTH: 8
<212> TYPE: PRT
<213> ORGANISM: Artificial Sequence
<220> FEATURE:
<223> OTHER INFORMATION: C10 light chain CDR1

<400> SEQUENCE: 10

Ser Ser Asn Ile Gly Asn Asn Ser
1               5

<210> SEQ ID NO 11
<211> LENGTH: 3
<212> TYPE: PRT
<213> ORGANISM: Artificial Sequence
<220> FEATURE:
<223> OTHER INFORMATION: C10 light chain CDR2

<400> SEQUENCE: 11

Ser Asp Ser
1

<210> SEQ ID NO 12
<211> LENGTH: 11
<212> TYPE: PRT
<213> ORGANISM: Artificial Sequence
<220> FEATURE:
<223> OTHER INFORMATION: C10 light chain CDR3

<400> SEQUENCE: 12

Gly Ser Trp Asp Tyr Ser Leu Ser Ala Tyr Val
1               5                   10

<210> SEQ ID NO 13
<211> LENGTH: 8
<212> TYPE: PRT
<213> ORGANISM: Artificial Sequence
<220> FEATURE:
<223> OTHER INFORMATION: F11 heavy chain CDR1

<400> SEQUENCE: 13

Gly Phe Thr Phe Ser Asp Tyr Ala
1               5

<210> SEQ ID NO 14
<211> LENGTH: 8
<212> TYPE: PRT
```

-continued

<213> ORGANISM: Artificial Sequence
<220> FEATURE:
<223> OTHER INFORMATION: F11 heavy chain CDR2

<400> SEQUENCE: 14

Ile Tyr Tyr Asp Ser Gly Ser Lys
1               5

<210> SEQ ID NO 15
<211> LENGTH: 9
<212> TYPE: PRT
<213> ORGANISM: Artificial Sequence
<220> FEATURE:
<223> OTHER INFORMATION: F11 heavy chain CDR3

<400> SEQUENCE: 15

Ala Lys Leu Asn Gly Asp Phe Asp Tyr
1               5

<210> SEQ ID NO 16
<211> LENGTH: 8
<212> TYPE: PRT
<213> ORGANISM: Artificial Sequence
<220> FEATURE:
<223> OTHER INFORMATION: F11 light chain CDR1

<400> SEQUENCE: 16

Ser Ser Asn Ile Gly Asn Asn Asp
1               5

<210> SEQ ID NO 17
<211> LENGTH: 3
<212> TYPE: PRT
<213> ORGANISM: Artificial Sequence
<220> FEATURE:
<223> OTHER INFORMATION: F11 light chain CDR2

<400> SEQUENCE: 17

Ala Asp Ser
1

<210> SEQ ID NO 18
<211> LENGTH: 11
<212> TYPE: PRT
<213> ORGANISM: Artificial Sequence
<220> FEATURE:
<223> OTHER INFORMATION: F11 light chain CDR3

<400> SEQUENCE: 18

Gly Ala Trp Asp Ser Ser Leu Ser Gly Tyr Val
1               5                   10

<210> SEQ ID NO 19
<211> LENGTH: 116
<212> TYPE: PRT
<213> ORGANISM: Artificial Sequence
<220> FEATURE:
<223> OTHER INFORMATION: Heavy chain variable region of synthetic A08
      scFv A/a

<400> SEQUENCE: 19

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Ala Met Ser Trp Val Arg Gln Ala Pro Gly Lys Gly Leu Glu Trp Val

```
                35                  40                  45
Ser Gly Ile Tyr Tyr Asp Asp Ser Ser Gln Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asn Leu Gly Arg Phe Asp Tyr Trp Gly Gln Gly Thr Leu Val
            100                 105                 110

Thr Val Ser Ser
            115

<210> SEQ ID NO 20
<211> LENGTH: 110
<212> TYPE: PRT
<213> ORGANISM: Artificial Sequence
<220> FEATURE:
<223> OTHER INFORMATION: Light chain variable region of synthetic A08
      scFv A/a

<400> SEQUENCE: 20

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ser Asn
            20                  25                  30

Ala Val Thr Trp Tyr Gln Gln Leu Pro Gly Thr Ala Pro Lys Leu Leu
        35                  40                  45

Ile Tyr Asp Asp Asn His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ala Trp Asp Asp Ser Leu
                85                  90                  95

Ser Ala Tyr Val Phe Gly Gly Gly Thr Lys Leu Thr Val Leu
            100                 105                 110

<210> SEQ ID NO 21
<211> LENGTH: 116
<212> TYPE: PRT
<213> ORGANISM: Artificial Sequence
<220> FEATURE:
<223> OTHER INFORMATION: Heavy chain variable region of synthetic C10
      scFv A/a

<400> SEQUENCE: 21

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Ala Met Ser Trp Val Arg Gln Ala Pro Gly Lys Gly Leu Glu Trp Val
        35                  40                  45

Ser Gly Ile Tyr Tyr Asp Asp Ser Ser Gln Tyr Tyr Ala Asp Ser Val
    50                  55                  60

Glu Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Leu Gly Leu Phe Asp Tyr Trp Gly Gln Gly Thr Leu Val
```

```
                     100                 105                 110
Thr Val Ser Ser
        115

<210> SEQ ID NO 22
<211> LENGTH: 110
<212> TYPE: PRT
<213> ORGANISM: Artificial Sequence
<220> FEATURE:
<223> OTHER INFORMATION: Light chain variable region of synthetic C10
      scFv A/a

<400> SEQUENCE: 22

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Asn Asn
            20                  25                  30

Ser Val Asn Trp Tyr Gln Gln Leu Pro Gly Thr Ala Pro Lys Leu Leu
        35                  40                  45

Ile Tyr Ser Asp Ser Gln Arg Pro Ser Gly Val Pro Asp Arg Phe Ser
50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ser Trp Asp Tyr Ser Leu
                85                  90                  95

Ser Ala Tyr Val Phe Gly Gly Gly Thr Lys Leu Thr Val Leu
            100                 105                 110

<210> SEQ ID NO 23
<211> LENGTH: 116
<212> TYPE: PRT
<213> ORGANISM: Artificial Sequence
<220> FEATURE:
<223> OTHER INFORMATION: Heavy chain variable region of synthetic F11
      scFv A/a

<400> SEQUENCE: 23

Glu Val Gln Leu Leu Glu Ser Gly Gly Gly Leu Val Gln Thr Gly Gly
1               5                   10                  15

Ser Leu Arg Leu Ser Cys Ala Ala Ser Gly Phe Thr Phe Ser Asp Tyr
            20                  25                  30

Ala Met Ser Trp Val Arg Gln Ala Pro Gly Lys Gly Leu Glu Trp Val
        35                  40                  45

Ser Trp Ile Tyr Tyr Asp Ser Gly Ser Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Leu Asn Gly Asp Phe Asp Tyr Trp Gly Gln Gly Thr Leu Val
            100                 105                 110

Thr Val Ser Ser
        115

<210> SEQ ID NO 24
<211> LENGTH: 110
<212> TYPE: PRT
<213> ORGANISM: Artificial Sequence
<220> FEATURE:
<223> OTHER INFORMATION: Light chain variable region of synthetic F11
``` scFv A/a

<400> SEQUENCE: 24

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Asn Asn
            20                  25                  30

Asp Val Ser Trp Tyr Gln Gln Leu Pro Gly Thr Ala Pro Lys Leu Leu
        35                  40                  45

Ile Tyr Ala Asp Ser His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ala Trp Asp Ser Ser Leu
                85                  90                  95

Ser Gly Tyr Val Phe Gly Gly Gly Thr Lys Leu Thr Val Leu
            100                 105                 110

<210> SEQ ID NO 25
<211> LENGTH: 25
<212> TYPE: PRT
<213> ORGANISM: Artificial Sequence
<220> FEATURE:
<223> OTHER INFORMATION: A08 heavy chain FR1

<400> SEQUENCE: 25

Glu Val Gln Leu Leu Glu Ser Gly Gly Gly Leu Val Gln Pro Gly Gly
1               5                   10                  15

Ser Leu Arg Leu Ser Cys Ala Ala Ser
            20                  25

<210> SEQ ID NO 26
<211> LENGTH: 17
<212> TYPE: PRT
<213> ORGANISM: Artificial Sequence
<220> FEATURE:
<223> OTHER INFORMATION: A08 heavy chain FR2

<400> SEQUENCE: 26

Met Ser Trp Val Arg Gln Ala Pro Gly Lys Gly Leu Glu Trp Val Ser
1               5                   10                  15

Gly

<210> SEQ ID NO 27
<211> LENGTH: 38
<212> TYPE: PRT
<213> ORGANISM: Artificial Sequence
<220> FEATURE:
<223> OTHER INFORMATION: A08 heavy chain FR3

<400> SEQUENCE: 27

Tyr Tyr Ala Asp Ser Val Lys Gly Arg Phe Thr Ile Ser Arg Asp Asn
1               5                   10                  15

Ser Lys Asn Thr Leu Tyr Leu Gln Met Asn Ser Leu Arg Ala Glu Asp
            20                  25                  30

Thr Ala Val Tyr Tyr Cys
            35

<210> SEQ ID NO 28
<211> LENGTH: 11
<212> TYPE: PRT

<213> ORGANISM: Artificial Sequence
<220> FEATURE:
<223> OTHER INFORMATION: A08 heavy chain FR4

<400> SEQUENCE: 28

Trp Gly Gln Gly Thr Leu Val Thr Val Ser Ser
1               5                   10

<210> SEQ ID NO 29
<211> LENGTH: 25
<212> TYPE: PRT
<213> ORGANISM: Artificial Sequence
<220> FEATURE:
<223> OTHER INFORMATION: C10 heavy chain FR1

<400> SEQUENCE: 29

Glu Val Gln Leu Leu Glu Ser Gly Gly Leu Val Gln Pro Gly Gly
1               5                   10                  15

Ser Leu Arg Leu Ser Cys Ala Ala Ser
            20                  25

<210> SEQ ID NO 30
<211> LENGTH: 17
<212> TYPE: PRT
<213> ORGANISM: Artificial Sequence
<220> FEATURE:
<223> OTHER INFORMATION: C10 heavy chain FR2

<400> SEQUENCE: 30

Met Ser Trp Val Arg Gln Ala Pro Gly Lys Gly Leu Glu Trp Val Ser
1               5                   10                  15

Gly

<210> SEQ ID NO 31
<211> LENGTH: 38
<212> TYPE: PRT
<213> ORGANISM: Artificial Sequence
<220> FEATURE:
<223> OTHER INFORMATION: C10 heavy chain FR3

<400> SEQUENCE: 31

Tyr Tyr Ala Asp Ser Val Glu Gly Arg Phe Thr Ile Ser Arg Asp Asn
1               5                   10                  15

Ser Lys Asn Thr Leu Tyr Leu Gln Met Asn Ser Leu Arg Ala Glu Asp
            20                  25                  30

Thr Ala Val Tyr Tyr Cys
        35

<210> SEQ ID NO 32
<211> LENGTH: 11
<212> TYPE: PRT
<213> ORGANISM: Artificial Sequence
<220> FEATURE:
<223> OTHER INFORMATION: C10 heavy chain FR4

<400> SEQUENCE: 32

Trp Gly Gln Gly Thr Leu Val Thr Val Ser Ser
1               5                   10

<210> SEQ ID NO 33
<211> LENGTH: 25
<212> TYPE: PRT
<213> ORGANISM: Artificial Sequence
<220> FEATURE:
<223> OTHER INFORMATION: F11 heavy chain FR1

<400> SEQUENCE: 33

Glu Val Gln Leu Leu Glu Ser Gly Gly Gly Leu Val Gln Thr Gly Gly
1               5                   10                  15

Ser Leu Arg Leu Ser Cys Ala Ala Ser
            20                  25

<210> SEQ ID NO 34
<211> LENGTH: 17
<212> TYPE: PRT
<213> ORGANISM: Artificial Sequence
<220> FEATURE:
<223> OTHER INFORMATION: F11 heavy chain FR2

<400> SEQUENCE: 34

Met Ser Trp Val Arg Gln Ala Pro Gly Lys Gly Leu Glu Trp Val Ser
1               5                   10                  15

Trp

<210> SEQ ID NO 35
<211> LENGTH: 38
<212> TYPE: PRT
<213> ORGANISM: Artificial Sequence
<220> FEATURE:
<223> OTHER INFORMATION: F11 heavy chain FR3

<400> SEQUENCE: 35

Tyr Tyr Ala Asp Ser Val Lys Gly Arg Phe Thr Ile Ser Arg Asp Asn
1               5                   10                  15

Ser Lys Asn Thr Leu Tyr Leu Gln Met Asn Ser Leu Arg Ala Glu Asp
            20                  25                  30

Thr Ala Val Tyr Tyr Cys
        35

<210> SEQ ID NO 36
<211> LENGTH: 11
<212> TYPE: PRT
<213> ORGANISM: Artificial Sequence
<220> FEATURE:
<223> OTHER INFORMATION: F11 heavy chain FR4

<400> SEQUENCE: 36

Trp Gly Gln Gly Thr Leu Val Thr Val Ser Ser
1               5                   10

<210> SEQ ID NO 37
<211> LENGTH: 25
<212> TYPE: PRT
<213> ORGANISM: Artificial Sequence
<220> FEATURE:
<223> OTHER INFORMATION: A08 light chain FR1

<400> SEQUENCE: 37

Gln Ser Val Leu Thr Gln Pro Pro Ser Ala Ser Gly Thr Pro Gly Gln
1               5                   10                  15

Arg Val Thr Ile Ser Cys Thr Gly Ser
            20                  25

<210> SEQ ID NO 38
<211> LENGTH: 17
<212> TYPE: PRT
<213> ORGANISM: Artificial Sequence
<220> FEATURE:
<223> OTHER INFORMATION: A08 light chain FR2

<400> SEQUENCE: 38

Val Thr Trp Tyr Gln Gln Leu Pro Gly Thr Ala Pro Lys Leu Leu Ile
1               5                   10                  15

Tyr

<210> SEQ ID NO 39
<211> LENGTH: 36
<212> TYPE: PRT
<213> ORGANISM: Artificial Sequence
<220> FEATURE:
<223> OTHER INFORMATION: A08 light chain FR3

<400> SEQUENCE: 39

His Arg Pro Ser Gly Val Pro Asp Arg Phe Ser Gly Ser Lys Ser Gly
1               5                   10                  15

Thr Ser Ala Ser Leu Ala Ile Ser Gly Leu Arg Ser Glu Asp Glu Ala
            20                  25                  30

Asp Tyr Tyr Cys
        35

<210> SEQ ID NO 40
<211> LENGTH: 10
<212> TYPE: PRT
<213> ORGANISM: Artificial Sequence
<220> FEATURE:
<223> OTHER INFORMATION: A08 light chain FR4

<400> SEQUENCE: 40

Phe Gly Gly Gly Thr Lys Leu Thr Val Leu
1               5                   10

<210> SEQ ID NO 41
<211> LENGTH: 25
<212> TYPE: PRT
<213> ORGANISM: Artificial Sequence
<220> FEATURE:
<223> OTHER INFORMATION: C10 light chain FR1

<400> SEQUENCE: 41

Gln Ser Val Leu Thr Gln Pro Pro Ser Ala Ser Gly Thr Pro Gly Gln
1               5                   10                  15

Arg Val Thr Ile Ser Cys Ser Gly Ser
            20                  25

<210> SEQ ID NO 42
<211> LENGTH: 17
<212> TYPE: PRT
<213> ORGANISM: Artificial Sequence
<220> FEATURE:
<223> OTHER INFORMATION: C10 light chain FR2

<400> SEQUENCE: 42

Val Asn Trp Tyr Gln Gln Leu Pro Gly Thr Ala Pro Lys Leu Leu Ile
1               5                   10                  15

Tyr

<210> SEQ ID NO 43
<211> LENGTH: 36
<212> TYPE: PRT
<213> ORGANISM: Artificial Sequence
<220> FEATURE:
<223> OTHER INFORMATION: C10 light chain FR3

```
<400> SEQUENCE: 43

Gln Arg Pro Ser Gly Val Pro Asp Arg Phe Ser Gly Ser Lys Ser Gly
1               5                   10                  15

Thr Ser Ala Ser Leu Ala Ile Ser Gly Leu Arg Ser Glu Asp Glu Ala
            20                  25                  30

Asp Tyr Tyr Cys
        35

<210> SEQ ID NO 44
<211> LENGTH: 10
<212> TYPE: PRT
<213> ORGANISM: Artificial Sequence
<220> FEATURE:
<223> OTHER INFORMATION: C10 light chain FR4

<400> SEQUENCE: 44

Phe Gly Gly Gly Thr Lys Leu Thr Val Leu
1               5                   10

<210> SEQ ID NO 45
<211> LENGTH: 25
<212> TYPE: PRT
<213> ORGANISM: Artificial Sequence
<220> FEATURE:
<223> OTHER INFORMATION: F11 light chain FR1

<400> SEQUENCE: 45

Gln Ser Val Leu Thr Gln Pro Pro Ser Ala Ser Gly Thr Pro Gly Gln
1               5                   10                  15

Arg Val Thr Ile Ser Cys Ser Gly Ser
            20                  25

<210> SEQ ID NO 46
<211> LENGTH: 17
<212> TYPE: PRT
<213> ORGANISM: Artificial Sequence
<220> FEATURE:
<223> OTHER INFORMATION: F11 light chain FR2

<400> SEQUENCE: 46

Val Ser Trp Tyr Gln Gln Leu Pro Gly Thr Ala Pro Lys Leu Leu Ile
1               5                   10                  15

Tyr

<210> SEQ ID NO 47
<211> LENGTH: 36
<212> TYPE: PRT
<213> ORGANISM: Artificial Sequence
<220> FEATURE:
<223> OTHER INFORMATION: F11 light chain FR3

<400> SEQUENCE: 47

His Arg Pro Ser Gly Val Pro Asp Arg Phe Ser Gly Ser Lys Ser Gly
1               5                   10                  15

Thr Ser Ala Ser Leu Ala Ile Ser Gly Leu Arg Ser Glu Asp Glu Ala
            20                  25                  30

Asp Tyr Tyr Cys
        35

<210> SEQ ID NO 48
<211> LENGTH: 10
<212> TYPE: PRT
<213> ORGANISM: Artificial Sequence
```

```
<220> FEATURE:
<223> OTHER INFORMATION: F11 light chain FR4

<400> SEQUENCE: 48

Phe Gly Gly Gly Thr Lys Leu Thr Val Leu
1               5                   10

<210> SEQ ID NO 49
<211> LENGTH: 135
<212> TYPE: PRT
<213> ORGANISM: Artificial Sequence
<220> FEATURE:
<223> OTHER INFORMATION: A08_OMPA.ab11 Heavy Chain

<400> SEQUENCE: 49

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
                20                  25                  30

Ala Met Glu Thr Ser Trp Val Arg Gln Ala Pro Gly Lys Gly Leu Glu
            35                  40                  45

Trp Val Ser Gly Ile Tyr Tyr Asp Asp Ser Ser Gln Tyr Tyr Ala Asp
        50                  55                  60

Ser Val Lys Gly Arg Phe Thr Ile Ser Arg Asp Asn Ser Lys Asn Thr
65                  70                  75                  80

Leu Tyr Leu Gln Met Glu Thr Asn Ser Leu Arg Ala Glu Asp Thr Ala
                85                  90                  95

Val Tyr Tyr Cys Ala Lys Asn Leu Gly Arg Phe Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser
        130                 135

<210> SEQ ID NO 50
<211> LENGTH: 135
<212> TYPE: PRT
<213> ORGANISM: Artificial Sequence
<220> FEATURE:
<223> OTHER INFORMATION: A03_opmA.ab11 Heavy Chain

<400> SEQUENCE: 50

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
                20                  25                  30

Ala Met Glu Thr Ser Trp Val Arg Gln Ala Pro Gly Lys Gly Leu Glu
            35                  40                  45

Trp Val Ser Gly Ile Tyr Tyr Asp Asp Ser Ser Gln Tyr Tyr Ala Asp
        50                  55                  60

Ser Val Lys Gly Arg Phe Thr Ile Ser Arg Asp Asn Ser Lys Asn Thr
65                  70                  75                  80

Leu Tyr Leu Gln Met Glu Thr Asn Ser Leu Arg Ala Glu Asp Thr Ala
                85                  90                  95

Val Tyr Tyr Cys Ala Lys Asn Leu Gly Arg Phe Asp Tyr Trp Gly Gln
            100                 105                 110

Gly Thr Leu Val Thr Val Ser Ser Gly Gly Gly Gly Ser Gly Gly Gly
        115                 120                 125
```

```
Gly Ser Gly Gly Gly Gly Ser
    130                 135

<210> SEQ ID NO 51
<211> LENGTH: 135
<212> TYPE: PRT
<213> ORGANISM: Artificial Sequence
<220> FEATURE:
<223> OTHER INFORMATION: C04_opmA.ab11 Heavy Chain

<400> SEQUENCE: 51

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Ala Met Glu Thr Ser Trp Val Arg Gln Ala Pro Gly Lys Gly Leu Glu
        35                  40                  45

Trp Val Ser Gly Ile Tyr Tyr Asp Asp Ser Ser Gln Tyr Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Met Glu Thr Asn Ser Leu Arg Ala Glu Asp Thr Ala
                85                  90                  95

Val Tyr Tyr Cys Ala Lys Asn Leu Gly Arg Phe Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser
    130                 135

<210> SEQ ID NO 52
<211> LENGTH: 135
<212> TYPE: PRT
<213> ORGANISM: Artificial Sequence
<220> FEATURE:
<223> OTHER INFORMATION: F06_opmA.ab11 Heavy Chain

<400> SEQUENCE: 52

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Ala Met Glu Thr Ser Trp Val Arg Gln Ala Pro Gly Lys Gly Leu Glu
        35                  40                  45

Trp Val Ser Gly Ile Tyr Tyr Asp Asp Ser Ser Gln Tyr Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Met Glu Thr Asn Ser Leu Arg Ala Glu Asp Thr Ala
                85                  90                  95

Val Tyr Tyr Cys Ala Lys Asn Leu Gly Arg Phe Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser
    130                 135

<210> SEQ ID NO 53
```

```
<211> LENGTH: 135
<212> TYPE: PRT
<213> ORGANISM: Artificial Sequence
<220> FEATURE:
<223> OTHER INFORMATION: B05_opmA.ab11 Heavy Chain

<400> SEQUENCE: 53

Glu Val Gln Leu Leu Glu Ser Gly Gly Gly Leu Val Gln Thr Gly Gly
1               5                   10                  15

Ser Leu Arg Leu Ser Cys Ala Ala Ser Gly Phe Thr Phe Ser Asp Tyr
            20                  25                  30

Ala Met Glu Thr Ser Trp Val Arg Gln Ala Pro Gly Lys Gly Leu Glu
        35                  40                  45

Trp Val Ser Trp Ile Tyr Tyr Asp Ser Gly Ser Lys Tyr Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Met Glu Thr Asn Ser Leu Arg Ala Glu Asp Thr Ala
                85                  90                  95

Val Tyr Tyr Cys Ala Lys Leu Asn Gly Asp Phe Asp Tyr Trp Gly Gln
            100                 105                 110

Gly Thr Leu Val Thr Val Ser Ser Gly Gly Gly Ser Gly Gly Gly
        115                 120                 125

Gly Ser Gly Gly Gly Gly Ser
    130                 135

<210> SEQ ID NO 54
<211> LENGTH: 135
<212> TYPE: PRT
<213> ORGANISM: Artificial Sequence
<220> FEATURE:
<223> OTHER INFORMATION: F03_opmA.ab11 Heavy Chain

<400> SEQUENCE: 54

Glu Val Gln Leu Leu Glu Ser Gly Gly Gly Leu Val Gln Thr Gly Gly
1               5                   10                  15

Ser Leu Arg Leu Ser Cys Ala Ala Ser Gly Phe Thr Phe Ser Asp Tyr
            20                  25                  30

Ala Met Glu Thr Ser Trp Val Arg Gln Ala Pro Gly Lys Gly Leu Glu
        35                  40                  45

Trp Val Ser Trp Ile Tyr Tyr Asp Ser Gly Ser Lys Tyr Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Met Glu Thr Asn Ser Leu Arg Ala Glu Asp Thr Ala
                85                  90                  95

Val Tyr Tyr Cys Ala Lys Leu Asn Gly Asp Phe Asp Tyr Trp Gly Gln
            100                 105                 110

Gly Thr Leu Val Thr Val Ser Ser Gly Gly Gly Ser Gly Gly Gly
        115                 120                 125

Gly Ser Gly Gly Gly Gly Ser
    130                 135

<210> SEQ ID NO 55
<211> LENGTH: 135
<212> TYPE: PRT
<213> ORGANISM: Artificial Sequence
<220> FEATURE:
<223> OTHER INFORMATION: B04_opmA.ab11 Heavy Chain
```

<400> SEQUENCE: 55

Glu Val Gln Leu Leu Glu Ser Gly Gly Gly Leu Val Gln Thr Gly Gly
1               5                   10                  15

Ser Leu Arg Leu Ser Cys Ala Ala Ser Gly Phe Thr Phe Ser Asp Tyr
            20                  25                  30

Ala Met Glu Thr Ser Trp Val Arg Gln Ala Pro Gly Lys Gly Leu Glu
        35                  40                  45

Trp Val Ser Trp Ile Tyr Tyr Asp Ser Gly Ser Lys Tyr Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Met Glu Thr Asn Ser Leu Arg Ala Glu Asp Thr Ala
                85                  90                  95

Val Tyr Tyr Cys Ala Lys Leu Asn Gly Asp Phe Asp Tyr Trp Gly Gln
            100                 105                 110

Gly Thr Leu Val Thr Val Ser Ser Gly Gly Gly Ser Gly Gly Gly
        115                 120                 125

Gly Ser Gly Gly Gly Gly Ser
    130                 135

<210> SEQ ID NO 56
<211> LENGTH: 135
<212> TYPE: PRT
<213> ORGANISM: Artificial Sequence
<220> FEATURE:
<223> OTHER INFORMATION: A06_opmA.ab11 Heavy Chain

<400> SEQUENCE: 56

Glu Val Gln Leu Leu Glu Ser Gly Gly Gly Leu Val Gln Thr Gly Gly
1               5                   10                  15

Ser Leu Arg Leu Ser Cys Ala Ala Ser Gly Phe Thr Phe Ser Asp Tyr
            20                  25                  30

Ala Met Glu Thr Ser Trp Val Arg Gln Ala Pro Gly Lys Gly Leu Glu
        35                  40                  45

Trp Val Ser Trp Ile Tyr Tyr Asp Ser Gly Ser Lys Tyr Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Met Glu Thr Asn Ser Leu Arg Ala Glu Asp Thr Ala
                85                  90                  95

Val Tyr Tyr Cys Ala Lys Leu Asn Gly Asp Phe Asp Tyr Trp Gly Gln
            100                 105                 110

Gly Thr Leu Val Thr Val Ser Ser Gly Gly Gly Ser Gly Gly Gly
        115                 120                 125

Gly Ser Gly Gly Gly Gly Ser
    130                 135

<210> SEQ ID NO 57
<211> LENGTH: 135
<212> TYPE: PRT
<213> ORGANISM: Artificial Sequence
<220> FEATURE:
<223> OTHER INFORMATION: B02_opmA.ab19 Heavy Chain

<400> SEQUENCE: 57

Glu Val Gln Leu Leu Glu Ser Gly Gly Gly Leu Val Gln Thr Gly Gly
1               5                   10                  15

Ser Leu Arg Leu Ser Cys Ala Ala Ser Gly Phe Thr Phe Ser Asp Tyr
                20                  25                  30

Ala Met Glu Thr Ser Trp Val Arg Gln Ala Pro Gly Lys Gly Leu Glu
            35                  40                  45

Trp Val Ser Trp Ile Tyr Tyr Asp Ser Gly Ser Lys Tyr Tyr Ala Asp
 50                  55                  60

Ser Val Lys Gly Arg Phe Thr Ile Ser Arg Asp Asn Ser Lys Asn Thr
65                  70                  75                  80

Leu Tyr Leu Gln Met Glu Thr Asn Ser Leu Arg Ala Glu Asp Thr Ala
                85                  90                  95

Val Tyr Tyr Cys Ala Lys Leu Asn Gly Asp Phe Asp Tyr Trp Gly Gln
                100                 105                 110

Gly Thr Leu Val Thr Val Ser Ser Gly Gly Gly Ser Gly Gly Gly
            115                 120                 125

Gly Ser Gly Gly Gly Gly Ser
        130                 135

<210> SEQ ID NO 58
<211> LENGTH: 135
<212> TYPE: PRT
<213> ORGANISM: Artificial Sequence
<220> FEATURE:
<223> OTHER INFORMATION: E09_OMPA.ab11 Heavy Chain

<400> SEQUENCE: 58

Glu Val Gln Leu Leu Glu Ser Gly Gly Gly Leu Val Gln Thr Gly Gly
1               5                   10                  15

Ser Leu Arg Leu Ser Cys Ala Ala Ser Gly Phe Thr Phe Ser Asp Tyr
                20                  25                  30

Ala Met Glu Thr Ser Trp Val Arg Gln Ala Pro Gly Lys Gly Leu Glu
            35                  40                  45

Trp Val Ser Trp Ile Tyr Tyr Asp Ser Gly Ser Lys Tyr Tyr Ala Asp
 50                  55                  60

Ser Val Lys Gly Arg Phe Thr Ile Ser Arg Asp Asn Ser Lys Asn Thr
65                  70                  75                  80

Leu Tyr Leu Gln Met Glu Thr Asn Ser Leu Arg Ala Glu Asp Thr Ala
                85                  90                  95

Val Tyr Tyr Cys Ala Lys Leu Asn Gly Asp Phe Asp Tyr Trp Gly Gln
                100                 105                 110

Gly Thr Leu Val Thr Val Ser Ser Gly Gly Gly Ser Gly Gly Gly
            115                 120                 125

Gly Ser Gly Gly Gly Gly Ser
        130                 135

<210> SEQ ID NO 59
<211> LENGTH: 135
<212> TYPE: PRT
<213> ORGANISM: Artificial Sequence
<220> FEATURE:
<223> OTHER INFORMATION: E11_OMPA.ab11 Heavy Chain

<400> SEQUENCE: 59

Glu Val Gln Leu Leu Glu Ser Gly Gly Gly Leu Val Gln Thr Gly Gly
1               5                   10                  15

Ser Leu Arg Leu Ser Cys Ala Ala Ser Gly Phe Thr Phe Ser Asp Tyr
                20                  25                  30

Ala Met Glu Thr Ser Trp Val Arg Gln Ala Pro Gly Lys Gly Leu Glu

```
                35                  40                  45
Trp Val Ser Trp Ile Tyr Tyr Asp Ser Gly Ser Lys Tyr Tyr Ala Asp
 50                  55                  60

Ser Val Lys Gly Arg Phe Thr Ile Ser Arg Asp Asn Ser Lys Asn Thr
 65                  70                  75                  80

Leu Tyr Leu Gln Met Glu Thr Asn Ser Leu Arg Ala Glu Asp Thr Ala
                 85                  90                  95

Val Tyr Tyr Cys Ala Lys Leu Asn Gly Asp Phe Asp Tyr Trp Gly Gln
            100                 105                 110

Gly Thr Leu Val Thr Val Ser Ser Gly Gly Gly Gly Ser Gly Gly Gly
            115                 120                 125

Gly Ser Gly Gly Gly Gly Ser
            130                 135

<210> SEQ ID NO 60
<211> LENGTH: 135
<212> TYPE: PRT
<213> ORGANISM: Artificial Sequence
<220> FEATURE:
<223> OTHER INFORMATION: E12_OMPA.ab11 Heavy Chain

<400> SEQUENCE: 60

Glu Val Gln Leu Leu Glu Ser Gly Gly Gly Leu Val Gln Thr Gly Gly
  1               5                  10                  15

Ser Leu Arg Leu Ser Cys Ala Ala Ser Gly Phe Thr Phe Ser Asp Tyr
                 20                  25                  30

Ala Met Glu Thr Ser Trp Val Arg Gln Ala Pro Gly Lys Gly Leu Glu
             35                  40                  45

Trp Val Ser Trp Ile Tyr Tyr Asp Ser Gly Ser Lys Tyr Tyr Ala Asp
 50                  55                  60

Ser Val Lys Gly Arg Phe Thr Ile Ser Arg Asp Asn Ser Lys Asn Thr
 65                  70                  75                  80

Leu Tyr Leu Gln Met Glu Thr Asn Ser Leu Arg Ala Glu Asp Thr Ala
                 85                  90                  95

Val Tyr Tyr Cys Ala Lys Leu Asn Gly Asp Phe Asp Tyr Trp Gly Gln
            100                 105                 110

Gly Thr Leu Val Thr Val Ser Ser Gly Gly Gly Gly Ser Gly Gly Gly
            115                 120                 125

Gly Ser Gly Gly Gly Gly Ser
            130                 135

<210> SEQ ID NO 61
<211> LENGTH: 135
<212> TYPE: PRT
<213> ORGANISM: Artificial Sequence
<220> FEATURE:
<223> OTHER INFORMATION: F09_OMPA.ab11 Heavy Chain

<400> SEQUENCE: 61

Glu Val Gln Leu Leu Glu Ser Gly Gly Gly Leu Val Gln Thr Gly Gly
  1               5                  10                  15

Ser Leu Arg Leu Ser Cys Ala Ala Ser Gly Phe Thr Phe Ser Asp Tyr
                 20                  25                  30

Ala Met Glu Thr Ser Trp Val Arg Gln Ala Pro Gly Lys Gly Leu Glu
             35                  40                  45

Trp Val Ser Trp Ile Tyr Tyr Asp Ser Gly Ser Lys Tyr Tyr Ala Asp
 50                  55                  60
```

```
Ser Val Lys Gly Arg Phe Thr Ile Ser Arg Asp Asn Ser Lys Asn Thr
 65                  70                  75                  80

Leu Tyr Leu Gln Met Glu Thr Asn Ser Leu Arg Ala Glu Asp Thr Ala
                 85                  90                  95

Val Tyr Tyr Cys Ala Lys Leu Asn Gly Asp Phe Asp Tyr Trp Gly Gln
            100                 105                 110

Gly Thr Leu Val Thr Val Ser Ser Gly Gly Gly Ser Gly Gly Gly
        115                 120                 125

Gly Ser Gly Gly Gly Gly Ser
        130                 135

<210> SEQ ID NO 62
<211> LENGTH: 135
<212> TYPE: PRT
<213> ORGANISM: Artificial Sequence
<220> FEATURE:
<223> OTHER INFORMATION: F11_OMPA.ab11 Heavy Chain

<400> SEQUENCE: 62

Glu Val Gln Leu Leu Glu Ser Gly Gly Gly Leu Val Gln Thr Gly Gly
 1               5                   10                  15

Ser Leu Arg Leu Ser Cys Ala Ala Ser Gly Phe Thr Phe Ser Asp Tyr
                20                  25                  30

Ala Met Glu Thr Ser Trp Val Arg Gln Ala Pro Gly Lys Gly Leu Glu
            35                  40                  45

Trp Val Ser Trp Ile Tyr Tyr Asp Ser Gly Ser Lys Tyr Tyr Ala Asp
        50                  55                  60

Ser Val Lys Gly Arg Phe Thr Ile Ser Arg Asp Asn Ser Lys Asn Thr
 65                  70                  75                  80

Leu Tyr Leu Gln Met Glu Thr Asn Ser Leu Arg Ala Glu Asp Thr Ala
                 85                  90                  95

Val Tyr Tyr Cys Ala Lys Leu Asn Gly Asp Phe Asp Tyr Trp Gly Gln
            100                 105                 110

Gly Thr Leu Val Thr Val Ser Ser Gly Gly Gly Ser Gly Gly Gly
        115                 120                 125

Gly Ser Gly Gly Gly Gly Ser
        130                 135

<210> SEQ ID NO 63
<211> LENGTH: 135
<212> TYPE: PRT
<213> ORGANISM: Artificial Sequence
<220> FEATURE:
<223> OTHER INFORMATION: F12_OMPA.ab11 Heavy Chain

<400> SEQUENCE: 63

Glu Val Gln Leu Leu Glu Ser Gly Gly Gly Leu Val Gln Thr Gly Gly
 1               5                   10                  15

Ser Leu Arg Leu Ser Cys Ala Ala Ser Gly Phe Thr Phe Ser Asp Tyr
                20                  25                  30

Ala Met Glu Thr Ser Trp Val Arg Gln Ala Pro Gly Lys Gly Leu Glu
            35                  40                  45

Trp Val Ser Trp Ile Tyr Tyr Asp Ser Gly Ser Lys Tyr Tyr Ala Asp
        50                  55                  60

Ser Val Lys Gly Arg Phe Thr Ile Ser Arg Asp Asn Ser Lys Asn Thr
 65                  70                  75                  80

Leu Tyr Leu Gln Met Glu Thr Asn Ser Leu Arg Ala Glu Asp Thr Ala
                 85                  90                  95
```

```
Val Tyr Tyr Cys Ala Lys Leu Asn Gly Asp Phe Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser
    130                 135

<210> SEQ ID NO 64
<211> LENGTH: 135
<212> TYPE: PRT
<213> ORGANISM: Artificial Sequence
<220> FEATURE:
<223> OTHER INFORMATION: G08_OMPA.ab11 Heavy Chain

<400> SEQUENCE: 64

Glu Val Gln Leu Leu Glu Ser Gly Gly Gly Leu Val Gln Thr Gly Gly
1               5                   10                  15

Ser Leu Arg Leu Ser Cys Ala Ala Ser Gly Phe Thr Phe Ser Asp Tyr
            20                  25                  30

Ala Met Glu Thr Ser Trp Val Arg Gln Ala Pro Gly Lys Gly Leu Glu
        35                  40                  45

Trp Val Ser Trp Ile Tyr Tyr Asp Ser Gly Ser Lys Tyr Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Met Glu Thr Asn Ser Leu Arg Ala Glu Asp Thr Ala
                85                  90                  95

Val Tyr Tyr Cys Ala Lys Leu Asn Gly Asp Phe Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser
    130                 135

<210> SEQ ID NO 65
<211> LENGTH: 135
<212> TYPE: PRT
<213> ORGANISM: Artificial Sequence
<220> FEATURE:
<223> OTHER INFORMATION: H09_OMPA.ab11 Heavy Chain

<400> SEQUENCE: 65

Glu Val Gln Leu Leu Glu Ser Gly Gly Gly Leu Val Gln Thr Gly Gly
1               5                   10                  15

Ser Leu Arg Leu Ser Cys Ala Ala Ser Gly Phe Thr Phe Ser Asp Tyr
            20                  25                  30

Ala Met Glu Thr Ser Trp Val Arg Gln Ala Pro Gly Lys Gly Leu Glu
        35                  40                  45

Trp Val Ser Trp Ile Tyr Tyr Asp Ser Gly Ser Lys Tyr Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Met Glu Thr Asn Ser Leu Arg Ala Glu Asp Thr Ala
                85                  90                  95

Val Tyr Tyr Cys Ala Lys Leu Asn Gly Asp Phe Asp Tyr Trp Gly Gln
            100                 105                 110

Gly Thr Leu Val Thr Val Ser Ser Gly Gly Gly Gly Ser Gly Gly Gly
```

```
        115                 120                 125
Gly Ser Gly Gly Gly Gly Ser
    130                 135

<210> SEQ ID NO 66
<211> LENGTH: 135
<212> TYPE: PRT
<213> ORGANISM: Artificial Sequence
<220> FEATURE:
<223> OTHER INFORMATION: D10_OMPA.ab11 Heavy Chain

<400> SEQUENCE: 66

Glu Val Gln Leu Leu Glu Ser Gly Gly Gly Leu Val Gln Thr Gly Gly
1               5                   10                  15

Ser Leu Arg Leu Ser Cys Ala Ala Ser Gly Phe Thr Phe Ser Asp Tyr
            20                  25                  30

Ala Met Glu Thr Ser Trp Val Arg Gln Ala Pro Gly Lys Gly Leu Glu
        35                  40                  45

Trp Val Ser Trp Ile Tyr Tyr Asp Ser Gly Ser Lys Tyr Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Met Glu Thr Asn Ser Leu Arg Ala Glu Asp Thr Ala
                85                  90                  95

Val Tyr Tyr Cys Ala Lys Leu Asn Gly Asp Phe Asp Tyr Trp Gly Gln
            100                 105                 110

Gly Thr Leu Val Thr Val Ser Ser Gly Gly Gly Ser Gly Gly Gly
        115                 120                 125

Gly Ser Gly Gly Gly Gly Ser
    130                 135

<210> SEQ ID NO 67
<211> LENGTH: 135
<212> TYPE: PRT
<213> ORGANISM: Artificial Sequence
<220> FEATURE:
<223> OTHER INFORMATION: D12_OMPA.ab11 Heavy Chain

<400> SEQUENCE: 67

Glu Val Gln Leu Leu Glu Ser Gly Gly Gly Leu Val Gln Thr Gly Gly
1               5                   10                  15

Ser Leu Arg Leu Ser Cys Ala Ala Ser Gly Phe Thr Phe Ser Asp Tyr
            20                  25                  30

Ala Met Glu Thr Ser Trp Val Arg Gln Ala Pro Gly Lys Gly Leu Glu
        35                  40                  45

Trp Val Ser Trp Ile Tyr Tyr Asp Ser Gly Ser Lys Tyr Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Met Glu Thr Asn Ser Leu Arg Ala Glu Asp Thr Ala
                85                  90                  95

Val Tyr Tyr Cys Ala Lys Leu Asn Gly Asp Phe Asp Tyr Trp Gly Gln
            100                 105                 110

Gly Thr Leu Val Thr Val Ser Ser Gly Gly Gly Ser Gly Gly Gly
        115                 120                 125

Gly Ser Gly Gly Gly Gly Ser
    130                 135
```

-continued

<210> SEQ ID NO 68
<211> LENGTH: 135
<212> TYPE: PRT
<213> ORGANISM: Artificial Sequence
<220> FEATURE:
<223> OTHER INFORMATION: C11_OMPA.ab11 Heavy Chain

<400> SEQUENCE: 68

Glu Val Gln Leu Leu Glu Ser Gly Gly Gly Leu Val Gln Thr Gly Gly
1               5                   10                  15

Ser Leu Arg Leu Ser Cys Ala Ala Ser Gly Phe Thr Phe Ser Asp Tyr
            20                  25                  30

Ala Met Glu Thr Ser Trp Val Arg Gln Ala Pro Gly Lys Gly Leu Glu
        35                  40                  45

Trp Val Ser Trp Ile Tyr Tyr Asp Ser Gly Ser Lys Tyr Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Met Glu Thr Asn Ser Leu Arg Ala Glu Asp Thr Ala
                85                  90                  95

Val Tyr Tyr Cys Ala Lys Leu Asn Gly Asp Phe Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser
    130                 135

<210> SEQ ID NO 69
<211> LENGTH: 135
<212> TYPE: PRT
<213> ORGANISM: Artificial Sequence
<220> FEATURE:
<223> OTHER INFORMATION: C12_OMPA.ab11 Heavy Chain

<400> SEQUENCE: 69

Glu Val Gln Leu Leu Glu Ser Gly Gly Gly Leu Val Gln Thr Gly Gly
1               5                   10                  15

Ser Leu Arg Leu Ser Cys Ala Ala Ser Gly Phe Thr Phe Ser Asp Tyr
            20                  25                  30

Ala Met Glu Thr Ser Trp Val Arg Gln Ala Pro Gly Lys Gly Leu Glu
        35                  40                  45

Trp Val Ser Trp Ile Tyr Tyr Asp Ser Gly Ser Lys Tyr Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Met Glu Thr Asn Ser Leu Arg Ala Glu Asp Thr Ala
                85                  90                  95

Val Tyr Tyr Cys Ala Lys Leu Asn Gly Asp Phe Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser
    130                 135

<210> SEQ ID NO 70
<211> LENGTH: 135
<212> TYPE: PRT
<213> ORGANISM: Artificial Sequence
<220> FEATURE:
<223> OTHER INFORMATION: B12_OMPA.ab11 Heavy Chain

<400> SEQUENCE: 70

Glu Val Gln Leu Leu Glu Ser Gly Gly Gly Leu Val Gln Thr Gly Gly
1               5                   10                  15

Ser Leu Arg Leu Ser Cys Ala Ala Ser Gly Phe Thr Phe Ser Asp Tyr
            20                  25                  30

Ala Met Glu Thr Ser Trp Val Arg Gln Ala Pro Gly Lys Gly Leu Glu
        35                  40                  45

Trp Val Ser Trp Ile Tyr Tyr Asp Ser Gly Ser Lys Tyr Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Met Glu Thr Asn Ser Leu Arg Ala Glu Asp Thr Ala
                85                  90                  95

Val Tyr Tyr Cys Ala Lys Leu Asn Gly Asp Phe Asp Tyr Trp Gly Gln
            100                 105                 110

Gly Thr Leu Val Thr Val Ser Ser Gly Gly Gly Gly Ser Gly Gly Gly
            115                 120                 125

Gly Ser Gly Gly Gly Gly Ser
        130                 135

<210> SEQ ID NO 71
<211> LENGTH: 135
<212> TYPE: PRT
<213> ORGANISM: Artificial Sequence
<220> FEATURE:
<223> OTHER INFORMATION: C09_OMPA.ab11 Heavy Chain

<400> SEQUENCE: 71

Glu Val Gln Leu Leu Glu Ser Gly Gly Gly Leu Val Gln Thr Gly Gly
1               5                   10                  15

Ser Leu Arg Leu Ser Cys Ala Ala Ser Gly Phe Thr Phe Ser Asp Tyr
            20                  25                  30

Ala Met Glu Thr Ser Trp Val Arg Gln Ala Pro Gly Lys Gly Leu Glu
        35                  40                  45

Trp Val Ser Trp Ile Tyr Tyr Asp Ser Gly Ser Lys Tyr Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Met Glu Thr Asn Ser Leu Arg Ala Glu Asp Thr Ala
                85                  90                  95

Val Tyr Tyr Cys Ala Lys Leu Asn Gly Asp Phe Asp Tyr Trp Gly Gln
            100                 105                 110

Gly Thr Leu Val Thr Val Ser Ser Gly Gly Gly Gly Ser Gly Gly Gly
            115                 120                 125

Gly Ser Gly Gly Gly Gly Ser
        130                 135

<210> SEQ ID NO 72
<211> LENGTH: 135
<212> TYPE: PRT
<213> ORGANISM: Artificial Sequence
<220> FEATURE:
<223> OTHER INFORMATION: A11_OMPA.ab11 Heavy Chain

<400> SEQUENCE: 72

Glu Val Gln Leu Leu Glu Ser Gly Gly Gly Leu Val Gln Thr Gly Gly
1               5                   10                  15

Ser Leu Arg Leu Ser Cys Ala Ala Ser Gly Phe Thr Phe Ser Asp Tyr
            20                  25                  30

Ala Met Glu Thr Ser Trp Val Arg Gln Ala Pro Gly Lys Gly Leu Glu
        35                  40                  45

Trp Val Ser Trp Ile Tyr Tyr Asp Ser Gly Ser Lys Tyr Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Met Glu Thr Asn Ser Leu Arg Ala Glu Asp Thr Ala
                85                  90                  95

Val Tyr Tyr Cys Ala Lys Leu Asn Gly Asp Phe Asp Tyr Trp Gly Gln
                100                 105                 110

Gly Thr Leu Val Thr Val Ser Ser Gly Gly Gly Ser Gly Gly Gly
            115                 120                 125

Gly Ser Gly Gly Gly Gly Ser
        130                 135

<210> SEQ ID NO 73
<211> LENGTH: 135
<212> TYPE: PRT
<213> ORGANISM: Artificial Sequence
<220> FEATURE:
<223> OTHER INFORMATION: B08_OMPA.ab11 Heavy Chain

<400> SEQUENCE: 73

Glu Val Gln Leu Leu Glu Ser Gly Gly Gly Leu Val Gln Thr Gly Gly
1               5                   10                  15

Ser Leu Arg Leu Ser Cys Ala Ala Ser Gly Phe Thr Phe Ser Asp Tyr
            20                  25                  30

Ala Met Glu Thr Ser Trp Val Arg Gln Ala Pro Gly Lys Gly Leu Glu
        35                  40                  45

Trp Val Ser Trp Ile Tyr Tyr Asp Ser Gly Ser Lys Tyr Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Met Glu Thr Asn Ser Leu Arg Ala Glu Asp Thr Ala
                85                  90                  95

Val Tyr Tyr Cys Ala Lys Leu Asn Gly Asp Phe Asp Tyr Trp Gly Gln
                100                 105                 110

Gly Thr Leu Val Thr Val Ser Ser Gly Gly Gly Ser Gly Gly Gly
            115                 120                 125

Gly Ser Gly Gly Gly Gly Ser
        130                 135

<210> SEQ ID NO 74
<211> LENGTH: 135
<212> TYPE: PRT
<213> ORGANISM: Artificial Sequence
<220> FEATURE:
<223> OTHER INFORMATION: B09_OMPA.ab11 Heavy Chain

<400> SEQUENCE: 74

Glu Val Gln Leu Leu Glu Ser Gly Gly Gly Leu Val Gln Thr Gly Gly
1               5                   10                  15

Ser Leu Arg Leu Ser Cys Ala Ala Ser Gly Phe Thr Phe Ser Asp Tyr
            20                  25                  30

Ala Met Glu Thr Ser Trp Val Arg Gln Ala Pro Gly Lys Gly Leu Glu
            35                  40                  45

Trp Val Ser Trp Ile Tyr Tyr Asp Ser Gly Ser Lys Tyr Tyr Ala Asp
 50                  55                  60

Ser Val Lys Gly Arg Phe Thr Ile Ser Arg Asp Asn Ser Lys Asn Thr
 65                  70                  75                  80

Leu Tyr Leu Gln Met Glu Thr Asn Ser Leu Arg Ala Glu Asp Thr Ala
            85                  90                  95

Val Tyr Tyr Cys Ala Lys Leu Asn Gly Asp Phe Asp Tyr Trp Gly Gln
            100                 105                 110

Gly Thr Leu Val Thr Val Ser Ser Gly Gly Gly Ser Gly Gly
            115                 120                 125

Gly Ser Gly Gly Gly Ser
            130                 135

<210> SEQ ID NO 75
<211> LENGTH: 137
<212> TYPE: PRT
<213> ORGANISM: Artificial Sequence
<220> FEATURE:
<223> OTHER INFORMATION: A10_OMPA.ab11 Heavy Chain

<400> SEQUENCE: 75

Glu Val Gln Leu Leu Glu Ser Gly Gly Gly Leu Val Gln Pro Gly Gly
 1               5                   10                  15

Ser Leu Arg Leu Ser Cys Ala Ala Ser Gly Phe Thr Phe Ser Asp Tyr
            20                  25                  30

Ala Met Glu Thr Ser Trp Val Arg Gln Ala Pro Gly Lys Gly Leu Glu
            35                  40                  45

Trp Val Ser Gly Ile Tyr Tyr Asp Gly Gly Asn Thr Tyr Tyr Ala Asp
 50                  55                  60

Ser Val Lys Gly Arg Phe Thr Ile Ser Arg Asp Asn Ser Lys Asn Thr
 65                  70                  75                  80

Leu Tyr Leu Gln Met Glu Thr Asn Ser Leu Arg Ala Glu Asp Thr Ala
            85                  90                  95

Val Tyr Tyr Cys Ala Arg Met Glu Thr Tyr Gly Pro Phe Asp Tyr Trp
            100                 105                 110

Gly Gln Gly Thr Leu Val Thr Val Ser Ser Gly Gly Gly Ser Gly
            115                 120                 125

Gly Gly Gly Ser Gly Gly Gly Ser
            130                 135

<210> SEQ ID NO 76
<211> LENGTH: 135
<212> TYPE: PRT
<213> ORGANISM: Artificial Sequence
<220> FEATURE:
<223> OTHER INFORMATION: C10_OMPA.ab11 Heavy Chain

<400> SEQUENCE: 76

Glu Val Gln Leu Leu Glu Ser Gly Gly Gly Leu Val Gln Pro Gly Gly
 1               5                   10                  15

Ser Leu Arg Leu Ser Cys Ala Ala Ser Gly Phe Thr Phe Ser Asp Tyr
            20                  25                  30

Ala Met Glu Thr Ser Trp Val Arg Gln Ala Pro Gly Lys Gly Leu Glu
            35                  40                  45

Trp Val Ser Gly Ile Tyr Tyr Asp Asp Ser Ser Gln Tyr Tyr Ala Asp

```
Ser Val Glu Gly Arg Phe Thr Ile Ser Arg Asp Asn Ser Lys Asn Thr
 65                  70                  75                  80

Leu Tyr Leu Gln Met Glu Thr Asn Ser Leu Arg Ala Glu Asp Thr Ala
                 85                  90                  95

Val Tyr Tyr Cys Ala Arg Tyr Leu Gly Leu Phe Asp Tyr Trp Gly Gln
            100                 105                 110

Gly Thr Leu Val Thr Val Ser Ser Gly Gly Gly Ser Gly Gly Gly
        115                 120                 125

Gly Ser Gly Gly Gly Gly Ser
        130                 135

<210> SEQ ID NO 77
<211> LENGTH: 135
<212> TYPE: PRT
<213> ORGANISM: Artificial Sequence
<220> FEATURE:
<223> OTHER INFORMATION: H11_OMPA.ab11 Heavy Chain

<400> SEQUENCE: 77

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Ala Met Glu Thr Ser Trp Val Arg Gln Ala Pro Gly Lys Gly Leu Glu
        35                  40                  45

Trp Val Ser Gly Ile Tyr Tyr Asp Asp Ser Ser Gln Tyr Tyr Ala Asp
    50                  55                  60

Ser Val Glu Gly Arg Phe Thr Ile Ser Arg Asp Asn Ser Lys Asn Thr
 65                  70                  75                  80

Leu Tyr Leu Gln Met Glu Thr Asn Ser Leu Arg Ala Glu Asp Thr Ala
                 85                  90                  95

Val Tyr Tyr Cys Ala Arg Tyr Leu Gly Leu Phe Asp Tyr Trp Gly Gln
            100                 105                 110

Gly Thr Leu Val Thr Val Ser Ser Gly Gly Gly Ser Gly Gly Gly
        115                 120                 125

Gly Ser Gly Gly Gly Gly Ser
        130                 135

<210> SEQ ID NO 78
<211> LENGTH: 135
<212> TYPE: PRT
<213> ORGANISM: Artificial Sequence
<220> FEATURE:
<223> OTHER INFORMATION: C01_ompA.ab19 Heavy Chain

<400> SEQUENCE: 78

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Ala Met Glu Thr Ser Trp Val Arg Gln Ala Pro Gly Lys Gly Leu Glu
        35                  40                  45

Trp Val Ser Gly Ile Tyr Tyr Asp Asp Ser Ser Gln Tyr Tyr Ala Asp
    50                  55                  60

Ser Val Glu Gly Arg Phe Thr Ile Ser Arg Asp Asn Ser Lys Asn Thr
 65                  70                  75                  80
```

```
Leu Tyr Leu Gln Met Glu Thr Asn Ser Leu Arg Ala Glu Asp Thr Ala
                85                  90                  95

Val Tyr Tyr Cys Ala Arg Tyr Leu Gly Leu Phe Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser
    130                 135

<210> SEQ ID NO 79
<211> LENGTH: 148
<212> TYPE: PRT
<213> ORGANISM: Artificial Sequence
<220> FEATURE:
<223> OTHER INFORMATION: E10_OMPA.ab11 Heavy Chain

<400> SEQUENCE: 79

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Asp Met Glu Thr Ser Trp Val Arg Gln Ala Pro Gly Lys Gly Leu Glu
        35                  40                  45

Trp Val Ser Gly Ile Ser Tyr Asp Gly Ser Ser Ile Tyr Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Met Glu Thr Asn Ser Leu Arg Ala Glu Asp Thr Ala
                85                  90                  95

Val Tyr Tyr Cys Ala Arg Asp Leu Arg Phe Cys Ala Asn Glu Trp Cys
            100                 105                 110

Tyr Tyr Ala Asp Gly Met Glu Thr Asp Val Trp Gly Gln Gly Thr Leu
        115                 120                 125

Val Thr Val Ser Ser Gly Gly Gly Gly Ser Gly Gly Gly Gly Ser Gly
    130                 135                 140

Gly Gly Ser
145

<210> SEQ ID NO 80
<211> LENGTH: 110
<212> TYPE: PRT
<213> ORGANISM: Artificial Sequence
<220> FEATURE:
<223> OTHER INFORMATION: A08_OMPA.ab11 Light Chain

<400> SEQUENCE: 80

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ser Asn
            20                  25                  30

Ala Val Thr Trp Tyr Gln Gln Leu Pro Gly Thr Ala Pro Lys Leu Leu
        35                  40                  45

Ile Tyr Asp Asp Asn His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ala Trp Asp Ser Ser Leu
                85                  90                  95
```

```
Ser Ala Tyr Val Phe Gly Gly Gly Thr Lys Leu Thr Val Ile
            100                 105                 110

<210> SEQ ID NO 81
<211> LENGTH: 110
<212> TYPE: PRT
<213> ORGANISM: Artificial Sequence
<220> FEATURE:
<223> OTHER INFORMATION: A03_opmA.ab11 Light Chain

<400> SEQUENCE: 81

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ser Asn
            20                  25                  30

Ala Val Thr Trp Tyr Gln Gln Leu Pro Gly Thr Ala Pro Lys Leu Leu
        35                  40                  45

Ile Tyr Asp Asp Asn His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ala Trp Asp Asp Ser Leu
                85                  90                  95

Ser Ala Tyr Val Phe Gly Gly Gly Thr Lys Leu Thr Val Ile
            100                 105                 110

<210> SEQ ID NO 82
<211> LENGTH: 110
<212> TYPE: PRT
<213> ORGANISM: Artificial Sequence
<220> FEATURE:
<223> OTHER INFORMATION: C04_opmA.ab11 Light Chain

<400> SEQUENCE: 82

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ser Asn
            20                  25                  30

Ala Val Thr Trp Tyr Gln Gln Leu Pro Gly Thr Ala Pro Lys Leu Leu
        35                  40                  45

Ile Tyr Asp Asp Asn His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ala Trp Asp Asp Ser Leu
                85                  90                  95

Ser Ala Tyr Val Phe Gly Gly Gly Thr Lys Leu Thr Val Ile
            100                 105                 110

<210> SEQ ID NO 83
<211> LENGTH: 110
<212> TYPE: PRT
<213> ORGANISM: Artificial Sequence
<220> FEATURE:
<223> OTHER INFORMATION: F06_opmA.ab11 Light Chain

<400> SEQUENCE: 83

Gln Ser Val Leu Thr Gln Pro Pro Ser Ala Ser Gly Thr Pro Gly Gln
1               5                   10                  15
```

-continued

Arg Val Thr Ile Ser Cys Thr Gly Ser Ser Asn Ile Gly Ser Asn
            20                  25                  30

Ala Val Thr Trp Tyr Gln Gln Leu Pro Gly Thr Ala Pro Lys Leu Leu
            35                  40                  45

Ile Tyr Asp Asp Asn His Arg Pro Ser Gly Val Pro Asp Arg Phe Ser
        50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ala Trp Asp Ser Ser Leu
                85                  90                  95

Ser Ala Tyr Val Phe Gly Gly Gly Thr Lys Leu Thr Val Ile
            100                 105                 110

<210> SEQ ID NO 84
<211> LENGTH: 110
<212> TYPE: PRT
<213> ORGANISM: Artificial Sequence
<220> FEATURE:
<223> OTHER INFORMATION: B05_opmA.ab11 Light Chain

<400> SEQUENCE: 84

Gln Ser Val Leu Thr Gln Pro Pro Ser Ala Ser Gly Thr Pro Gly Gln
1               5                   10                  15

Arg Val Thr Ile Ser Cys Thr Gly Ser Ser Asn Ile Gly Asn Asn
            20                  25                  30

Asp Val Ser Trp Tyr Gln Gln Leu Pro Gly Thr Ala Pro Lys Leu Leu
            35                  40                  45

Ile Tyr Ala Asp Ser His Arg Pro Ser Gly Val Pro Asp Arg Phe Ser
        50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ala Trp Asp Ser Ser Leu
                85                  90                  95

Ser Gly Tyr Val Phe Gly Gly Gly Thr Lys Leu Thr Val Ile
            100                 105                 110

<210> SEQ ID NO 85
<211> LENGTH: 110
<212> TYPE: PRT
<213> ORGANISM: Artificial Sequence
<220> FEATURE:
<223> OTHER INFORMATION: F03_opmA.ab11 Light Chain

<400> SEQUENCE: 85

Gln Ser Val Leu Thr Gln Pro Pro Ser Ala Ser Gly Thr Pro Gly Gln
1               5                   10                  15

Arg Val Thr Ile Ser Cys Thr Gly Ser Ser Asn Ile Gly Asn Asn
            20                  25                  30

Asp Val Ser Trp Tyr Gln Gln Leu Pro Gly Thr Ala Pro Lys Leu Leu
            35                  40                  45

Ile Tyr Ala Asp Ser His Arg Pro Ser Gly Val Pro Asp Arg Phe Ser
        50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ala Trp Asp Ser Ser Leu
                85                  90                  95

Ser Gly Tyr Val Phe Gly Gly Gly Thr Lys Leu Thr Val Ile
            100                 105                 110

<210> SEQ ID NO 86
<211> LENGTH: 110
<212> TYPE: PRT
<213> ORGANISM: Artificial Sequence
<220> FEATURE:
<223> OTHER INFORMATION: B04_opmA.ab11 Light Chain

<400> SEQUENCE: 86

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Asn Asn
            20                  25                  30

Asp Val Ser Trp Tyr Gln Gln Leu Pro Gly Thr Ala Pro Lys Leu Leu
        35                  40                  45

Ile Tyr Ala Asp Ser His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ala Trp Asp Ser Ser Leu
                85                  90                  95

Ser Gly Tyr Val Phe Gly Gly Gly Thr Lys Leu Thr Val Ile
            100                 105                 110

<210> SEQ ID NO 87
<211> LENGTH: 110
<212> TYPE: PRT
<213> ORGANISM: Artificial Sequence
<220> FEATURE:
<223> OTHER INFORMATION: A06_opmA.ab11 Light Chain

<400> SEQUENCE: 87

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Asn Asn
            20                  25                  30

Asp Val Ser Trp Tyr Gln Gln Leu Pro Gly Thr Ala Pro Lys Leu Leu
        35                  40                  45

Ile Tyr Ala Asp Ser His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ala Trp Asp Ser Ser Leu
                85                  90                  95

Ser Gly Tyr Val Phe Gly Gly Gly Thr Lys Leu Thr Val Ile
            100                 105                 110

<210> SEQ ID NO 88
<211> LENGTH: 110
<212> TYPE: PRT
<213> ORGANISM: Artificial Sequence
<220> FEATURE:
<223> OTHER INFORMATION: B02_opmA.ab19 Light Chain

<400> SEQUENCE: 88

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Asn Asn
            20                  25                  30

Asp Val Ser Trp Tyr Gln Gln Leu Pro Gly Thr Ala Pro Lys Leu Leu
            35                  40                  45

Ile Tyr Ala Asp Ser His Arg Pro Ser Gly Val Pro Asp Arg Phe Ser
 50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Gly Ala Trp Asp Ser Ser Leu
                 85                  90                  95

Ser Gly Tyr Val Phe Gly Gly Gly Thr Lys Leu Thr Val Ile
            100                 105                 110

<210> SEQ ID NO 89
<211> LENGTH: 110
<212> TYPE: PRT
<213> ORGANISM: Artificial Sequence
<220> FEATURE:
<223> OTHER INFORMATION: E09_OMPA.ab11 Light Chain

<400> SEQUENCE: 89

Gln Ser Val Leu Thr Gln Pro Pro Ser Ala Ser Gly Thr Pro Gly Gln
 1               5                  10                  15

Arg Val Thr Ile Ser Cys Thr Gly Ser Ser Ser Asn Ile Gly Asn Asn
             20                  25                  30

Asp Val Ser Trp Tyr Gln Gln Leu Pro Gly Thr Ala Pro Lys Leu Leu
            35                  40                  45

Ile Tyr Ala Asp Ser His Arg Pro Ser Gly Val Pro Asp Arg Phe Ser
 50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Gly Ala Trp Asp Ser Ser Leu
                 85                  90                  95

Ser Gly Tyr Val Phe Gly Gly Gly Thr Lys Leu Thr Val Ile
            100                 105                 110

<210> SEQ ID NO 90
<211> LENGTH: 110
<212> TYPE: PRT
<213> ORGANISM: Artificial Sequence
<220> FEATURE:
<223> OTHER INFORMATION: E11_OMPA.ab11 Light Chain

<400> SEQUENCE: 90

Gln Ser Val Leu Thr Gln Pro Pro Ser Ala Ser Gly Thr Pro Gly Gln
 1               5                  10                  15

Arg Val Thr Ile Ser Cys Thr Gly Ser Ser Ser Asn Ile Gly Asn Asn
             20                  25                  30

Asp Val Ser Trp Tyr Gln Gln Leu Pro Gly Thr Ala Pro Lys Leu Leu
            35                  40                  45

Ile Tyr Ala Asp Ser His Arg Pro Ser Gly Val Pro Asp Arg Phe Ser
 50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Gly Ala Trp Asp Ser Ser Leu
                 85                  90                  95

Ser Gly Tyr Val Phe Gly Gly Gly Thr Lys Leu Thr Val Ile
            100                 105                 110

<210> SEQ ID NO 91

<211> LENGTH: 110
<212> TYPE: PRT
<213> ORGANISM: Artificial Sequence
<220> FEATURE:
<223> OTHER INFORMATION: E12_OMPA.ab11 Light Chain

<400> SEQUENCE: 91

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Asn Asn
            20                  25                  30

Asp Val Ser Trp Tyr Gln Gln Leu Pro Gly Thr Ala Pro Lys Leu Leu
        35                  40                  45

Ile Tyr Ala Asp Ser His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ala Trp Asp Ser Ser Leu
                85                  90                  95

Ser Gly Tyr Val Phe Gly Gly Gly Thr Lys Leu Thr Val Ile
            100                 105                 110

<210> SEQ ID NO 92
<211> LENGTH: 110
<212> TYPE: PRT
<213> ORGANISM: Artificial Sequence
<220> FEATURE:
<223> OTHER INFORMATION: F09_OMPA.ab11 Light Chain

<400> SEQUENCE: 92

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Asn Asn
            20                  25                  30

Asp Val Ser Trp Tyr Gln Gln Leu Pro Gly Thr Ala Pro Lys Leu Leu
        35                  40                  45

Ile Tyr Ala Asp Ser His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ala Trp Asp Ser Ser Leu
                85                  90                  95

Ser Gly Tyr Val Phe Gly Gly Gly Thr Lys Leu Thr Val Ile
            100                 105                 110

<210> SEQ ID NO 93
<211> LENGTH: 110
<212> TYPE: PRT
<213> ORGANISM: Artificial Sequence
<220> FEATURE:
<223> OTHER INFORMATION: F11_OMPA.ab11 Light Chain

<400> SEQUENCE: 93

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Asn Asn
            20                  25                  30

Asp Val Ser Trp Tyr Gln Gln Leu Pro Gly Thr Ala Pro Lys Leu Leu
        35                  40                  45

Ile Tyr Ala Asp Ser His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ala Trp Asp Ser Ser Leu
                85                  90                  95

Ser Gly Tyr Val Phe Gly Gly Gly Thr Lys Leu Thr Val Ile
            100                 105                 110

<210> SEQ ID NO 94
<211> LENGTH: 110
<212> TYPE: PRT
<213> ORGANISM: Artificial Sequence
<220> FEATURE:
<223> OTHER INFORMATION: F12_OMPA.ab11 Light Chain

<400> SEQUENCE: 94

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Asn Asn
            20                  25                  30

Asp Val Ser Trp Tyr Gln Gln Leu Pro Gly Thr Ala Pro Lys Leu Leu
        35                  40                  45

Ile Tyr Ala Asp Ser His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ala Trp Asp Ser Ser Leu
                85                  90                  95

Ser Gly Tyr Val Phe Gly Gly Gly Thr Lys Leu Thr Val Ile
            100                 105                 110

<210> SEQ ID NO 95
<211> LENGTH: 110
<212> TYPE: PRT
<213> ORGANISM: Artificial Sequence
<220> FEATURE:
<223> OTHER INFORMATION: G08_OMPA.ab11 Light Chain

<400> SEQUENCE: 95

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Asn Asn
            20                  25                  30

Asp Val Ser Trp Tyr Gln Gln Leu Pro Gly Thr Ala Pro Lys Leu Leu
        35                  40                  45

Ile Tyr Ala Asp Ser His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ala Trp Asp Ser Ser Leu
                85                  90                  95

Ser Gly Tyr Val Phe Gly Gly Gly Thr Lys Leu Thr Val Ile
            100                 105                 110

<210> SEQ ID NO 96
<211> LENGTH: 110
<212> TYPE: PRT
<213> ORGANISM: Artificial Sequence
<220> FEATURE:
<223> OTHER INFORMATION: H09_OMPA.ab11 Light Chain

<400> SEQUENCE: 96

```
Gln Ser Val Leu Thr Gln Pro Pro Ser Ala Ser Gly Thr Pro Gly Gln
1               5                   10                  15

Arg Val Thr Ile Ser Cys Thr Gly Ser Ser Asn Ile Gly Asn Asn
            20                  25                  30

Asp Val Ser Trp Tyr Gln Gln Leu Pro Gly Thr Ala Pro Lys Leu Leu
        35                  40                  45

Ile Tyr Ala Asp Ser His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ala Trp Asp Ser Ser Leu
                85                  90                  95

Ser Gly Tyr Val Phe Gly Gly Gly Thr Lys Leu Thr Val Ile
            100                 105                 110
```

<210> SEQ ID NO 97
<211> LENGTH: 110
<212> TYPE: PRT
<213> ORGANISM: Artificial Sequence
<220> FEATURE:
<223> OTHER INFORMATION: D10_OMPA.ab11 Light Sequence

<400> SEQUENCE: 97

```
Gln Ser Val Leu Thr Gln Pro Pro Ser Ala Ser Gly Thr Pro Gly Gln
1               5                   10                  15

Arg Val Thr Ile Ser Cys Thr Gly Ser Ser Asn Ile Gly Asn Asn
            20                  25                  30

Asp Val Ser Trp Tyr Gln Gln Leu Pro Gly Thr Ala Pro Lys Leu Leu
        35                  40                  45

Ile Tyr Ala Asp Ser His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ala Trp Asp Ser Ser Leu
                85                  90                  95

Ser Gly Tyr Val Phe Gly Gly Gly Thr Lys Leu Thr Val Ile
            100                 105                 110
```

<210> SEQ ID NO 98
<211> LENGTH: 110
<212> TYPE: PRT
<213> ORGANISM: Artificial Sequence
<220> FEATURE:
<223> OTHER INFORMATION: D12_OMPA.ab11 Light Chain

<400> SEQUENCE: 98

```
Gln Ser Val Leu Thr Gln Pro Pro Ser Ala Ser Gly Thr Pro Gly Gln
1               5                   10                  15

Arg Val Thr Ile Ser Cys Thr Gly Ser Ser Asn Ile Gly Asn Asn
            20                  25                  30

Asp Val Ser Trp Tyr Gln Gln Leu Pro Gly Thr Ala Pro Lys Leu Leu
        35                  40                  45

Ile Tyr Ala Asp Ser His Arg Pro Ser Gly Val Pro Asp Arg Phe Ser
    50                  55                  60
```

```
Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Gly Ala Trp Asp Ser Ser Leu
                 85                  90                  95

Ser Gly Tyr Val Phe Gly Gly Gly Thr Lys Leu Thr Val Ile
            100                 105                 110

<210> SEQ ID NO 99
<211> LENGTH: 110
<212> TYPE: PRT
<213> ORGANISM: Artificial Sequence
<220> FEATURE:
<223> OTHER INFORMATION: C11_OMPA.ab11 Light Chain

<400> SEQUENCE: 99

Gln Ser Val Leu Thr Gln Pro Pro Ser Ala Ser Gly Thr Pro Gly Gln
  1               5                  10                  15

Arg Val Thr Ile Ser Cys Thr Gly Ser Ser Ser Asn Ile Gly Asn Asn
                 20                  25                  30

Asp Val Ser Trp Tyr Gln Gln Leu Pro Gly Thr Ala Pro Lys Leu Leu
             35                  40                  45

Ile Tyr Ala Asp Ser His Arg Pro Ser Gly Val Pro Asp Arg Phe Ser
 50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Gly Ala Trp Asp Ser Ser Leu
                 85                  90                  95

Ser Gly Tyr Val Phe Gly Gly Gly Thr Lys Leu Thr Val Ile
            100                 105                 110

<210> SEQ ID NO 100
<211> LENGTH: 110
<212> TYPE: PRT
<213> ORGANISM: Artificial Sequence
<220> FEATURE:
<223> OTHER INFORMATION: C12_OMPA.ab11 Light Chain

<400> SEQUENCE: 100

Gln Ser Val Leu Thr Gln Pro Pro Ser Ala Ser Gly Thr Pro Gly Gln
  1               5                  10                  15

Arg Val Thr Ile Ser Cys Thr Gly Ser Ser Ser Asn Ile Gly Asn Asn
                 20                  25                  30

Asp Val Ser Trp Tyr Gln Gln Leu Pro Gly Thr Ala Pro Lys Leu Leu
             35                  40                  45

Ile Tyr Ala Asp Ser His Arg Pro Ser Gly Val Pro Asp Arg Phe Ser
 50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Gly Ala Trp Asp Ser Ser Leu
                 85                  90                  95

Ser Gly Tyr Val Phe Gly Gly Gly Thr Lys Leu Thr Val Ile
            100                 105                 110

<210> SEQ ID NO 101
<211> LENGTH: 110
<212> TYPE: PRT
<213> ORGANISM: Artificial Sequence
<220> FEATURE:
<223> OTHER INFORMATION: B12_OMPA.ab11 Light Sequence
```

```
<400> SEQUENCE: 101

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Asn Asn
            20                  25                  30

Asp Val Ser Trp Tyr Gln Gln Leu Pro Gly Thr Ala Pro Lys Leu Leu
        35                  40                  45

Ile Tyr Ala Asp Ser His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ala Trp Asp Ser Ser Leu
                85                  90                  95

Ser Gly Tyr Val Phe Gly Gly Gly Thr Lys Leu Thr Val Ile
            100                 105                 110

<210> SEQ ID NO 102
<211> LENGTH: 110
<212> TYPE: PRT
<213> ORGANISM: Artificial Sequence
<220> FEATURE:
<223> OTHER INFORMATION: C09_OMPA.ab11 Light Chain

<400> SEQUENCE: 102

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Asn Asn
            20                  25                  30

Asp Val Ser Trp Tyr Gln Gln Leu Pro Gly Thr Ala Pro Lys Leu Leu
        35                  40                  45

Ile Tyr Ala Asp Ser His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ala Trp Asp Ser Ser Leu
                85                  90                  95

Ser Gly Tyr Val Phe Gly Gly Gly Thr Lys Leu Thr Val Ile
            100                 105                 110

<210> SEQ ID NO 103
<211> LENGTH: 110
<212> TYPE: PRT
<213> ORGANISM: Artificial Sequence
<220> FEATURE:
<223> OTHER INFORMATION: A11_OMPA.ab11 Light Sequence

<400> SEQUENCE: 103

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Asn Asn
            20                  25                  30

Asp Val Ser Trp Tyr Gln Gln Leu Pro Gly Thr Ala Pro Lys Leu Leu
        35                  40                  45

Ile Tyr Ala Asp Ser His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80
```

Ser Glu Asp Glu Ala Asp Tyr Tyr Cys Gly Ala Trp Asp Ser Ser Leu
                85                  90                  95

Ser Gly Tyr Val Phe Gly Gly Gly Thr Lys Leu Thr Val Ile
            100                 105                 110

<210> SEQ ID NO 104
<211> LENGTH: 110
<212> TYPE: PRT
<213> ORGANISM: Artificial Sequence
<220> FEATURE:
<223> OTHER INFORMATION: B08_OMPA.ab11 Light Chain

<400> SEQUENCE: 104

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Asn Asn
                20                  25                  30

Asp Val Ser Trp Tyr Gln Gln Leu Pro Gly Thr Ala Pro Lys Leu Leu
            35                  40                  45

Ile Tyr Ala Asp Ser His Arg Pro Ser Gly Val Pro Asp Arg Phe Ser
        50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ala Trp Asp Ser Ser Leu
                85                  90                  95

Ser Gly Tyr Val Phe Gly Gly Gly Thr Lys Leu Thr Val Ile
            100                 105                 110

<210> SEQ ID NO 105
<211> LENGTH: 110
<212> TYPE: PRT
<213> ORGANISM: Artificial Sequence
<220> FEATURE:
<223> OTHER INFORMATION: B09_OMPA.ab11 Light Chain

<400> SEQUENCE: 105

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Asn Asn
                20                  25                  30

Asp Val Ser Trp Tyr Gln Gln Leu Pro Gly Thr Ala Pro Lys Leu Leu
            35                  40                  45

Ile Tyr Ala Asp Ser His Arg Pro Ser Gly Val Pro Asp Arg Phe Ser
        50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ala Trp Asp Ser Ser Leu
                85                  90                  95

Ser Gly Tyr Val Phe Gly Gly Gly Thr Lys Leu Thr Val Ile
            100                 105                 110

<210> SEQ ID NO 106
<211> LENGTH: 110
<212> TYPE: PRT
<213> ORGANISM: Artificial Sequence
<220> FEATURE:
<223> OTHER INFORMATION: A10_OMPA.ab11 Light Chain

<400> SEQUENCE: 106

Gln Ser Val Leu Thr Gln Pro Pro Ser Ala Ser Gly Thr Pro Gly Gln

```
            1               5                   10                  15
Gly Val Thr Ile Ser Cys Thr Gly Ser Ser Ser Asn Ile Gly Ser Asn
                    20                  25                  30

Tyr Val Thr Trp Tyr Gln Lys Leu Pro Gly Thr Ala Pro Lys Leu Leu
            35                  40                  45

Ile Tyr Asn Asp Asn Gln Arg Pro Ser Gly Val Pro Asp Arg Phe Ser
        50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ala Trp Asp Asp Ser Leu
                85                  90                  95

Ser Gly Tyr Val Phe Gly Gly Gly Thr Lys Leu Thr Val Ile
                100                 105                 110
```

<210> SEQ ID NO 107
<211> LENGTH: 110
<212> TYPE: PRT
<213> ORGANISM: Artificial Sequence
<220> FEATURE:
<223> OTHER INFORMATION: C10_OMPA.ab11 Light Sequence

<400> SEQUENCE: 107

```
Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Asn Asn
                20                  25                  30

Ser Val Asn Trp Tyr Gln Lys Leu Pro Gly Thr Ala Pro Lys Leu Leu
            35                  40                  45

Ile Tyr Ser Asp Ser Gln Arg Pro Ser Gly Val Pro Asp Arg Phe Ser
        50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ser Trp Asp Tyr Ser Leu
                85                  90                  95

Ser Ala Tyr Val Phe Gly Gly Gly Thr Lys Leu Thr Val Ile
                100                 105                 110
```

<210> SEQ ID NO 108
<211> LENGTH: 110
<212> TYPE: PRT
<213> ORGANISM: Artificial Sequence
<220> FEATURE:
<223> OTHER INFORMATION: H11_OMPA.ab11 Light Chain

<400> SEQUENCE: 108

```
Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Asn Asn
                20                  25                  30

Ser Val Asn Trp Tyr Gln Lys Leu Pro Gly Thr Ala Pro Lys Leu Leu
            35                  40                  45

Ile Tyr Ser Asp Ser Gln Arg Pro Ser Gly Val Pro Asp Arg Phe Ser
        50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ser Trp Asp Tyr Ser Leu
                85                  90                  95
```

```
Ser Ala Tyr Val Phe Gly Gly Gly Thr Lys Leu Thr Val Ile
            100                 105                 110

<210> SEQ ID NO 109
<211> LENGTH: 110
<212> TYPE: PRT
<213> ORGANISM: Artificial Sequence
<220> FEATURE:
<223> OTHER INFORMATION: C01_ompA.ab19 Light Chain

<400> SEQUENCE: 109

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Asn Asn
                20                  25                  30

Ser Val Asn Trp Tyr Gln Lys Leu Pro Gly Thr Ala Pro Lys Leu Leu
            35                  40                  45

Ile Tyr Ser Asp Ser Gln Arg Pro Ser Gly Val Pro Asp Arg Phe Ser
        50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ser Trp Asp Tyr Ser Leu
                85                  90                  95

Ser Ala Tyr Val Phe Gly Gly Gly Thr Lys Leu Thr Val Ile
            100                 105                 110

<210> SEQ ID NO 110
<211> LENGTH: 110
<212> TYPE: PRT
<213> ORGANISM: Artificial Sequence
<220> FEATURE:
<223> OTHER INFORMATION: E10_OMPA.ab11 Light Chain

<400> SEQUENCE: 110

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ser Asn
                20                  25                  30

Asp Val Thr Trp Tyr Gln Lys Leu Pro Gly Thr Ala Pro Lys Leu Leu
            35                  40                  45

Ile Tyr Asp Asn Asn His Arg Pro Ser Gly Val Pro Asp Arg Phe Ser
        50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Ala Tyr Val Phe Gly Gly Gly Thr Lys Leu Thr Val Ile
            100                 105                 110
```

ANTIBODY TO HUMAN AND MOUSE SEMA3A AND USE THEREOF

CROSS REFERENCE TO RELATED APPLICATIONS

This application is a continuation of U.S. application Ser. No. 15/771,488 filed on Apr. 27, 2018, which is a national phase application of PCT Application No. PCT/KR2016/012072, filed on Oct. 26, 2016, which claims the benefit and priority to Korean Patent Application Nos. 10-2015-0149272, filed on Oct. 27, 2015 and 10-2016-0123233, filed on Sep. 26, 2016. The entire disclosures of the applications identified in this paragraph are incorporated herein by references.

TECHNICAL FIELD

The present invention relates to antibody to be cross-linked to human and mouse Sema3A, and uses thereof.

BACKGROUND

Sema3A is a secretory protein that is composed of an Ig-like(immunoglobulin-like) C2-type domain, a PSI domain and a Sema domain, and it has been known to induce associated signaling by binding to NRP1 and PLXNA1.

Also, it has been reported that a high level of Sema3A specific carcinoma has a high growth rate of cancer cells, increases cancer cell migration, promotes cancer metastasis, and has poor prognosis.

Currently, no anti-cancer agent that inhibits Sema3A has been reported as an anti-cancer target, thus an anti-Sema3A antibody that inhibits the associated signaling by neutralizing the Sema3A may be a new anti-cancer treatment strategy.

Antibodies that inhibit Sema3A can be used as therapeutic agents for anti-cancer therapy such as glioblastoma, pancreatic cancer and liver cancer which are highly expressed in Sema3A.

Further, Sema3A is a factor which plays an important role in the migration of tumor-associated macrophage (AM) that is involved in the growth of cancer, and it is expected that the antibodies against Sema3A would exhibit anti-tumor effects in a variety of cancers.

Sema3A is considered as a therapeutic target for diabetic retinopathy, autoimmune arthritis, neuropathic pain or osteoporosis, and it can be used as therapeutic agents in many associated diseases in addition to anti-cancer therapeutic agents.

DETAILED DESCRIPTION

Technical Problem

The present inventors have endeavored to develop antibodies that can bind to Sema3A, i.e., a factor involved in the growth of cancer cells, and prevent and treat cancers.

As a result, the present inventors have discovered antibody that has the ability to be cross-linked to human Sema3A and mouse Sema3A, and exhibits the ability to inhibit cancer cell growth and migration, thereby having excellent effects of preventing and treating cancers, and completed the present invention.

It is an object of the invention to provide an antibody against human Sema3A or an antigen binding fragment thereof.

It is another object of the invention to provide a nucleic acid molecule encoding a heavy chain variable region of an antibody against the human Sema3A.

It is another object of the invention to provide a nucleic acid molecule encoding a light chain variable region of an antibody against the human Sema3A.

It is another object of the invention to provide a recombinant vector composing the nucleic acid molecule.

It is another object of the invention to provide a host cell transformed with the recombinant vector.

It is another object of the invention to provide a pharmaceutical composition for preventing or treating cancer.

Technical Solution

According to an aspect of the present invention, there is provided an antibody (clone name A08) to human Sema3A or its antigen binding fragment comprising:

(a) a heavy chain variable region comprising the following heavy chain complementarity determining region(CDR) amino acid sequences:

CDRH1 consisting of the amino acid sequence of SEQ ID NO: 1,
CDRH2 consisting of the amino acid sequence of SEQ ID NO: 2, and
CDRH3 consisting of the amino acid sequence of SEQ ID NO: 3; and (b) a light chain variable region comprising the following light chain CDR amino acid sequences:

CDRL1 consisting of the amino acid sequence of SEQ ID NO: 4,
CDRL2 consisting of the amino acid sequence of SEQ ID NO: 5, and
CDRL3 consisting of the amino acid sequence of SEQ ID NO: 6.

According to another aspect of the present invention, there is provided an antibody (clone name C10) to human Sema3A or its antigen binding fragment comprising:

(a) a heavy chain variable region comprising the following heavy chain CDR amino acid sequences:

CDRH1 consisting of the amino acid sequence of SEQ ID NO: 7,
CDRH2 consisting of the amino acid sequence of SEQ ID NO: 8, and
CDRH3 consisting of the amino acid sequence of SEQ ID NO: 9; and (b) a light chain variable region comprising the following light chain CDR amino acid sequences:

CDRL1 consisting of the amino acid sequence of SEQ ID NO: 10,
CDRL2 consisting of the amino acid sequence of SEQ ID NO: 11, and
CDRL3 consisting of the amino acid sequence of SEQ ID NO: 12.

According to still another aspect of the present invention, there is provided an antibody (clone name F11) to human Sema3A or its antigen binding fragment comprising:

(a) a heavy chain variable region comprising the following heavy chain CDR amino acid sequences:

CDRH1 consisting of the amino acid sequence of SEQ ID NO: 13,
CDRH2 consisting of the amino acid sequence of SEQ ID NO: 14, and
CDRH3 consisting of the amino acid sequence of SEQ ID NO: 15; and (b) a light chain variable region comprising the following light chain CDR amino acid sequences:

CDRL1 consisting of the amino acid sequence of SEQ ID NO: 16,

CDRL2 consisting of the amino acid sequence of SEQ ID NO: 17, and

CDRL3 consisting of the amino acid sequence of SEQ ID NO: 18.

The present inventors have endeavored to develop antibodies that can bind to Sema3A, i.e., a factor involved in the growth of cancer cells, and prevent and treat cancers.

As a result, the present inventors have discovered antibody that has the ability to be cross-linked to human Sema3A and mouse Sema3A, and exhibits the ability to inhibit cancer cell growth and migration, thereby having excellent effects of preventing and treating cancers.

The antibody of the present invention has a specific binding ability to human Sema3A. In Particular, the antibody of the present invention has cross-linking ability against human Sema3A and mouse Sema3A.

As used herein, the term "antibody" relating to an antibody to human Sema3A refers to a specific antibody to human Sema3A which specifically binds to human Sema3A. The antibody is meant to include complete antibody forms as well as antigen binding fragments of antibody molecules.

The complete antibody includes two full-length light chains and two full-length heavy chains, and each light chain is linked to the heavy chain by disulfide bond.

The heavy chain constant region includes a gamma (γ), mu (u), alpha (α), delta (δ) and epsilon (c) type, which is classified into sub-classes such as gamma 1 (γ1), gamma2 (γ2), gamma3 (γ3), gamma4 (γ4), alpha1 (α1) and alpha2 (α2).

The light chain constant region includes a kappa (κ) and ramda (λ) type (Cellular and Molecular Immunology, Wonsiewicz, M. J., Ed., Chapter 45, pp. 41-50, W. B. Saunders Co. Philadelphia, Pa. (1991); Nisonoff, A., Introduction to Molecular Immunology, 2nd Ed., Chapter 4,pp. 45-65, sinauer Associates, Inc., Sunderland, Mass. (1984)).

As used herein, the term "antigen binding fragments" refers to fragments retaining an antigen binding function, and include Fab, F(ab'), F(ab')$_2$ Fv and the like.

Among antibody fragments, Fab has one antigen binding site which is composed of one variable domain from each heavy and light chain of the antibody, one constant region of light chain and the first constant region ($C_{H1}$) of heavy chain.

Fab' is different to Fab in the senses that there is a hinge region containing one or more cysteine residues at C-terminal of $C_{H1}$ domain of heavy chain.

F(ab')$_2$ antibody is produced by forming a disulfide bond between cysteine residues of hinge region of Fab'.

Fv is a minimal antibody fragment including only variable region from each heavy and light chain. And recombinant technique to prepare a Fv fragment is disclosed in PCT International Publications WO 88/10649, WO 88/106630, WO 88/07085, WO 88/07086 and WO 88/09344.

Two-chain Fv is linked by non-covalent bond between variable regions of each heavy and light chain, and single-chain Fv is generally linked by covalent bond via a peptide linker between variable regions of each heavy and light chain, or is directly linked to each other at C-terminal, forming a dimer-like structure such as two-chain Fv.

Such antibody fragments may be obtained using a proteolytic enzymes (e.g., Fabs can be obtained by restriction-cleaved of whole antibodies to papain, The F (ab') fragment can be obtained by restriction-cleaved of the whole antibody to pepsin), and may be preferably prepared by genetic recombination techniques.

In one embodiment, the antibody of the present invention is a scFv form or a complete antibody form.

In addition, the heavy chain constant region may be selected from the isotypes consisting of gamma (γ), mu (u), alpha (α), delta (δ) and epsilon (c).

As used herein, the term "heavy chain" refers to both a full-length heavy chain and its fragment, which includes variable domain ($V_H$) containing the amino acid sequence with a variable region sequence for imparting a specificity to antigen and three constant domains ($C_{H1}$, $C_{H2}$ and $C_{H3}$).

The term "light chain" refers to both a full-length light chain and its fragment, which includes variable domain ($V_L$) containing the amino acid sequence with a variable region sequence for specifically binding to antigen and constant domain ($C_L$).

As used herein, the term "CDR (complementarity determining region)" refers to an amino acid sequence of hypervariable region of immunoglobulin heavy and light chain (Kabat et al., *Sequences of Proteins of Immunological Interest*, 4th Ed., U.S. Department of Health and Human Services, National Institutes of Health (1987)). Three CDRs are involved in heavy chain (CDRH1, CDRH2 and CDRH3) and light chain (CDRL1, CDRL2 and CDRL3), respectively. CDR provides a main contacting residue to combine antibody with antigen or epitope.

Human Sema3A antibody or its antigen binding fragment may include variants of amino acid sequences set forth in the appended Sequence Listing, which are capable of specifically recognizing human Sema3A.

For example, amino acid sequence of antibody may be altered to improve binding ability and/or other biological characteristics of antibody. These alterations include, for example, deletion, insertion and/or substitution of amino acid residues of antibody.

Such amino acid variations may be provided on the basis of a relative similarity of amino acid side chains, e.g., hydrophobicity, hydrophilicity, charge, size and the like. By the analysis for size, shape and type of the amino acid side chains, it could be seen that all of arginine, lysine and histidine residues are those having positive charge; alanine, glycine and serine have a similar size; phenylalanine, tryptophan and tyrosine have a similar shape.

Accordingly, based on these considerable factors, arginine, lysine and histidine; alanine, glycine and serine; and phenylalanine, tryptophan and tyrosine may be considered to be biologically functional equivalents.

When introducing variation, a hydropathic index of amino acids may be considered. Based on the hydrophobicity and the charge, the hydropathic index is given to each amino acid:

Isoleucine (+4.5); Valine (+4.2); Leucine (+3.8); Phenylalanine (+2.8); Cysteine/Cystaine (+2.5); Methionine (+1.9); Alanine (+1.8); Glycine (−0.4); Threonine (−0.7); Serine (−0.8); Tryptophan (−0.9); Tyrosine (−1.3); Proline (−1.6); Histidine (−3.2); Glutamate (−3.5); Glutamine (−3.5); Aspartate (−3.5); Asparagine (−3.5); Lysine (−3.9); and Arginine (−4.5).

When imparting an interactive biological function of proteins, the hydropathic index of the amino acid is very important. It is well known to one of skill in the art that variations can possess a similar biological activity only where proteins are replaced with amino acids having similar hydropathic index.

Where variations are intended to introduce based on the hydropathic index, the substitution is preferably performed between amino acid residues having no more than ±2 difference in hydropathic index values, more preferably within ±1, still more preferably within ±0.5.

On the other hand, it is well-known that substitutions between amino acids having similar hydrophilicity values may result in the generation of proteins having biologically equivalent activities.

As disclosed in U.S. Pat. No. 4,554,101, each amino acid residue is assigned the following hydrophilicity values:

Arginine (+3.0); Lysine (+3.0); Aspartate (+3.0±1); Glutamate (+3.0±1); Serine (+0.3); Asparagine (+0.2); Glutamine (+0.2); Glycine (0); Threonine (−0.4); Proline (−0.5±1); Alanine (−0.5); Histidine (−0.5); Cysteine (−1.0); Methionine (−1.3); Valine (−1.5); Leucine (−1.8); Isoleucine (−1.8); Tyrosine (−2.3); Phenylalanine (−2.5); and Tryptophan (−3.4).

Where variations are intended to introduce based on the hydrophilicity values, the substitution is preferably performed between amino acid residues having no more than ±2 difference in hydropathic index values, more preferably within ±1, still more preferably within ±0.5.

The amino acid exchanges in proteins that do not substantially change the activity of the molecule are well known to one skilled in the art (H. Neurath, R. L. Hill, The Proteins, Academic Press, N.Y., 1979).

The most commonly occurring exchanges include exchanges between amino acid residues:

Ala/Ser, Val/Ile, Asp/Glu, Thr/Ser, Ala/Gly, Ala/Thr, Ser/Asn, Ala/Val, Ser/Gly, Thy/Phe, Ala/Pro, Lys/Arg, Asp/Asn, Leu/Ile, Leu/Val, Ala/Glu and Asp/Gly.

Considering the afore-mentioned variations having biologically equivalent activities, it would be understood that either antibody of the present invention or the nucleic acid encoding the same includes sequences that are substantially identical to the sequences set forth in the appended Sequence Listing.

The substantially identical sequences refers to those showing preferably at least 61%, more preferably at least 70%, still more preferably at least 80%, most preferably at least 90% nucleotide similarity to the sequences of the appended Sequence Listing, as measured using one of the sequence comparison algorithms known to those ordinarily skilled in the art, by which the nucleotide sequence of this invention is maximally aligned corresponding on random other nucleotide sequences.

Methods of alignment of sequences for comparison are well-known in the art. Various methods and algorithms of alignment are described in:

Smith and Waterman, *Adv. Appl. Math.* 2:482(1981); Needleman and Wunsch, *J. Mol. Bio.* 48:443(1970); Pearson and Lipman, *Methods in Mol. Biol.* 24: 307-31(1988); Higgins and Sharp, *Gene* 73:237-44(1988); Higgins and Sharp, *CABIOS* 5:151-3 (1989); Corpet et al., *Nuc. Acids Res.* 16:10881-90(1988); Huang et al., *Comp. Appl. BioSci.* 8:155-65(1992) and Pearson et al., *Meth. Mol. Biol.* 24:307-31(1994).

The NCBI Basic Local Alignment Search Tool (BLAST) (Altschul et al., J. Mol. Biol. 215: 403-10 (1990)) is available from several sources, including the National Center for Biological Information (NBCI, Bethesda, Md.) and on the Internet, for use in connection with the sequence analysis programs blastp, blasm, blasttx, tblastn and tblastx. It can be accessed at www.ncbi.nlm.nih.qov/BLAST/. A description of how to determine sequence identity using this program is available at www.ncbi.nlm.nih.gov/BI-AST/blast help.html. In addition, sequencing of framework region (FR) and CDRs in antibody variable regions may be indicated based on the sequences of IMGT (www.imgt.org/) generally accessible in the art.

According to an embodiment of the invention, the heavy chain variable region of A08 antibody comprises the amino acid sequence of SEQ ID NO:19.

According to an embodiment of the invention, the light chain variable region of A08 antibody comprises the amino acid sequence of SEQ ID NO:20.

According to an embodiment of the invention, the heavy chain variable region of C10 antibody comprises the amino acid sequence of SEQ ID NO:21.

According to an embodiment of the invention, the light chain variable region of C10 antibody comprises the amino acid sequence of SEQ ID NO:22.

According to an embodiment of the invention, the heavy chain variable region of F11 antibody comprises the amino acid sequence of SEQ ID NO:23.

According to an embodiment of the invention, the light chain variable region of F11 antibody comprises the amino acid sequence of SEQ ID NO:24.

The antibody of the present invention includes, but not limited to, monoclonal antibody, polyclonal antibody, human antibody, humanized antibody, chimeric antibody, single-chain Fvs(scFV), single-chain antibody, Fab fragment, F(ab') fragment, disulfide-linked Fvs (sdFV) and anti-idiotype (anti-Id) antibody, and epitope-binding fragment thereof.

The antibody of the present invention is basically composed of "heavy chain variable region ($V_H$)-linker-light chain variable region ($V_L$)".

In the scFv antibody of the present invention, the linker refers to an amino acid sequence having a predetermined length which artificially links the heavy chain and light chain variable regions.

The scFv antibody of the present invention may be represented by $V_H$ (SEQ ID NO: 19)-linker-$V_L$ (SEQ ID NO: 20); $V_H$ (SEQ ID NO: 21)-linker-$V_L$ (SEQ ID NO: 22); and $V_H$ (SEQ ID NO: 23)-linker-$V_L$ (SEQ ID NO: 24).

The antibody or its antigen binding fragment of the present invention is specifically cross-linked to human Sema3A and mouse Sema3A.

Since the antibody or its antigen binding fragment of the present invention is capable of specifically binding to human Sema3A as well as mouse Sema3A, more accurate preclinical results can be confirmed in the efficacy evaluation using mouse tumor models.

In another aspect of this invention, there is provided a nucleic acid molecule encoding a heavy chain variable region of an antibody to be cross-linked to human Sema3A and mouse Sema3A comprising the amino acid sequence of SEQ ID NO:19, SEQ ID NO:21 or SEQ ID NO:23.

In another aspect of this invention, there is provided a nucleic acid molecule encoding a light chain variable region of an antibody to be cross-linked to human Sema3A and mouse Sema3A comprising the amino acid sequence of SEQ ID NO:20, SEQ ID NO:22 or SEQ ID NO:24.

As used herein, the term "nucleic acid molecule" collectively refers to RNA (gDNA and cDNA) and DNA molecules, and the basic nucleotides of nucleic acid molecules also include analogues with modified sugar or base as well as natural nucleotides (Scheit, Nucleotide Analogs, John Wiley, N.Y. (1980); Uhlman and Peyman, Chemical Reviews, 90:543-584 (1990)). The sequence of the present nucleic acid molecule encoding the variable region of heavy and light chain could be modified. Such modification includes addition, deletion or non-conservative or conservative substitution of nucleotide.

The nucleic acid molecule of this invention encoding a human Sema3A antibody also includes a nucleotide sequence sharing substantial homology with the above nucleotide sequence.

The substantial homology is determined by aligning the nucleotide sequence of the present invention with other random sequences as much as possible and analyzing the aligned sequence using an algorithm commonly used in the art, wherein the nucleotide sequence sharing homology is at least 80%, more preferably 90% and most preferable 95%.

In still further aspect of this invention, there is provided a recombinant vector comprising the above-described nucleic acid molecules.

As used herein, the term "vector" refers to a tool for expressing target gene in a host cell, including a plasmid vector; a cosmid vector; and a virus vector such as a bacteriophage vector, an adenovirus vector, a retrovirus vector and an adeno-associated virus vector.

According to a preferable embodiment, the nucleic acid molecules encoding the variable regions of light and heavy chains in the vector of the present invention are operatively linked to a promoter.

As used herein, the term "operatively linked" refers to functional linkage between a nucleic acid expression control sequence (for example, a promoter, signal sequence or array of transcription factor binding sites) and a second nucleic acid sequence, wherein the expression control sequence affects transcription and/or translation of the nucleic acid corresponding to the second sequence.

The vector system of the present invention may be performed by various methods known to those skilled in the art and its practical method is described in Sambrook et al., *Molecular Cloning, A Laboratory Manual*, Cold Spring Harbor Laboratory Press (2001), which is incorporated herein by reference.

Typically, the vector of the present invention may be constructed as cloning or expression vector.

In addition, the vector of the present invention may be constructed using a prokaryotic or eukaryotic cell as a host cell.

For instance, in each a vector of the present invention and an eukaryotic cell used as the expression vector and the host cell, the promoter derived from genome of mammalian cell (example: methallothionein promoter, β-actin promoter, human hemoglobin promoter and human muscle creatine promoter) or mammalian virus (example: adenovirus late promoter, vaccinia virus 7.5K promoter, SV40 promoter, cytomegalovirus promoter, tk promoter of HSV, mouse mammary tumor virus (MMTV) promoter, LTR promoter of HIV, promoter of moloney virus, Epstein barr virus (EBV) and Rous sarcoma virus (RSV)) might be used, and polyadenylated sequence might be commonly used as the transcription termination sequence.

The vector of the present invention could be fused with other sequences to facilitate the purification of an antibody expressed from it.

For example, a fused sequence includes glutathione-S-transferase (Pharmacia, USA), maltose-binding protein (NEB, USA), FLAG (IBI, USA) and 6 X His (hexahistidine; Quiagen, USA) and so on.

Since the protein expressed in the vector of the present invention is antibody, expressed antibody could be also purified throughout protein A column in an easy manner without additive sequences for purification.

On the other hand, the expression vector of the present invention includes an antibiotics-resistance gene known to those ordinarily skilled in the art as a selection marker, for example, resistant genes against ampicillin, gentamycin, carbenicillin, chloramphenicol, streptomycin, kanamycin, geneticin, neomycin and tetracycline.

In still another aspect of this invention, there is provided a host cell transformed with the above-described recombinant vector.

The host cells in which the present vector is stably and successively cloned and expressed, also utilize any one known to those skilled in the art, for example, the suitable eukaryotic host cell of the above vector includes COS7 (monkey kidney cell), NSO cell, SP2/0, CHO (Chinese hamster ovary) cell, W138, BHK (baby hamster kidney) cell, MDCK, myeloma cell line, HuT 78 cell and 293 cell, but not limited thereto.

In another aspect of this invention, there is provided a pharmaceutical composition for preventing or treating cancer comprising:

(a) a pharmaceutically effective amount of an antibody or its binding fragment against a human Sema3A; and (b) a pharmaceutically acceptable carrier.

A pharmaceutical composition of the present invention uses, as an active ingredient, the antibody to human Sema3A or its antigen binding fragment of the present invention. Therefore, the overlapping descriptions therebetween are omitted to avoid excessive complication of the specification due to repetitive descriptions thereof.

As can be verified by the following examples, the antibody to human Sema3A of the present invention inhibits the growth of cancer cells derived from various cancers by a considerable binding ability to anti-Sema3A and the suppression of Sema3A function therefrom, inhibits the ERK phosphorylation of downstream signaling molecules of Sema3A and thus suppress the migration of cancer cells, thereby being very efficient in the prevention and treatment of cancers.

The cancers that can be prevented or treated by the composition of the invention may include various cancers known in the art, and examples thereof may include breast cancer, colon cancer, lung cancer, stomach cancer, liver cancer, blood cancer, bone cancer, pancreatic cancer, skin cancer, brain cancer, cervical cancer, nasopharyngeal cancer, laryngeal cancer, colon cancer, ovarian cancer, rectal cancer, colorectal cancer, vaginal cancer, small intestine cancer, endocrine cancer, thyroid cancer, parathyroid cancer, ureter cancer, urinary tract cancer, prostate cancer, bronchial cancer, bladder cancer, kidney cancer and marrow cancer.

Specifically, the cancers that can be prevented or treated by the composition of the present invention are Sema3A expressing cancers.

In the pharmaceutical compositions of the present invention, the pharmaceutically acceptable carrier may be conventional one for formulation, including lactose, dextrose, sucrose, sorbitol, mannitol, starch, Acacia gum, potassium phosphate, alginate, gelatin, potassium silicate, microcrystalline cellulose, polyvinylpyrrolidone, cellulose, water, syrups, methyl cellulose, methylhydroxy benzoate, propylhydroxy benzoate, talc, magnesium stearate and mineral oils, but not limited thereto.

The pharmaceutical composition according to the present invention may further include a lubricant, a humectant, a sweetener, a flavoring agent, an emulsifier, a suspending agent and a preservative.

Details of suitable pharmaceutically acceptable carriers and formulations can be found in Remington's Pharmaceutical Sciences (19th ed., 1995), which is incorporated herein by reference.

The pharmaceutical composition according to the present invention may be administered parenterally. Such parenteral administration includes, for example, intravenous injection, subcutaneous injection, intramuscular injection, intraperitoneal injection or the like.

A suitable dose of the pharmaceutical composition of the present invention may vary depending on various factors such as methods of formulating, methods of administrating, the patient's ages, weights, sex, severities of diseases, diet, administration times, administration routes, excretion rates and reaction sensitivities, and a skilled physician may determine and prescribe pharmaceutically effective dose for the required treatment or prophylaxis easily. in a preferred embodiment, proper daily dose may be 0.0001-100 mg/kg (weight).

As used herein, the term "pharmaceutically effective amount" refers to an amount suitable for preventing or treating cancers.

According to the conventional techniques known to those skilled in the art, the pharmaceutical composition may be formulated with pharmaceutically acceptable carrier and/or vehicle as described above, finally providing several forms including a unit dose form and a multiple dose form.

The formulation may be a solution, a suspension or an emulson in oily or aqueous media or may be extracts, powders, granules, tablets or capsules, and may further comprise a dispersion agent or a stabilzer.

Advantageous Effects

The features and advantages of one or more embodiments of the present invention are summarized as follows:

(a) The present invention provides an antibody having the ability to be cross-linked to human Sema3A and mouse Sema3A.

(b) The antibody of the present invention can be used as therapeutic antibody drugs for inhibiting Sema3A in various cancers such as glioblastoma, pancreatic cancer and liver cancer that exhibit high Sema3A expression levels.

(c) Sema3A is considered to be a therapeutic target of diabetic retinopathy, autoimmune arthritis, neuropathic pain and osteoporosis, the antibody of the present invention or an antigen binding fragment thereof can be used as an agent for treating associated diseases in addition to being used as an anti-cancer drug.

(d) The antibody of the present invention inhibits the growth of cancer cells derived from various cancers by using high Sema3A binding and Sema3A function inhibition caused thereby, and inhibits the migration of cancer cells by inhibiting the phosphorylation of ERK among the downstream signaling materials of Sema3A, thereby being very effective in cancer prevention and treatment.

BRIEF DESCRIPTION OF THE DRAWINGS

FIG. 5a recites SEQ ID NOs: 49-79. FIG. 5b recites SEQ ID NOs: 80-110.

DETAILED DESCRIPTION OF THE EMBODIMENTS

Hereinafter, the present invention will be described in detail with reference to examples. These examples are only for illustrating the present invention more specifically, and it will be apparent to those skilled in the art that the scope of the present invention is not limited by these examples.

EXAMPLE 1

Panning Using Recombinant Human Sema3A Protein

Figure 1:
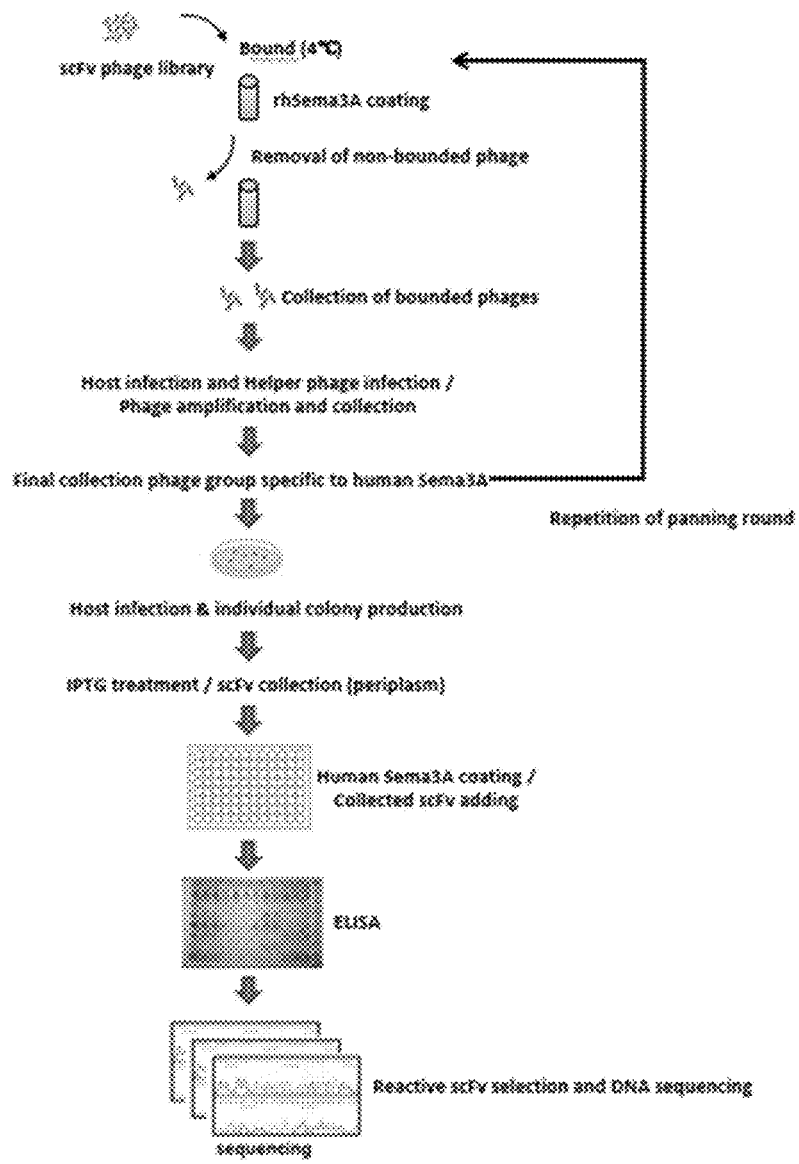
FIG. 1 is a schematic scheme of a phage display selection process for identifying anti-Sema3A scFv antibody fragments.

The scFv antibody fragments cross-linked to human Sema3A were identified through phage display screening by using the existing constructed synthetic scFv phage library (Yang et al., Mol. Cells. 27:225-235, 2009). The phage display screening procedure was shown in FIG. 1.

Specifically, for the collection of phagemid vectors in a phage type, which were introduced into *E. coli* host ER2537, four sub-library samples were respectively cultured in 400 ml of media (SB/ampicillin/2% glucose) for 2 hours. When OD600 is 0.5-0.7, the host cells were centrifuged at 5,000 g for 20 minutes to remove the supernatant, and then suspended in 400 ml of secondary media (SB/ampicillin). Then, $10^{12}$ pfu (plaque forming unit) of helper phage (VCSM13) was added thereto and cultured for 1 hour.

After that, the antibiotic Kanamycin was added at a concentration of 70 ug/ml, followed by culturing overnight at 30° C., so that the phage library was secreted outside the host cell. Then, the centrifuged culture was treated with the polyethylene glycol (PEG) solution to precipitate only phage form, thereby collecting the phage library.

Using the phage library thus obtained, phage display screening was performed through repeated rounds of panning. The counted sub-libraries were collected to $2.5 \times 10^{12}$ pfu, and then treated with the immunotube coated with rhSema3A-Fc protein diluted to 10 ug/ml in TBS for 1 hour. The immunotube and the phage particles before the treatment were treated with a blocking solution containing 3% skim milk for 1 hour, thereby preventing non-specific binding thereof. The immunotube was washed with TBST(0.1% Tween 20) solution and 100 mM TEA was added thereto and kept to stand for 10 minutes, thereby collecting phages bound to Sema3A. For the confirmation of the number of collected phages (output), after infecting the host cells, phage counting was performed in the medium. The remaining collected solution was centrifuged at 3,000 rpm for 15 minutes and then the settled ER2537 was mixed in 500 ul of a culture medium (SB). The mixture was plated on the 15 cm-media and then cultured, and then 5 ml of SB medium (50% glycerol) was added, followed by collection and storage (−80° C.) of colonies.

For the repeated rounds of panning, 50 ul of aliquot was taken from the stored phage solution from the previous round of panning, and subjected to phage particle amplification.

The phage particles which were cultured in the host cell ER2537, added with helper phages, and collected, were separated by PEG precipitation, and the next round of panning using the phage particles were progressed in the same manner.

Figure 2:
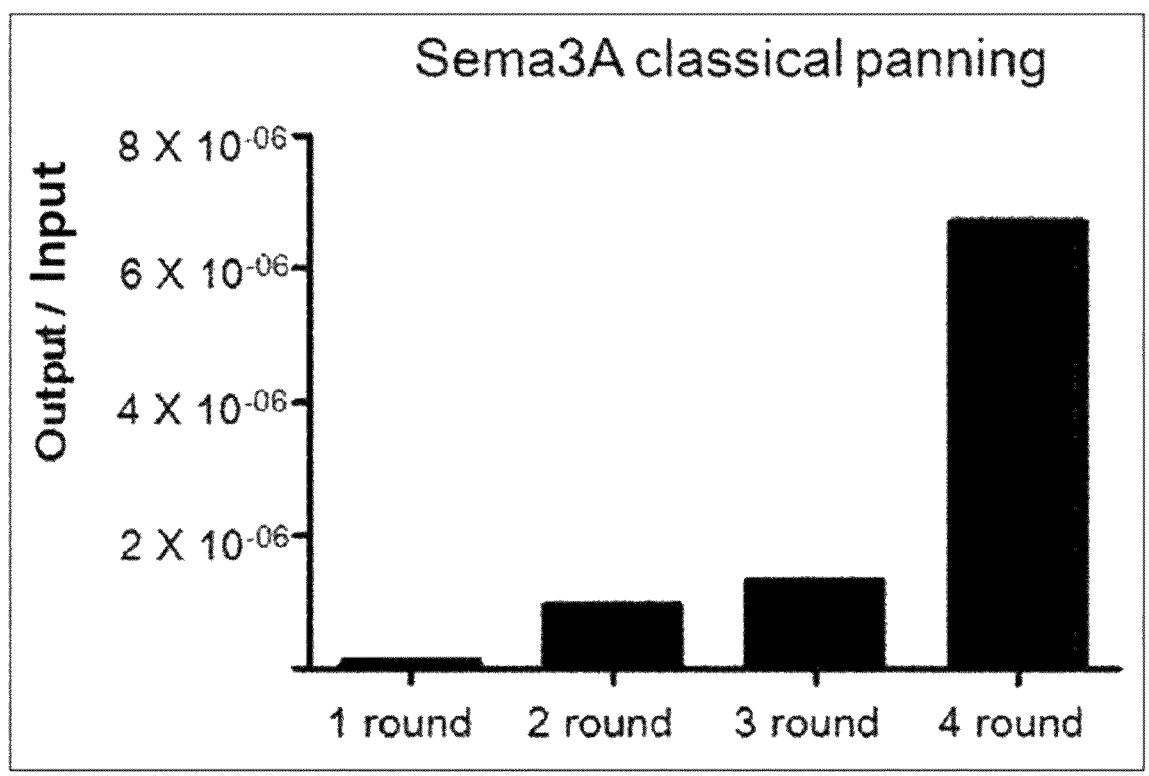
FIG. 2 is a graph showing the phage display panning results.

As the number of panning was increased, it was confirmed that percentages of the phage particles after panning were increased as compared to those before panning. This means that the phage particles specific to Sema3A through the panning were amplified. The results were shown in FIG. 2.

EXAMPLE 2

ELISA and Sequence Analysis for Selection of Anti-Sema3A scFv Candidates

The phage particles collected from the fourth round of panning were confirmed as colonies in the medium through infection of host cell ER2537. These colonies were taken and inoculated in a 96 well plate containing 200 ul of SB/ampicillin media and then cultured at 37° C. for 2-3 hours.

After that, for the induction of scFv-pIII protein expression, the final concentration of 1 mM of IPTG (isopropyl-D-1-thiogalactopyranoside) was added to each well, followed by culturing overnight at 30° C. The cultured plate was centrifuged at 3,000 rpm for 15 minutes to remove the supernatant.

Then, for the collection of phage particles in the periplasm of the cultured cells, the culture plate was added with 40 ul of TES solution (20% w/v sucrose, 50 mM Tris, 1 mM EDTA, pH 8.0) in each well and then kept to stand at 4° C. for 30 minutes, so that the cells were lysed.

After that, the cells were treated with 60 ul of 0.2× TES solution, and then kept to stand for at 4° C. for 30 minutes.

After lysing the cells under osmotic pressure, the plate was centrifuged at 3,000 rpm for 15 minutes, thereby obtaining scFv-pIII protein of the supernatant.

25 ul of the supernatant thus obtained was added to each well of a 96 well plate coated with Sema3A protein, which was previously prepared, followed by binding at room temperature for 1 hour, and subsequently, washing procedures were performed for six times using TBST and distilled water.

Then, anti-HA antibody bound to HRP capable of binding to HA-tag in scFv pIII was added, followed by binding at room temperature for 1 hour, and subsequently, washing procedures were performed for six times using TBST (0.1% Tween20) and distilled water.

Figure 3:
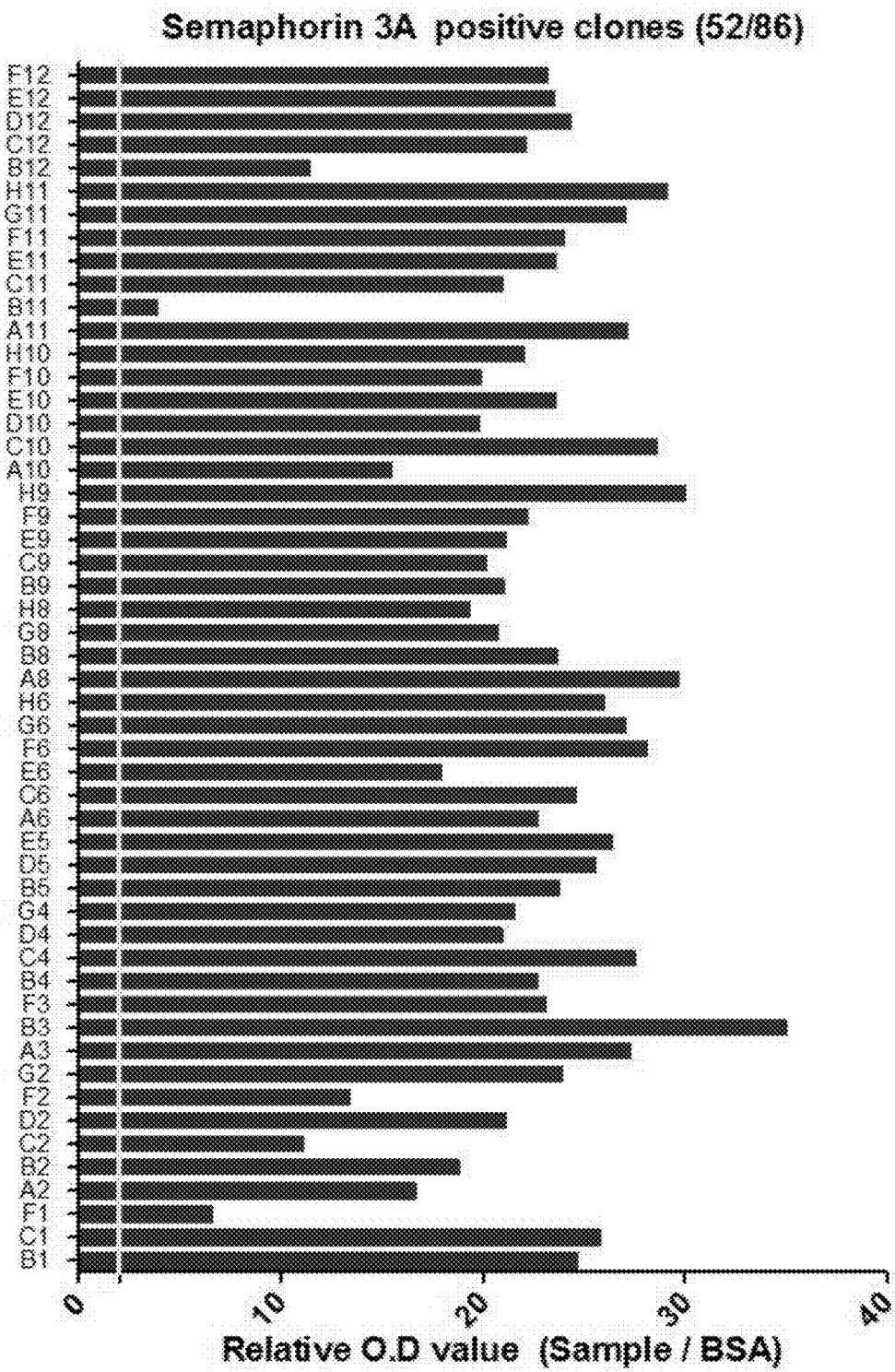
FIG. 3 shows results analyzing binding abilities of 52 species of scFv antibody fragments cross-linked to human Sema3A.

After induction of a color reaction using TMB solution, the color reaction was stopped with addition of $H_2SO_4$ solution and the values thereof were measured at O.D. 450 nm. A total of 86 clones were analyzed, and 52 clones (binding affinity >2-fold) out of them showed a higher binding affinity to Sema3A (FIG. 3).

Figure 4:
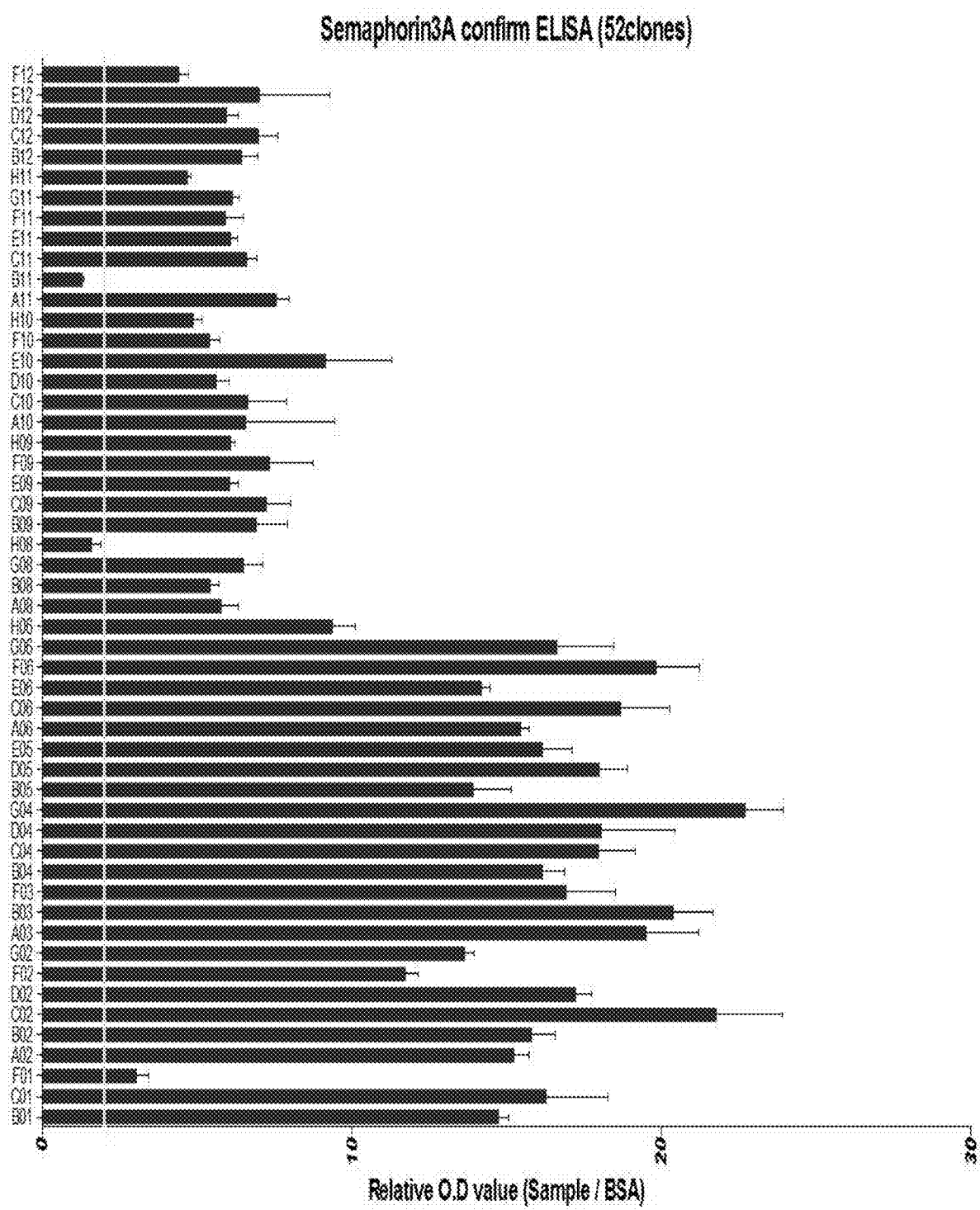
FIG. 4 shows results re-verifying binding abilities of 52 species of Sema3A scFv.

As a control group, the BSA solution was used, and among 52 clones, 31 clones having high binding affinities re-verified through ELISA were selected (FIG. 4).

After that, phagemid was collected from the 31 clones, and DNA sequence analysis thereof was performed. A total of 5 clones having different sequences were selected.

Figure 5A:
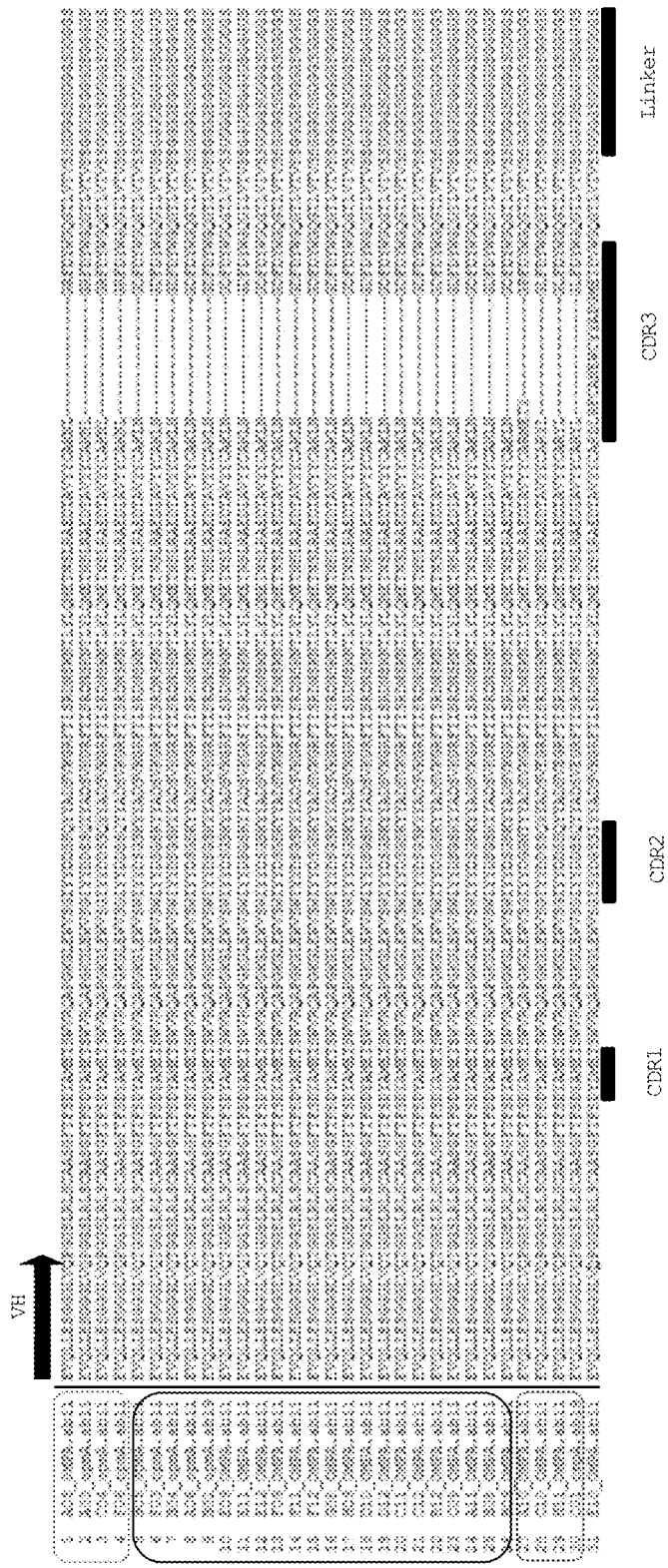
FIGS. 5a and 5b show results confirming the sequences of 31 species of Sema3A scFv.
Figure 5B:
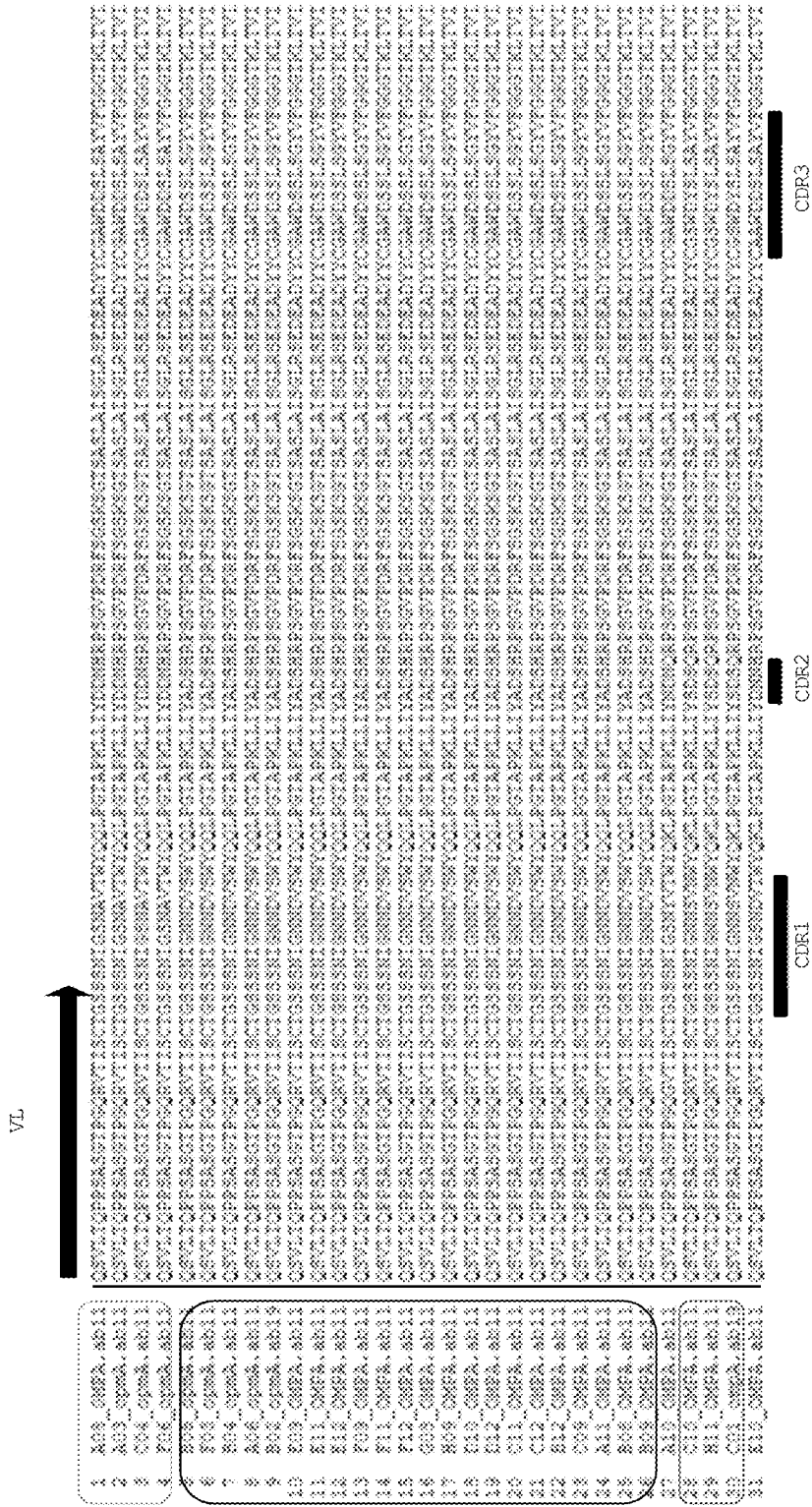

It was verified that three (3) A08 clones, twenty-one (21) F11 clones and two (2) C10 clones had identical DNA sequences, and additionally, A10 and E10 clones had different DNA sequences (FIG. 5).

In the order of increasing the number of clones with identical sequences, F11, A08 and C10 were selected as the final Seman3A scFv candidates.

EXAMPLE 3

Figure 6:
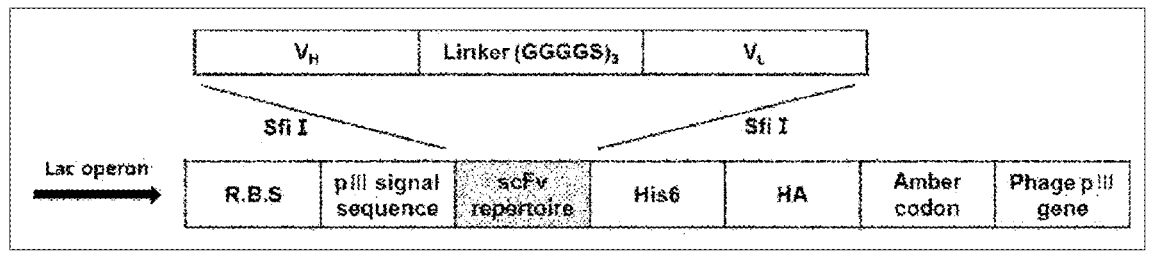
FIG. 6 is a diagram of phagemid vector for the production of scFv antibody fragments.

Production of Anti-Sema3A scFv Protein and Verification on Binding Affinity to Sema3A The basic structure of phagemid can be confirmed in FIG. 6, and in the case of the host cell ER2537 used in the above procedures, since it suppresses the transcription stop codon (amber codon (UAG)) located in front of the phage pIII, the expression of scFv alone is not possible therein.

Accordingly, by using the expression strain (TOP1OF'), which is a non-suppressor strain, the phagemid was transduced into the expression strain. After that, the expression strains into which respective phagemids were introduced without mutation were confirmed through DNA sequencing.

A colony was taken from the expression strains, and inoculated in 3 ml of LB/ampicillin media, followed by culturing overnight at 37° C.

After the culturing overnight, 3 ml of the culture solution was transferred to 400 ml of media (SB/ampicillin), and then further cultured until O.D600 reached 0.5-0.7. 1 mM IPTG as final concentration was added, followed by culturing overnight at 30° C. After the culture solution was centrifuged, the expression hosts were lysed in 40 ml of TES solution and then added with 60 ml of 0.2× TES, thereby collecting the phage particles in the periplasm. The collected supernatant was filtered through an 0.45 um filter.

For His-tag purification, the scFv proteins present in the filtered solution were added with 1 ml of Ni-NTA beads (Qiagen) and allowed to bind thereto at room temperature for 1 hour, and then Ni-NTA beads were packed in the gravity column (Bio-rad), followed by collecting scFv proteins using 200 mM imidazole solution.

Figure 7:
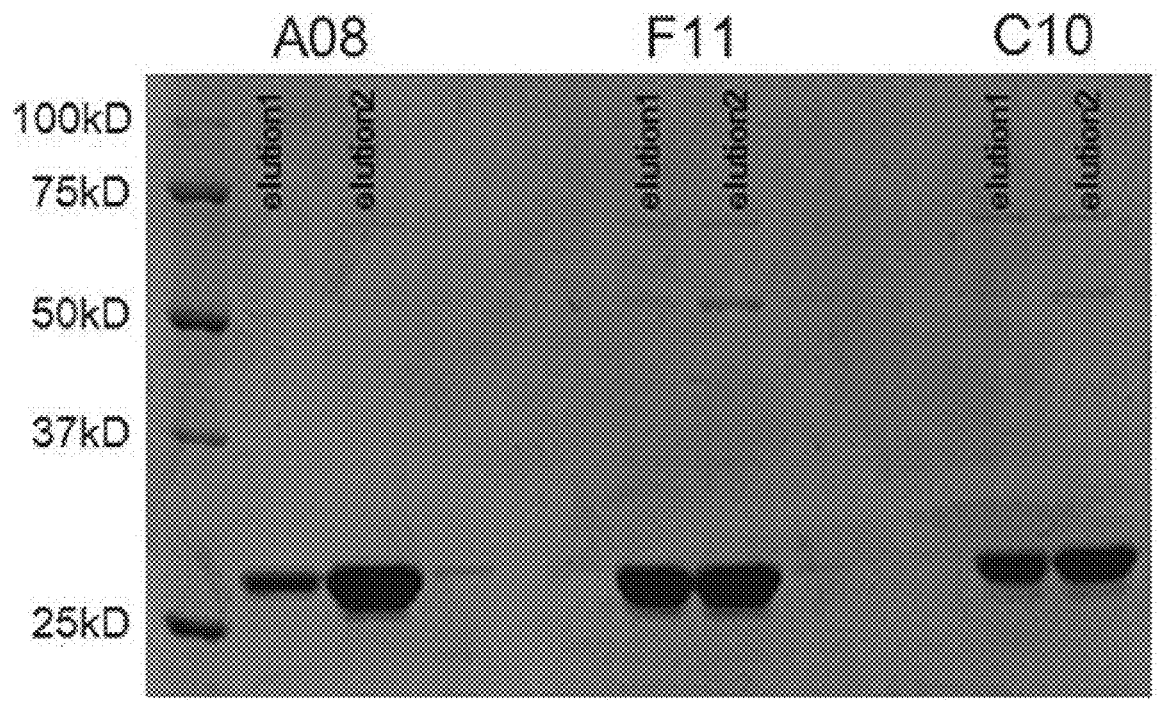
FIG. 7 shows Coomassie staining results of three species of purified Sema3A scFv antibody fragments.

Through SDS-PAGE and Coomassie blue staining after expression and purification of each clone, each scFv was verified to have a size of about 28 kDa, and the results were shown in FIG. 7.

The DNA sequences of each clone in the form of purified scFv are set forth in Table 1 and Table 2 below.

Sequence information on heavy chain FR and CDR regions of three anti-Sema3A scFv antibody fragments

TABLE 1

Sequence information on heavy chain FR and CDR regions of three anti-Sema3A scFv antibody fragments

| Antibody | SEQ ID NO | Name | Sequence |
| --- | --- | --- | --- |
| A08 | 25 | A08 heavy chain FR1 | EVQLLESGGGLVQPGGSLRLSCAAS |
|  | 1 | A08 heavy chain CDR1 | GFTFSDYA |
|  | 26 | A08 heavy chain FR2 | MSWVRQAPGKGLEWVSG |
|  | 2 | A08 heavy chain CDR2 | IYYDDSSQ |
|  | 27 | A08 heavy chain FR3 | YYADSVKGRFTISRDNSKNTLYLQMN SLRAEDTAVYYC |
|  | 3 | A08 heavy chain CDR3 | AKNLGRFDY |
|  | 28 | A08 heavy chain FR4 | WGQGTLVTVSS |
| C10 | 29 | C10 heavy chain FR1 | EVQLLESGGGLVQPGGSLRLSCAAS |
|  | 7 | C10 heavy chain CDR1 | GFTFSDYA |
|  | 30 | C10 heavy chain FR2 | MSWVRQAPGKGLEWVSG |
|  | 8 | C10 heavy chain CDR2 | IYYDDSSQ |
|  | 31 | C10 heavy chain FR3 | YYADSVEGRFTISRDNSKNTLYLQMN SLRAEDTAVYYC |
|  | 9 | C10 heavy chain CDR3 | ARYLGLFDY |
|  | 32 | C10 heavy chain FR4 | WGQGTLVTVSS |
| F11 | 33 | F11 heavy chain FR1 | EVQLLESGGGLVQTGGSLRLSCAAS |
|  | 13 | F11 heavy chain CDR1 | GFTFSDYA |
|  | 34 | F11 heavy chain FR2 | MSWVRQAPGKGLEWVSW |
|  | 14 | F11 heavy chain CDR2 | IYYDSGSK |

TABLE 1-continued

Sequence information on heavy chain FR and CDR regions of three anti-Sema3A scFv antibody fragments

| Antibody | SEQ ID NO | Name | Sequence |
| --- | --- | --- | --- |
|  | 35 | F11 heavy chain FR3 | YYADSVKGRFTISRDNSKNTLYLQMN SLRAEDTAVYYC |
|  | 15 | F11 heavy chain CDR3 | AKLNGDFDY |
|  | 36 | F11 heavy chain FR4 | WGQGTLVTVSS |

[Table 2]
Sequence information on light chain FR and CDR regions of three anti-Sema3A scFv antibody fragments

TABLE 2

Sequence information on light chain FR and CDR regions of three anti-Sema3A scFv antibody fragments

| Antibody | SEQ ID NO | Name | Sequence |
| --- | --- | --- | --- |
| A08 | 37 | A08 light chain FR1 | QSVLTQPPSASGTPGQRVTISCTGS |
|  | 4 | A08 light chain CDR1 | SSNIGSNA |
|  | 38 | A08 light chain FR2 | VTWYQQLPGTAPKLLIY |
|  | 5 | A08 light chain CDR2 | DDN |
|  | 39 | A08 light chain FR3 | HRPSGVPDRFSGSKSGTSASLAISGLR SEDEADYYC |
|  | 6 | A08 light chain CDR3 | GAWDDSLSAYV |
|  | 40 | A08 light chain FR4 | FGGGTKLTVL |
| C10 | 41 | C10 light chain FR1 | QSVLTQPPSASGTPGQRVTISCSGS |
|  | 10 | C10 light chain CDR1 | SSNIGNNS |
|  | 42 | C10 light chain FR2 | VNWYQQLPGTAPKLLIY |
|  | 11 | C10 light chain CDR2 | SDS |
|  | 43 | C10 light chain FR3 | QRPSGVPDRFSGSKSGTSASLAISGLR SEDEADYYC |
|  | 12 | C10 light chain CDR3 | GSWDYSLSAYV |
|  | 44 | C10 light chain FR4 | FGGGTKLTVL |
| F11 | 45 | F11 light chain FR1 | QSVLTQPPSASGTPGQRVTISCSGS |
|  | 16 | F11 light chain CDR1 | SSNIGNND |
|  | 46 | F11 light chain FR2 | VSWYQQLPGTAPKLLIY |
|  | 17 | F11 light chain CDR2 | ADS |
|  | 47 | F11 light chain FR3 | HRPSGVPDRFSGSKSGTSASLAISGLR SEDEADYYC |
|  | 18 | F11 light chain CDR3 | GAWDSSLSGYV |
|  | 48 | F11 light chain FR4 | FGGGTKLTVL |

To determine the binding affinity to human Sema3A according to concentrations of the respective antibody protein fragments, in each 96 well coated with 200 ng of Sema3A and BSA, each scFv was treated with concentrations of 2,000 ng/ml, 1,000 ng/ml, 500 ng/ml, 250 ng/ml, 125 ng/ml, 62.5 ng/ml, 31.25 ng/ml and 15.62 ng/ml to analyze changes in the OD values.

Figure 8:
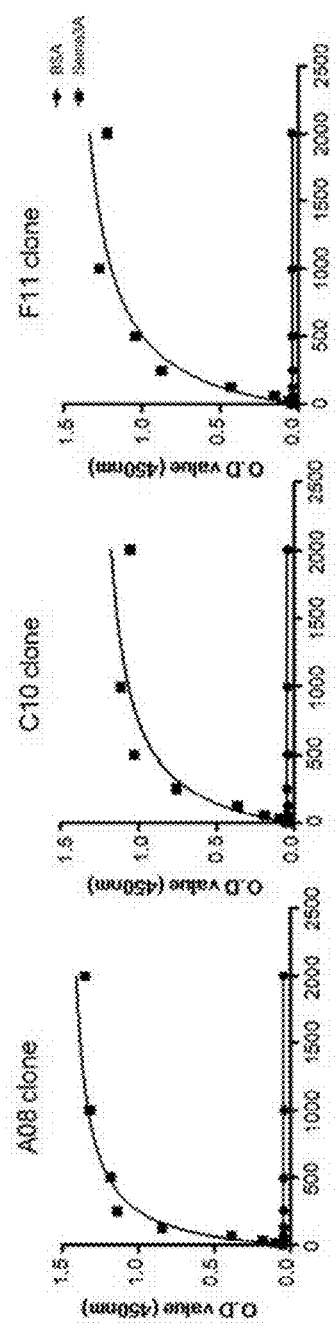
FIG. 8 is a graph showing Indirect ELISA results according to concentrations with respect to three species of anti-Sema3A scFv antibody fragment.

In the case of A08, C10 and F11 scFv, it can be confirmed by changes in the OD values that the size of the binding affinities of scFv to Sema3A increases as the concentration increases, compared to BSA, and this can be confirmed in FIG. 8.

EXAMPLE 4

Verification on Abilities of Anti-Sema3A scFv to Inhibit Cell Growth and Cell Migration The binding affinities to Sema3A proteins were verified by ELISA, and then the cell proliferation assay and the cell migration assay were used in order to verify the anti-cancer abilities to Sema3A, which is substantially secreted by cells.

Figure 9:
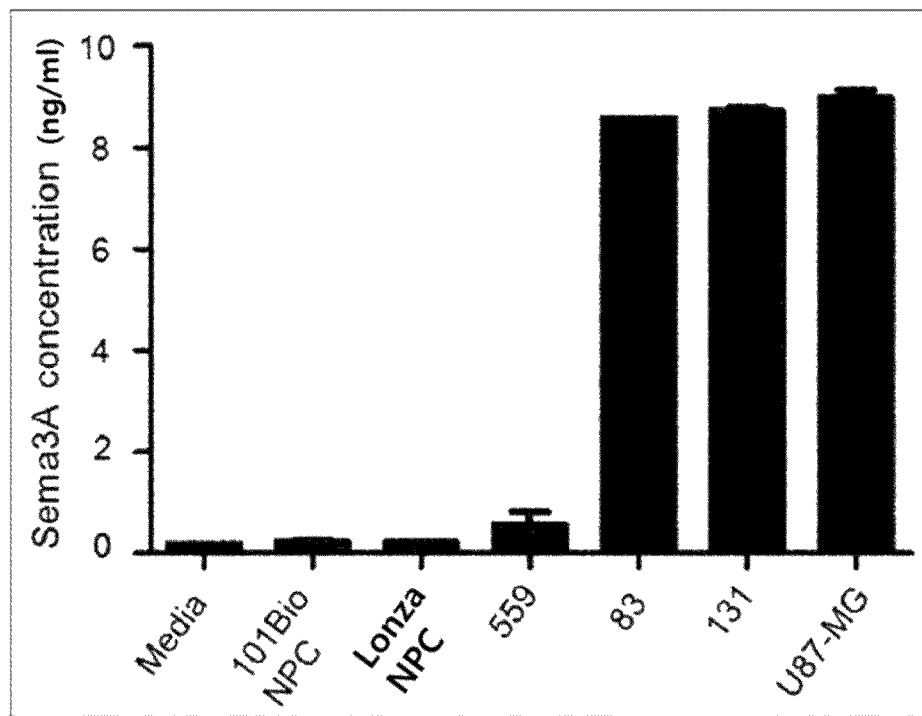
FIG. 9 shows results confirming Sema3A-secreting cells using Sandwich ELISA.

First, the secretion of Sema3A was verified by Sandwich ELISA. As a result, it was verified that, among the patient-derived cells, 559 secreted less Sema3A, whereas 131 and 83 hyper-secreted Sema3A. The media and NPC were used as negative controls and U87-MG cells were used as a positive control (FIG. 9).

In order to perform the cell proliferation assay, $5 \times 10^3$ cells of 559 and 131 were treated with 50 ug/ml of anti-Sema3A scFv. The cell growth rate was measured using the EZ-Cytox cell viability assay kit (Daeil Lab. Service) on day 4 after the treatment.

Figure 10:
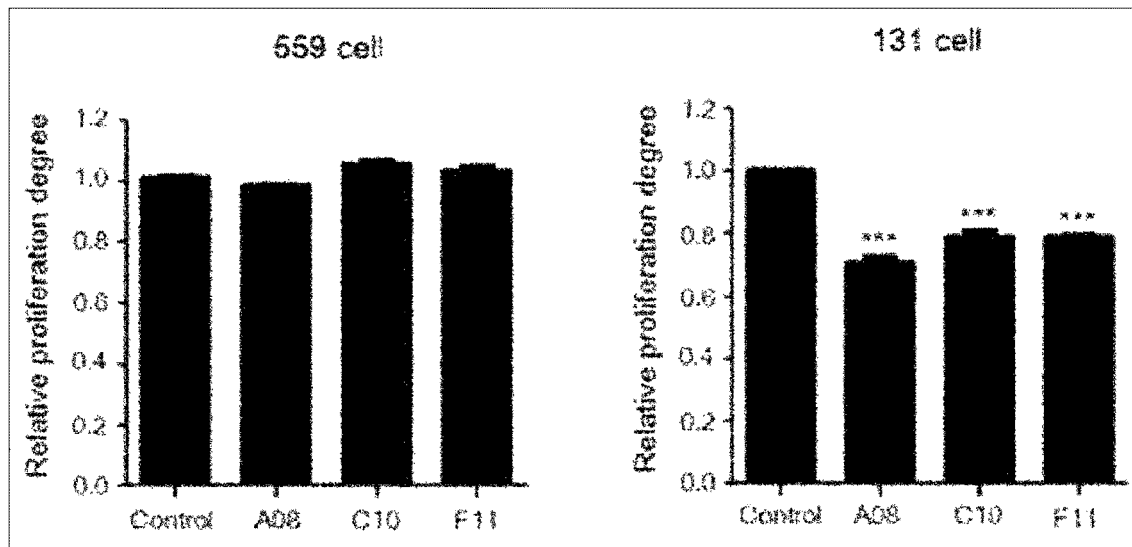
FIG. 10 shows results confirming the abilities to inhibit cell growth using anti-Sema3A.

559 cells secreting less Sema3A showed no change in the cell growth rate after anti-Sema3A scFv treatment, whereas 131 cells hypersecreting Sema3A showed 70% of the cell growth rate after anti-Sema3A scFv treatment as compared to the control group (FIG. 10).

In order to verify the abilities to inhibit cell migration using anti-Sema3A scFv, the cell migration assay was performed using U87-MG, 131 and 83 cells which are Sema3A-hypersecreting cells.

First, PLO(Poly-L-Ornithine) was added to a transwell (Corning) and coated at room temperature for 30 minutes, followed by air-drying. For U87-MG cells, $5 \times 10^4$ U87-MG cells and 50 ug/ml of three species of Sema3A scFv were added to 100 ul of DMEM media without growth factor, and the solution was added to a transwell. 600 ul of DMEM culture solution containing 10% FBS (fatal bovine serum) was added to the bottom well and cultured overnight at 37° C. For 131 and 83 cells which are the patient-derived cells, $1 \times 10^5$ cells and three species of Sema3A scFv were respectively added to 100 ul NBA culture solution not containing the growth factor (EGF and bFGF), and NBA culture solution containing the growth factor was added to the bottom well and cultured overnight at 37° C.

Then, 600 ul of methanol, hematoxylin and eosin were prepared for one per transwell in a 12-well, and then the transwell was kept in methanol for one minute and then allowed to stand in hematoxylin for 5 minutes to stain the nuclei.

Next, after washing with water and wiping moisture off, the resultant was kept in eosin for 30 seconds to stain cytoplasm. It was again washed with water and wiped cleanly inside the transwell with a cotton swab. It can be observed from FIG. 11 that the nucleus was stained by hematoxylin and the cytoplasm was stained by eosin.

Figure 11:
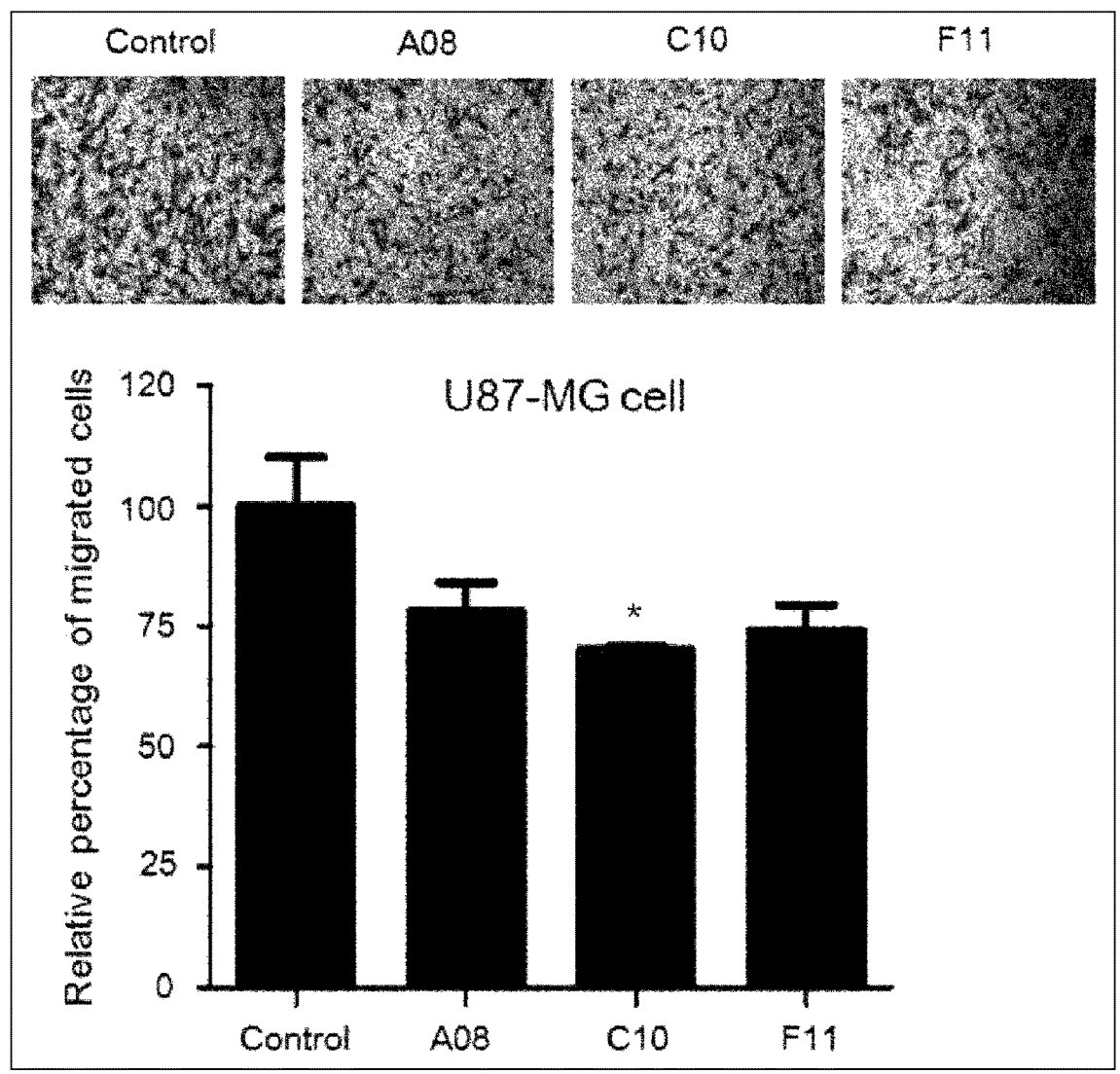
FIG. 11 shows results confirming the abilities to inhibit cell migration using anti-Sema3A scFv and U87-MG cells.

For U87-MG cells, when cell migration of a control not treated with Sema3A scFv antibodies was regarded as 100%, cell migration of cell with A08 anitbody frgment was reduced to 78%, with C10 antibody fragment to 70%, with F11 antibody fragment to 74% (FIG. 11).

Figure 12:
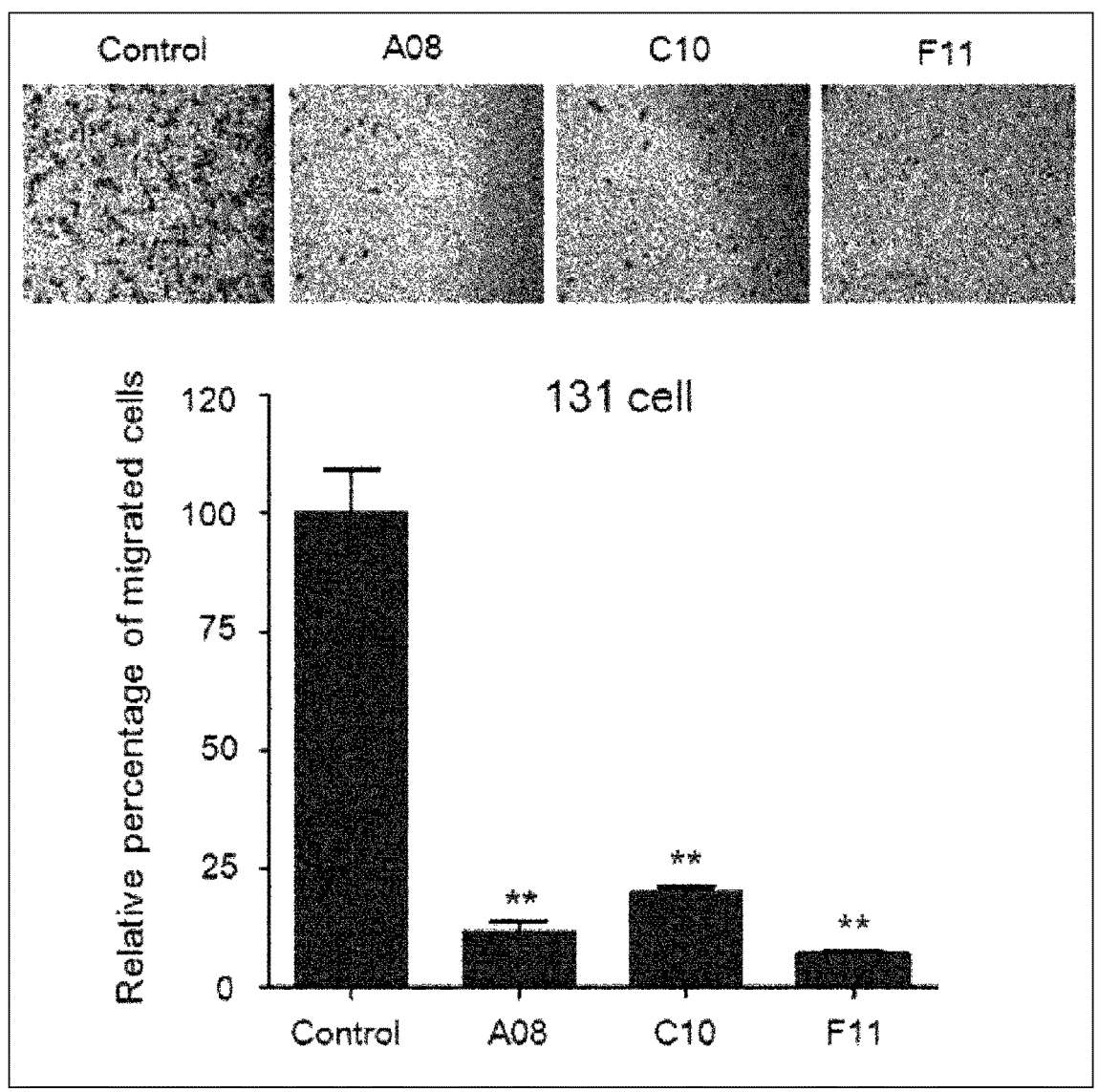
FIG. 12 shows results confirming the abilities to inhibit cell migration using anti-Sema3A scFv and 131 cells.
Figure 13:
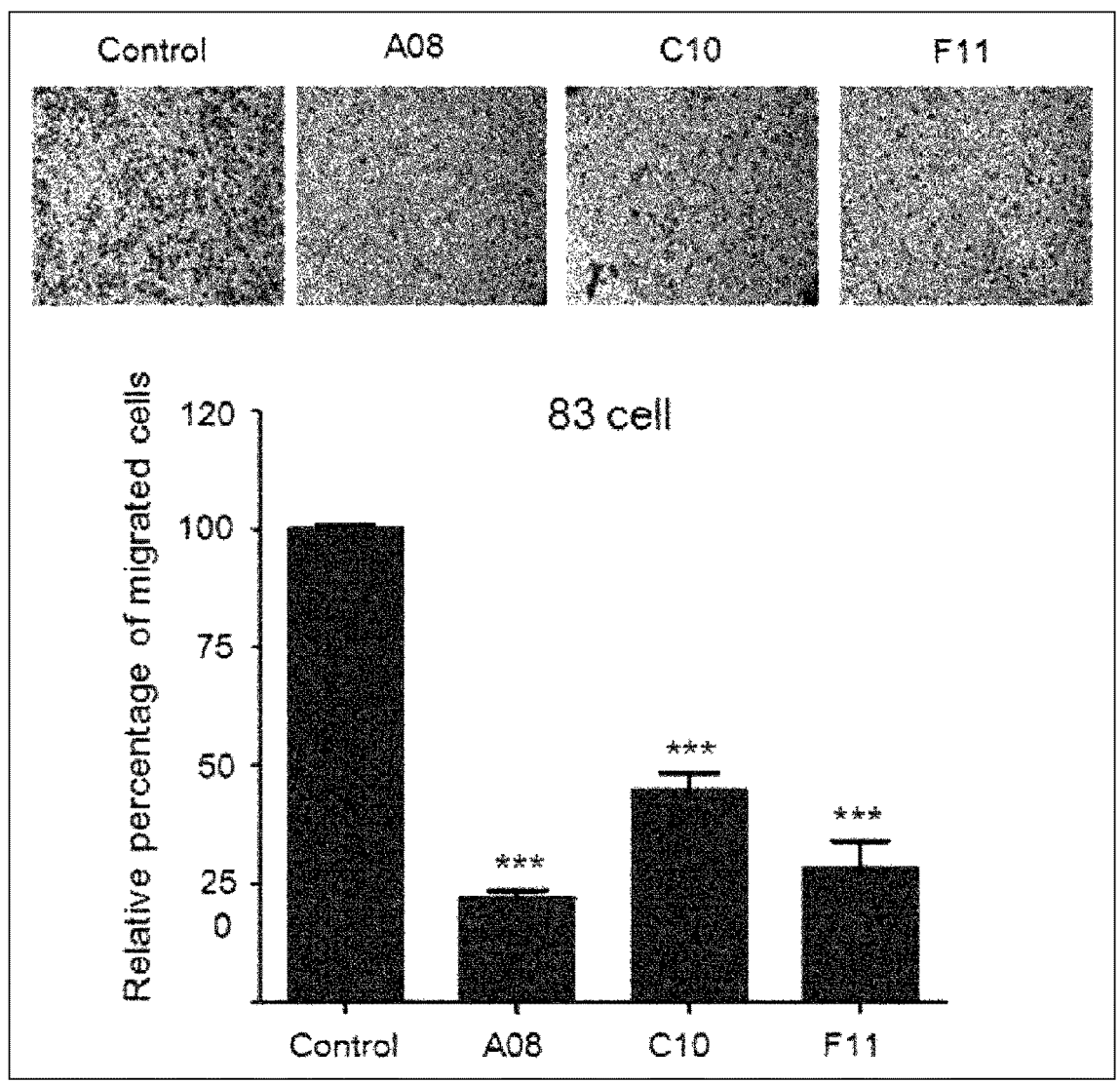
FIG. 13 shows results confirming the abilities to inhibit cell migration using anti-Sema3A scFv and 83 cells.
Figure 14A:
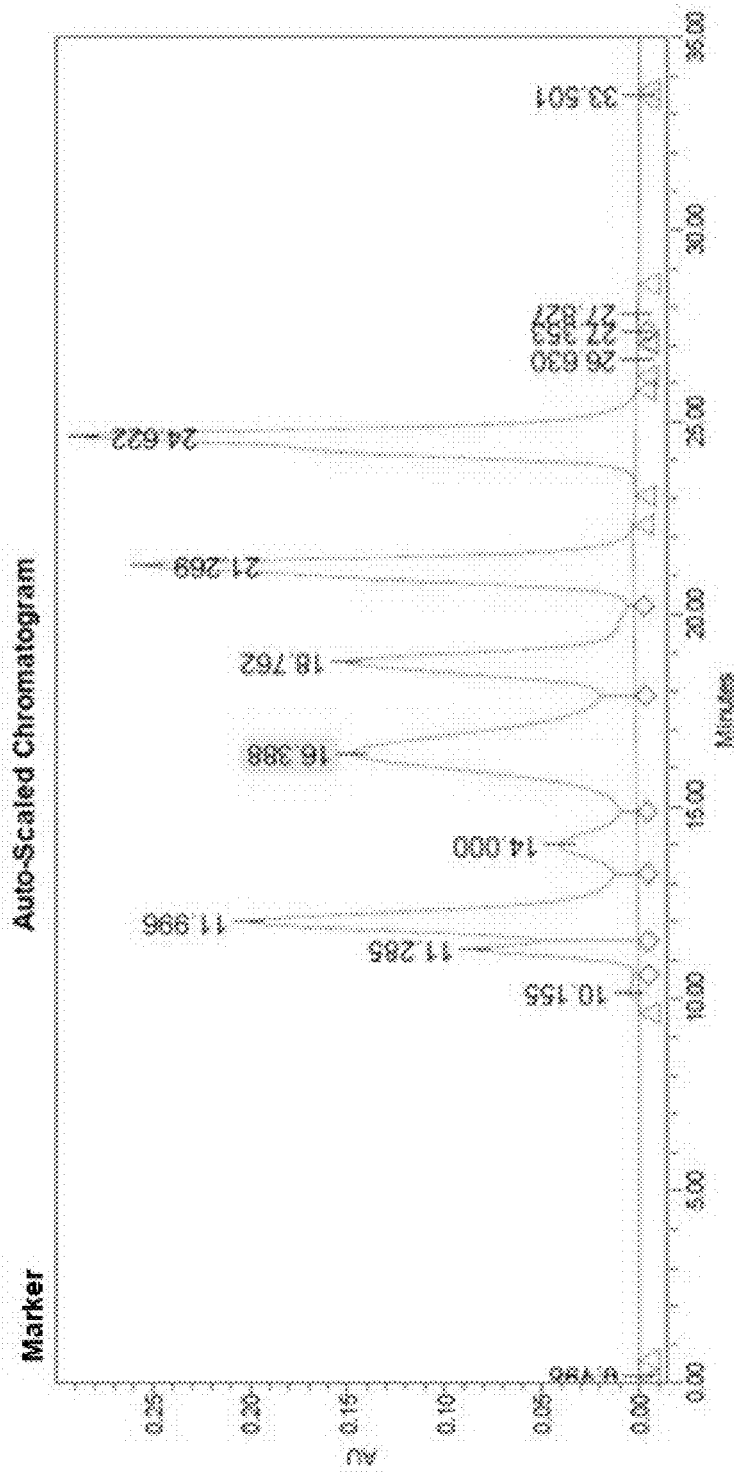
FIGS. 14a, 14b, 14c and 14d show results confirming the purity of anti-Sema3A IgG by HPLC analysis.
Figure 14B:
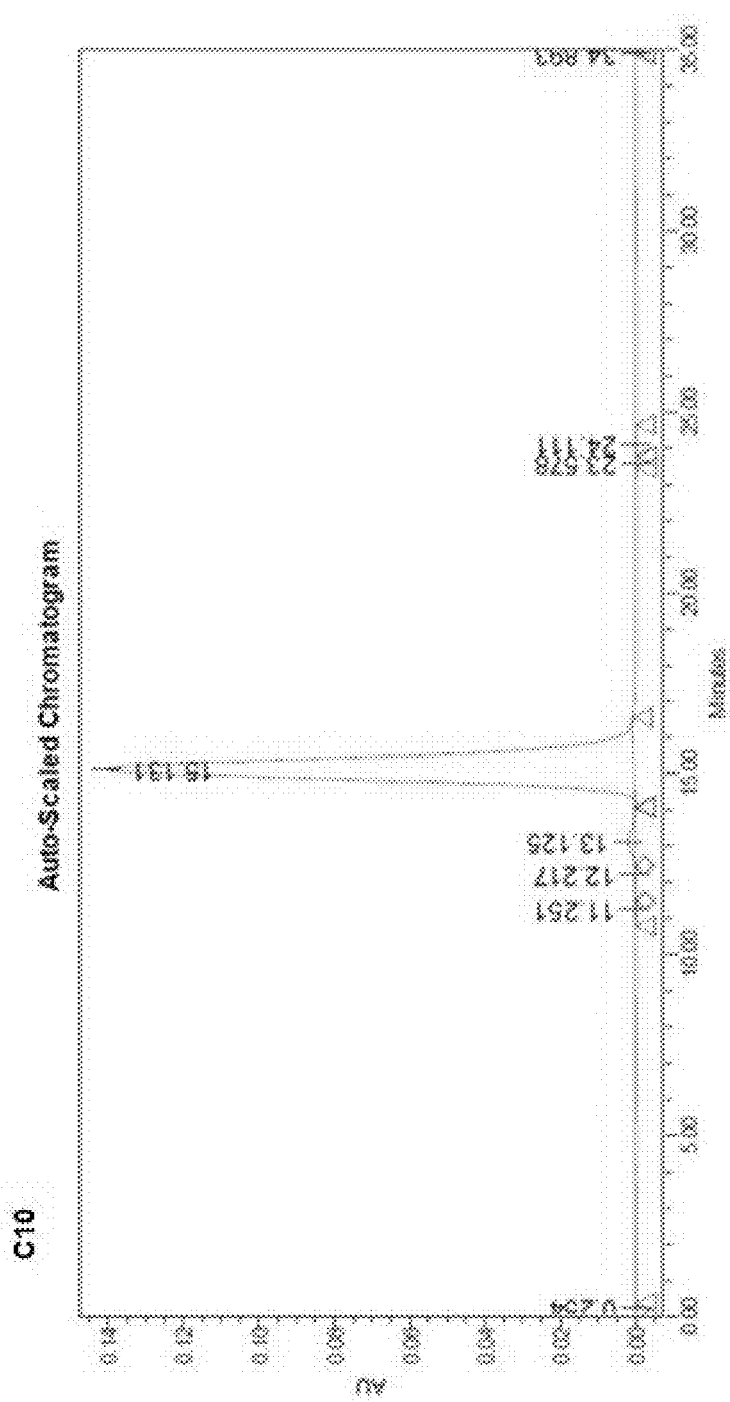
Figure 14C:
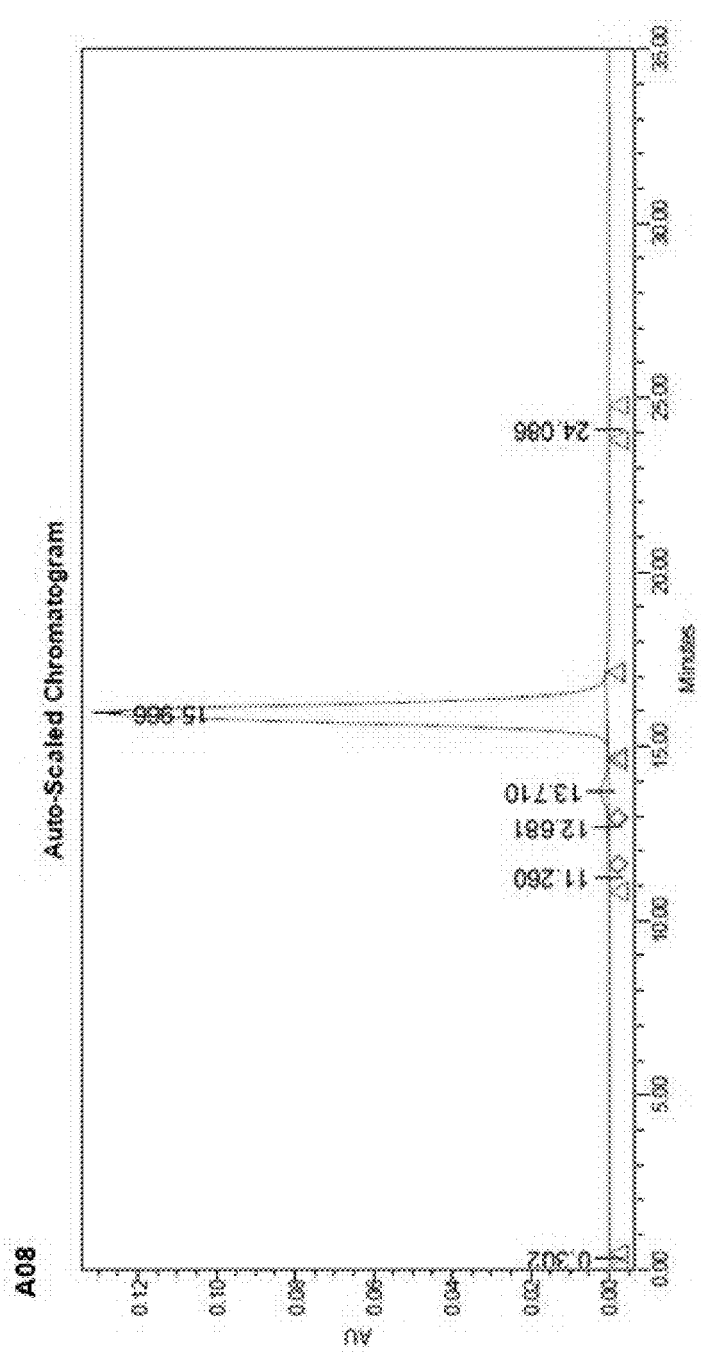
Figure 14D:
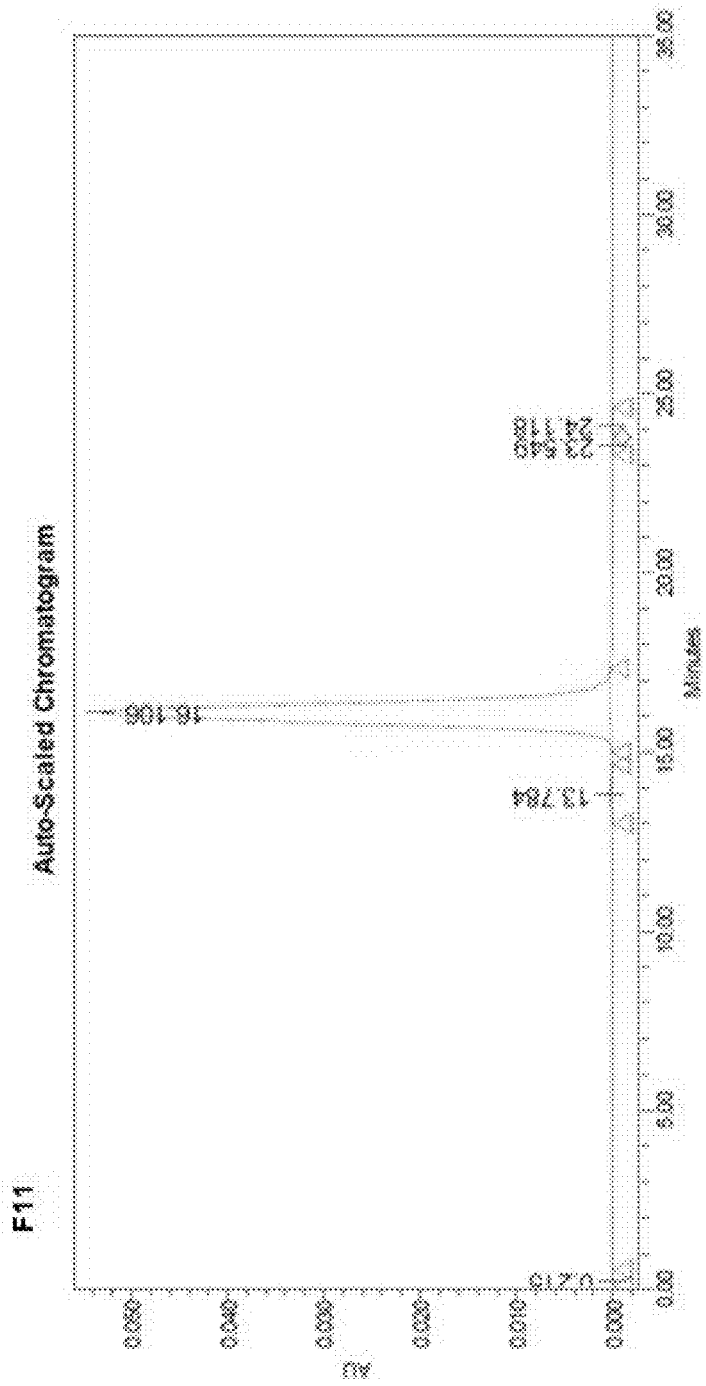

For patient-derived cells, 131 and 83, cell migration of a cell treated with A08 antibody fragment was reduced to 11% and 21%, with C10 antibody fragment to 19% and 44%, and F11 antibody fragment to 7% and 28%, respectively (FIGS. 12 and 13).

Three species of Sema3A antibody fragments exhibited a higher effect of inhibiting the cell migration in 131, 83 cells (patient-derived cells) than in cell line U87-MG, which showed the potential as an anti-cancer agent to inhibit cell migration of cancer cells.

EXAMPLE 5

Production of IgG from Anti-Sema3A Antibody Fragment

For the conversion of anti-Sema3A antibody fragment into forms of IgG, the genes of the heavy chain sequences and light chain sequences of scFv Sema3A were transfected using Expi 293F expression system (life technologies).

In order to obtain Sema3A IgG in the culture solution, the purification was performed using ÄKTA protein purification system and Amicon centrifugal filter. The production amount was 118 mg/L for A08, 138 mg/L for C10 and 330 mg/L for F11.

In order to confirm the purity of the purified anti-Sema3A antibody, the high performance liquid chromatography was introduced. Since the size of IgG is 150 kD, it corresponds to the material eluted from the marker peak at 16.388 minutes.

It was confirmed that three species of Sema3A antibodies (A08, C10 and F11) were detected from this peak and the purity was 98%, 98.5% and 99%, respectively.

Figure 15:
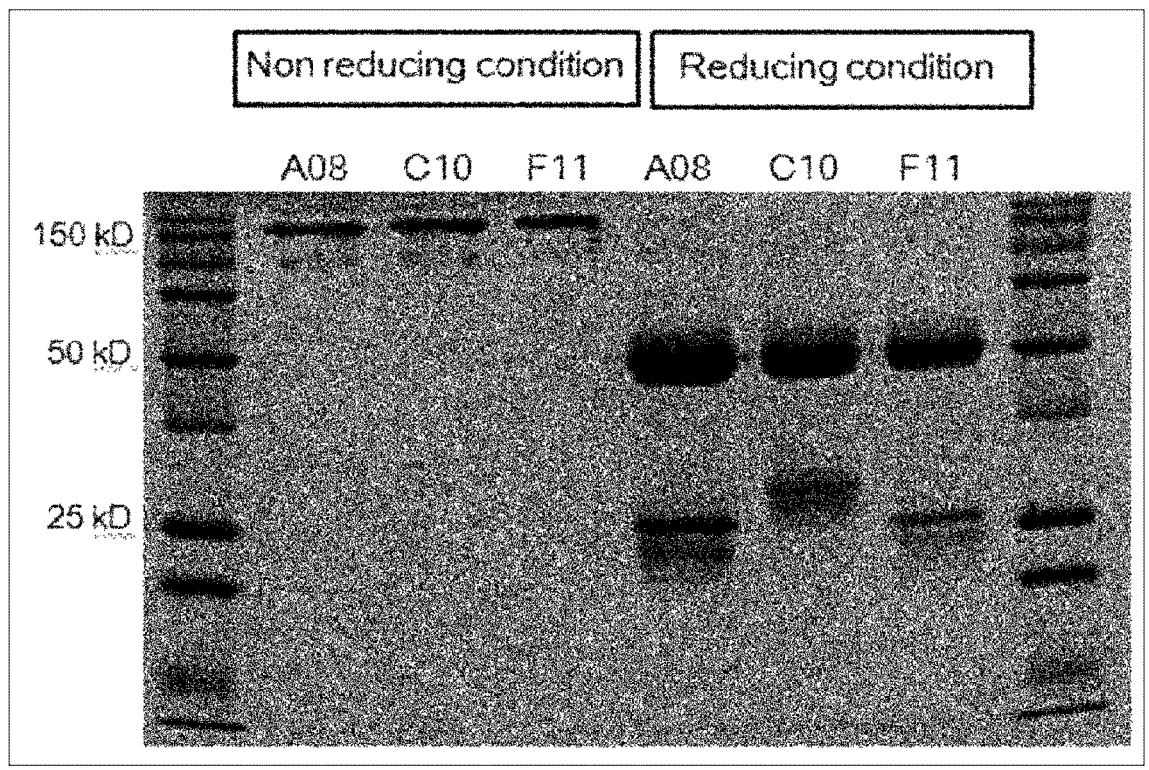
FIG. 15 shows results confirming the size of anti-Sema3A IgG by Coomassie staining.

The forms of anti-IgG Sema3A according to the sizes were confirmed through SDS PAGE and Coomassie staining. Under non-reducing conditions, a band was detected at 150 kD which is the size of IgG, and under reducing conditions, the disulfide bond was broken and thus, the sizes of the heavy chain sequence and the light chain sequence were shown to be 50 kD and 25 kD, respectively (FIG. 15).

In order to confirm the binding affinity of three Sema3A antibodies to Sema3A, ELISA was performed under two concentration conditions (500 nM, 50 nM). BSA was used as a negative control, and mouse Sema3A and human Sema3A proteins were used as an experimental group.

Figure 16:
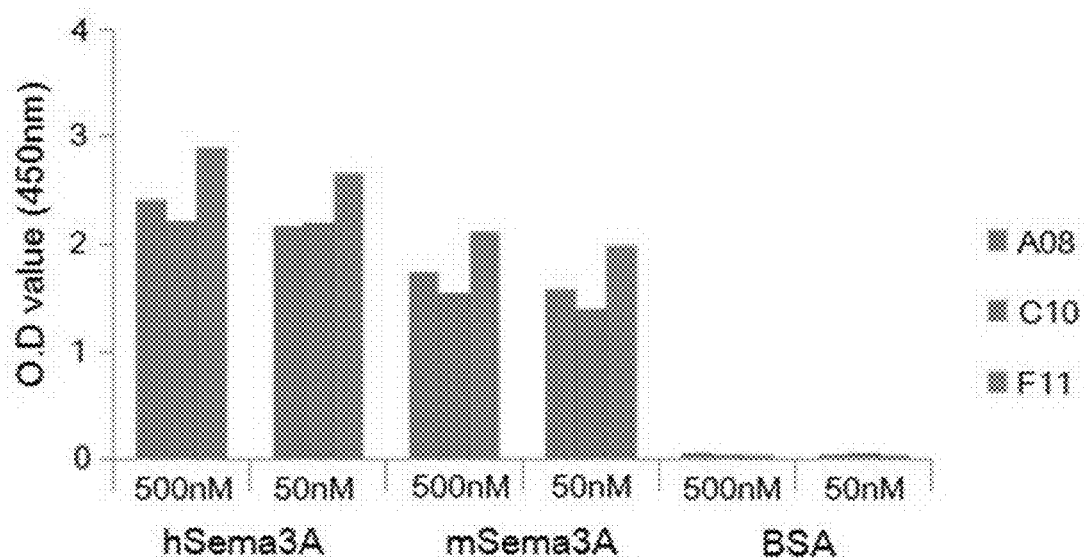
FIG. 16 shows results confirming binding abilities of antibodies to human and mouse Sema3A.
Figure 17A:
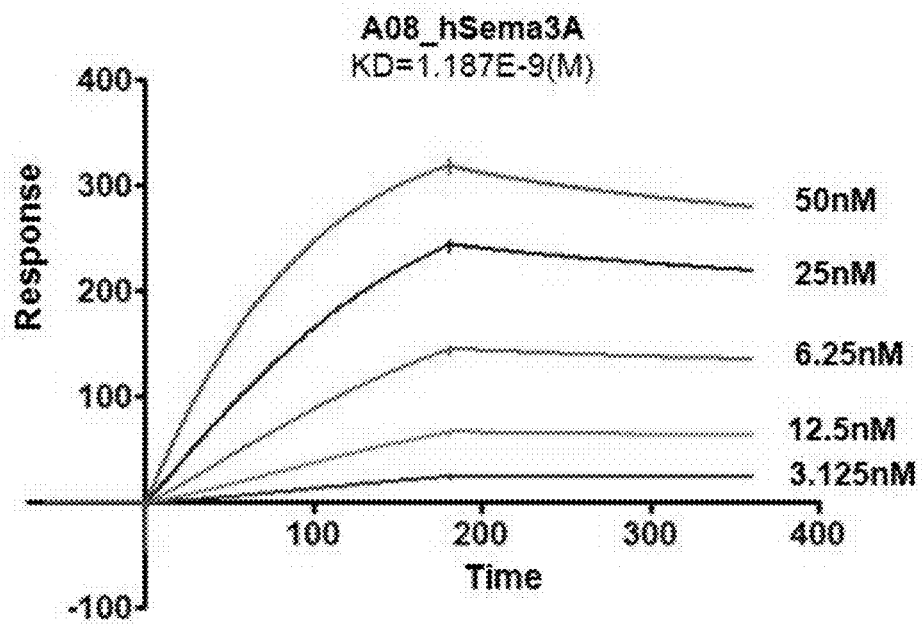
FIGS. 17a, 17b, 17c, 17d, 17e and 17f show the results of SPR analysis on binding abilities of three species of anti-Sema3A IgG to human and mouse Sema3A.
Figure 17B:
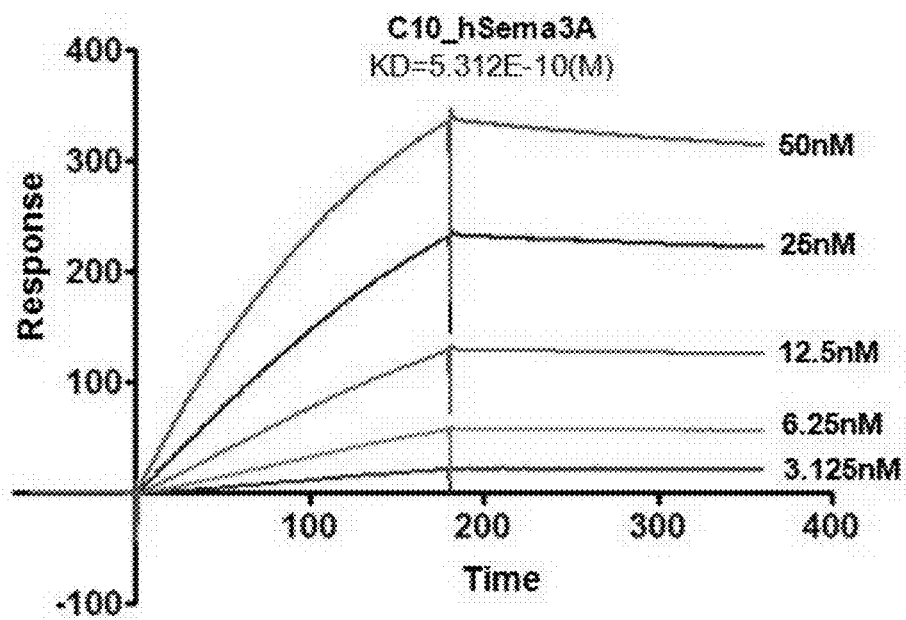
Figure 17C:
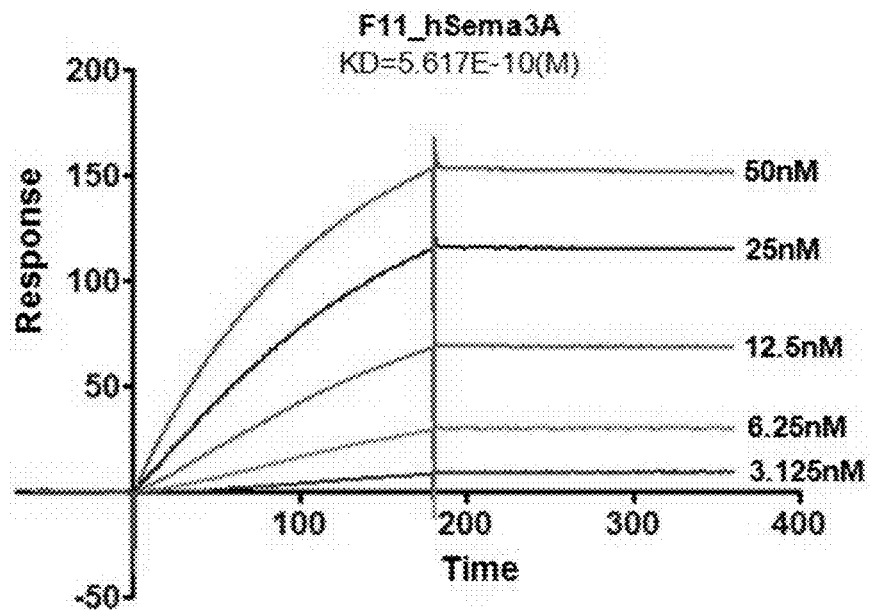
Figure 17D:
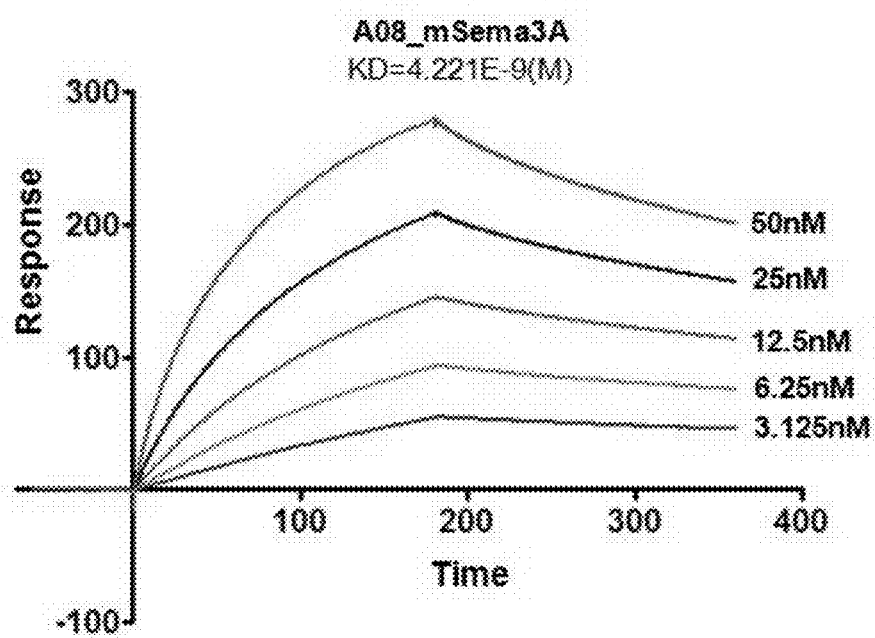
Figure 17E:
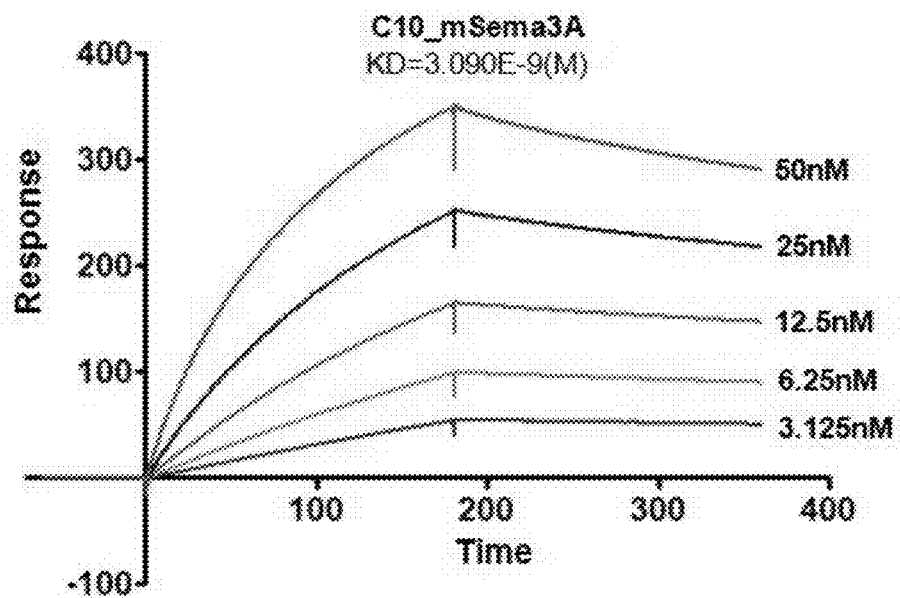
Figure 17F:
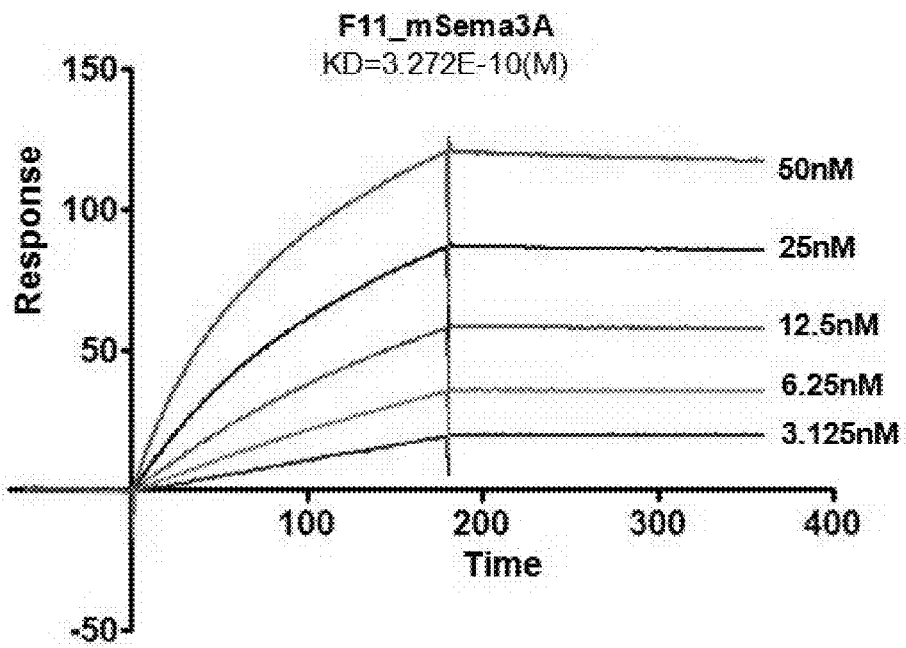

It was confirmed that three species of Sema3A antibodies have biding affinities to human Sema3A and mouse Sema3A, which can be seen in FIG. 16. The reason why the present antibody has a binding affinity to mouse Sema3A in addition to human Sema3A was assumed that the proteins have a low specificity between the species compared to other proteins and thus, the sequence homology between the human Sema3A and mouse Sema3A is 98% or more. Therefore, it is considered that the antibody has cross-linking abilities to human Sema3A and mouse Sema3A (FIG. 16).

In order to measure the binding affinities of three anti-Sema3A antibodies to human Sema3A and mouse Sema3A, SPR analysis was performed using Biacore system.

The measurement results showed that the binding affinities to human Sema3A were A08 (KD=1.187E-9), C10 (KD=5.312E-10), and F11 (KD=5.617E-10), and the binding affinities to mouse Sema3A were A08 (KD=4.221E-9), C10 (KD=3.090E-9), and F11 (KD=3.272E-10).

Accordingly, it was confirmed that three anti-Sema3A antibodies showed cross-reactivity, and particularly F11 showed the highest binding affinities to human Sema3A and mouse Sema3A (FIG. 17).

EXAMPLE 6

Verification on Abilities of Anti-Sema3A IgG to inhibit cell migration

As previously verifying abilities of anti-Sema3A scFv to inhibit cancer cell migration, the abilities of three Sema3A antibodies (A08, C10 and F11) converted to IgG forms to inhibit cancer cell migration were re-verified. Cell migration assay was performed using U87-MG, 131 and 83 cells hypersecreting Sema3A, and 2 ug/ml of anti-Sema3A antibodies. Cell migration assay was performed by the methods such as those shown in FIG. 11 through FIG. 13 as previously described.

Figure 18:
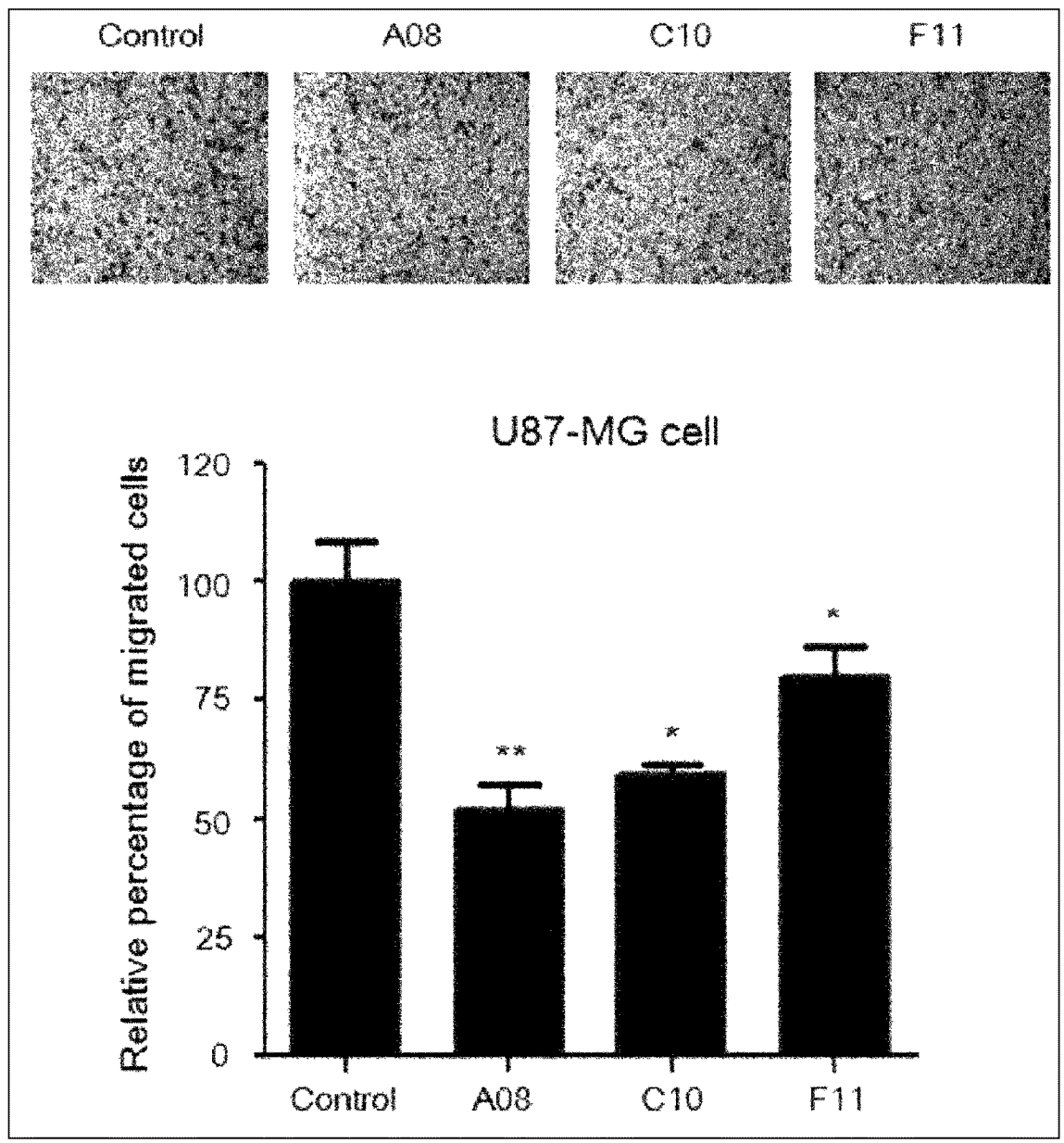
FIG. 18 shows the results confirming the abilities to inhibit cell migration using anti-Sema3A IgG and U87-MG cells.
Figure 19:
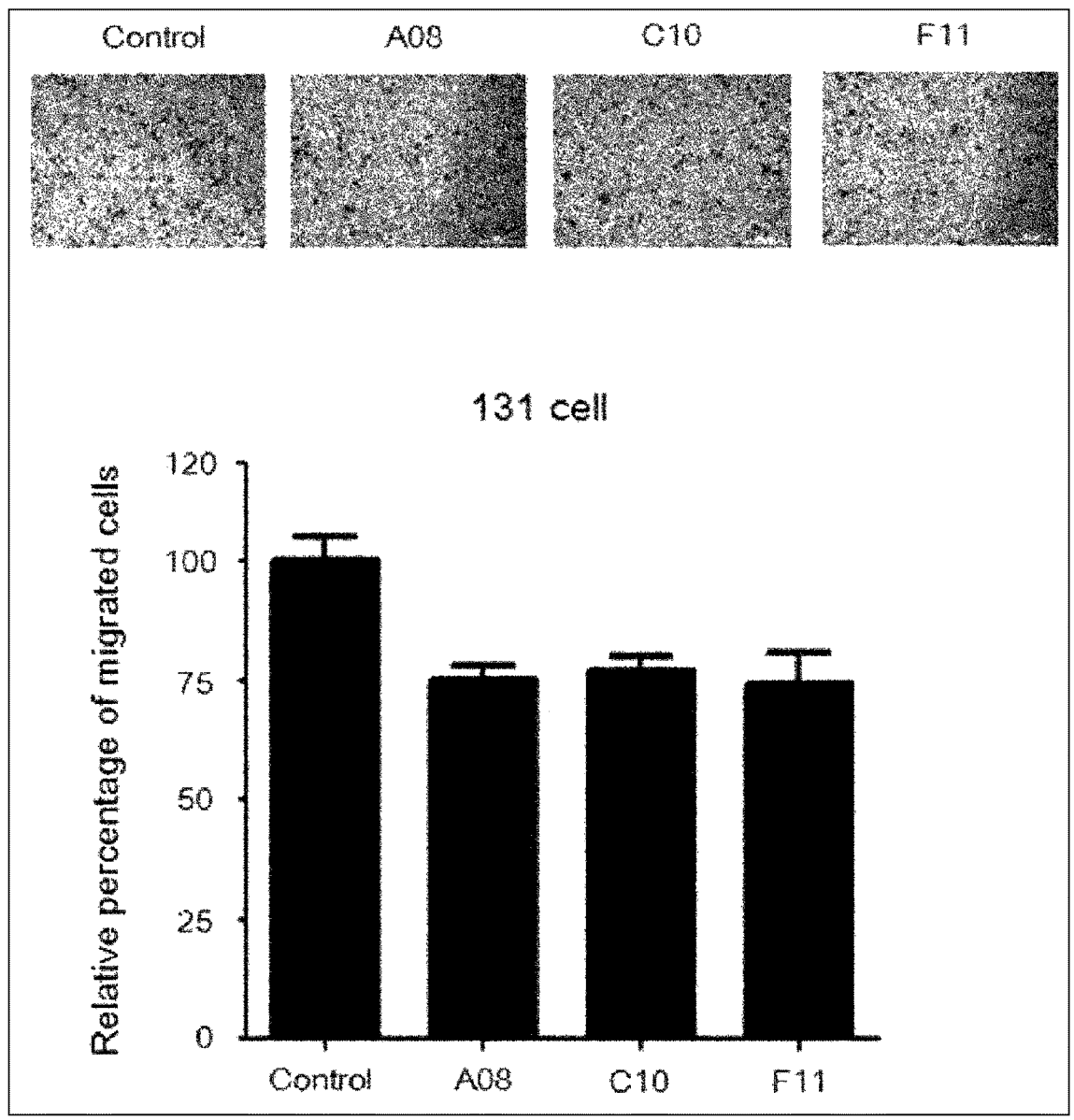
FIG. 19 shows the results confirming the abilties to inhibit cell migration using anti-Sema3A IgG and 131 cells.
Figure 20:
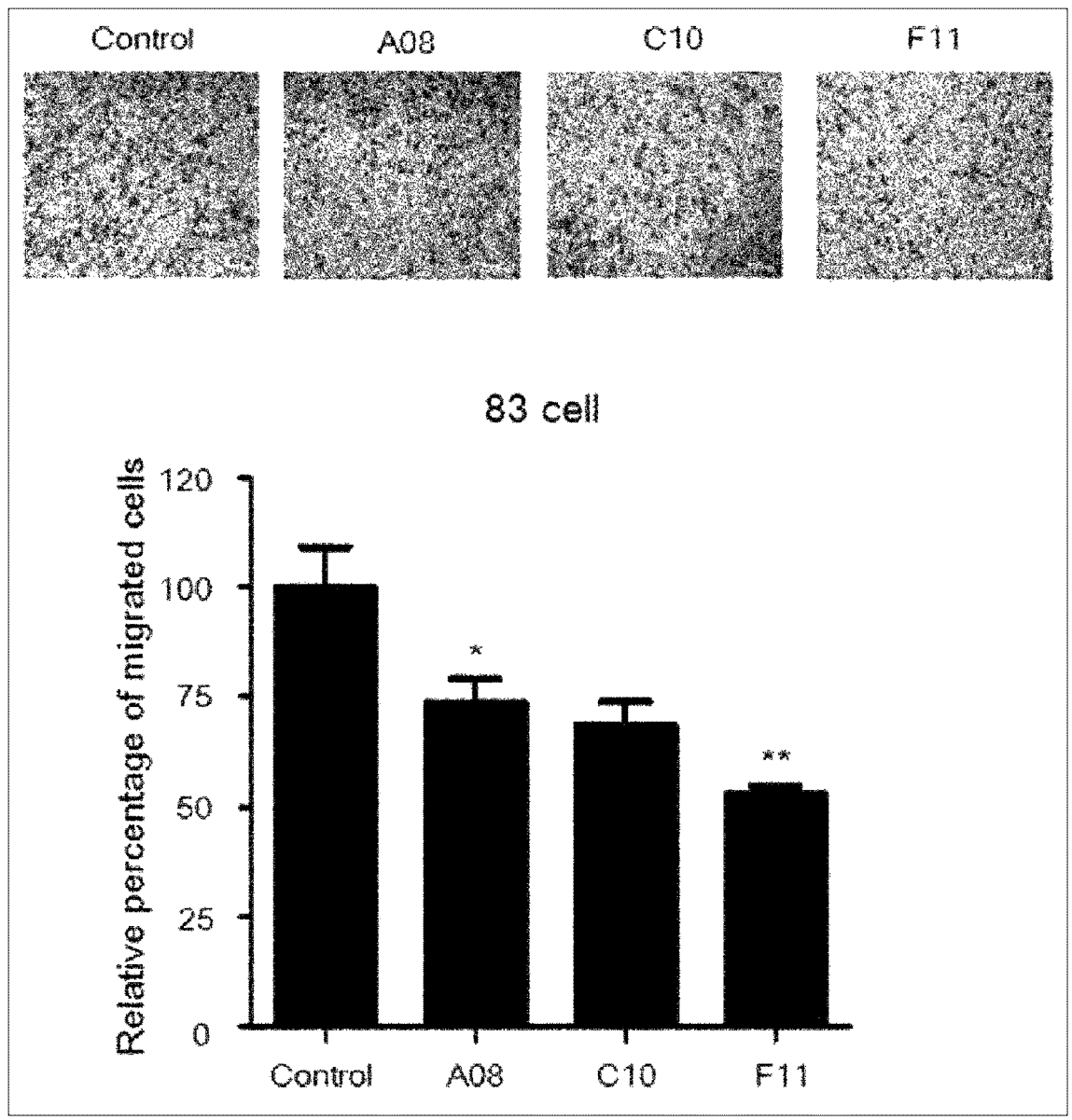
FIG. 20 shows the results confirming the abilities to inhibit cell migration using anti-Sema3A IgG and 83 cells.

For U87-MG cells, A08 exhibited the highest abilities to inhibit cell migration with 50% (FIG. 18), and for 131 and 83 cells, F11 was the most effective which showed lower levels of cell migration with 74% and 52% respectively, compared to the control (FIGS. 19 and 20).

Studies that ERK signal mechanism is associated with cell migration in which Sema3A is involved in colorectal cancer (Neufeld, G et al., Cold Spring Harbor perspectives in medicine,2012) and that Sema3A is involved in Rho/ROCK signal mechanism and ERK signal mechanism in glioblastoma (Zohrabian, V. M., Anti-cancer research, 119-123, 2009) have been reported.

$1 \times 10^6$ cells of 83 cells were treated with F11(50 ug/ml) for 30 minutes at 37° C., followed by performing Western Blotting to confirm whether the antibody can inhibit ERK phosphorylation or not. SDS-PAGE protein electrophoresis on 8% gel was carried out, and p-ERK, ERK and -actin were probed with the antibodies.

Figure 21:
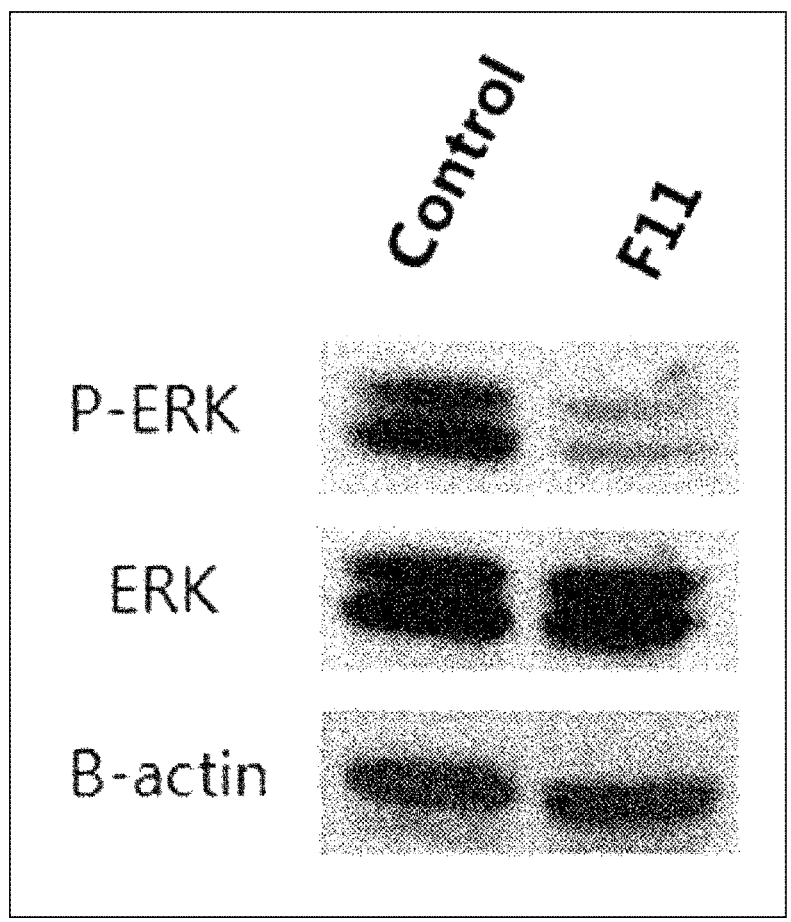
FIG. 21 shows the results confirming the efficacy of anti-Sema3A antibody that inhibits ERK phosphorylation.

The results of comparison of the control group and the experimental group with F11 treatment showed that ERK and B-actin were not changed, and ERK phosphorylation was reduced (FIG. 21).

Thus, it was confirmed that anti-Sema3A antibody inhibited cell migration by inhibiting the Phosphorylation of ERK among downstream signaling molecules of Sema3A.

EXAMPLE 7

Verification on Abilities of Anti-Sema3A IgG to Inhibit Cell Growth

Figure 22:
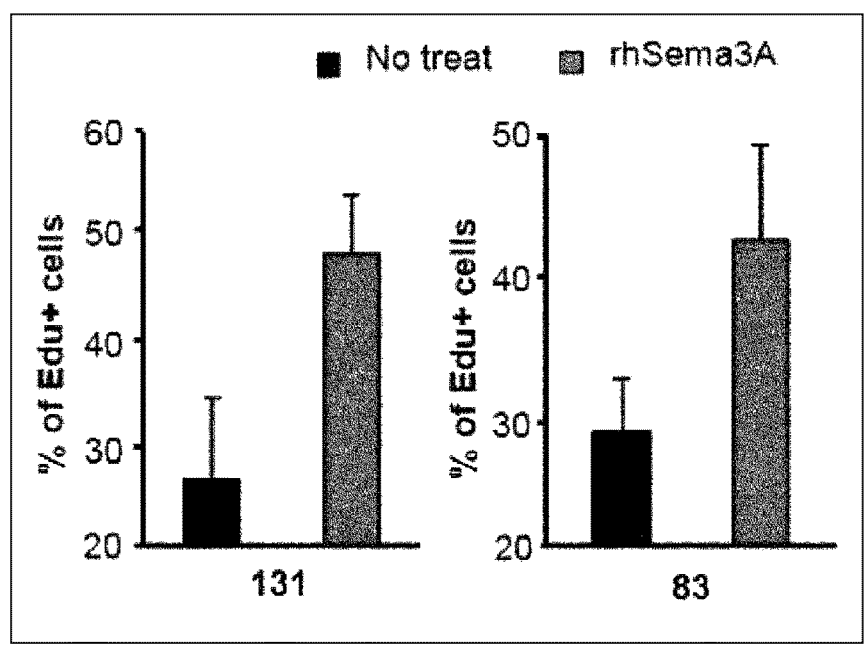
FIG. 22 shows the results confirming the abilities to promote the growth of glioblastoma cells in Sema3A IgG.

Recombinant human Sema3A was treated with 131 and 83 cells followed by observing the changes of cell growth to find out whether Sema3A was involved in cell growth of glioblastoma. As the results of cell proliferation assay using Edu, it was confirmed that the cell growth was increased by 20% and 15% in 131 and 83 cells, respectively (FIG. 22).

Figure 23:
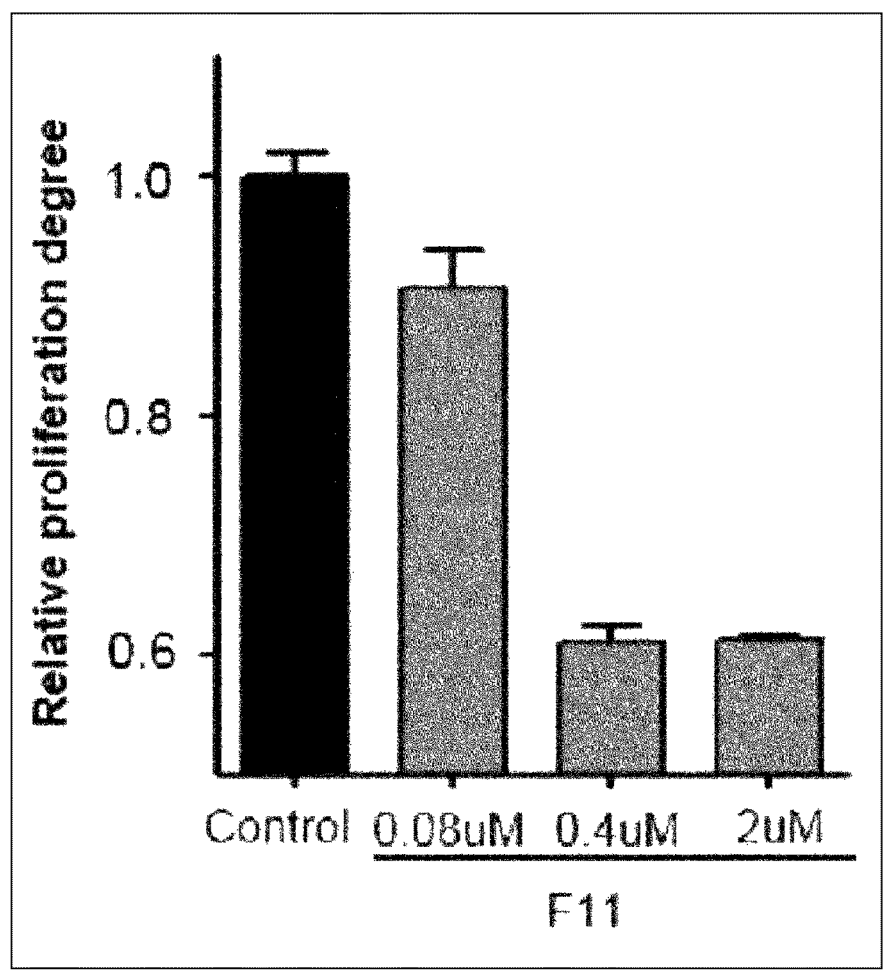
FIG. 23 shows the measurement results on the degree of inhibition of cell proliferation according to concentrations of anti-Sema3A IgG.

Then, As the results of F11 treatment to 131 cells, it was confirmed that the cell growth was inhibited depending on the concentration of antibody, and the inhibited cell growth to 40% compared to the control was observed at the highest concentration (2uM) of antibody (FIG. 23).

EXAMPLE 8

Assessment on Efficacies of Anti-Sema3A IgG with 131 Subcutaneous Model

To confirm anti-cancer efficacy of anti-Sema3A F11 in vivo, a xenograft model was constructed using gliobalstoma 131 cells hypersecreting Sema3A.

Figure 24:
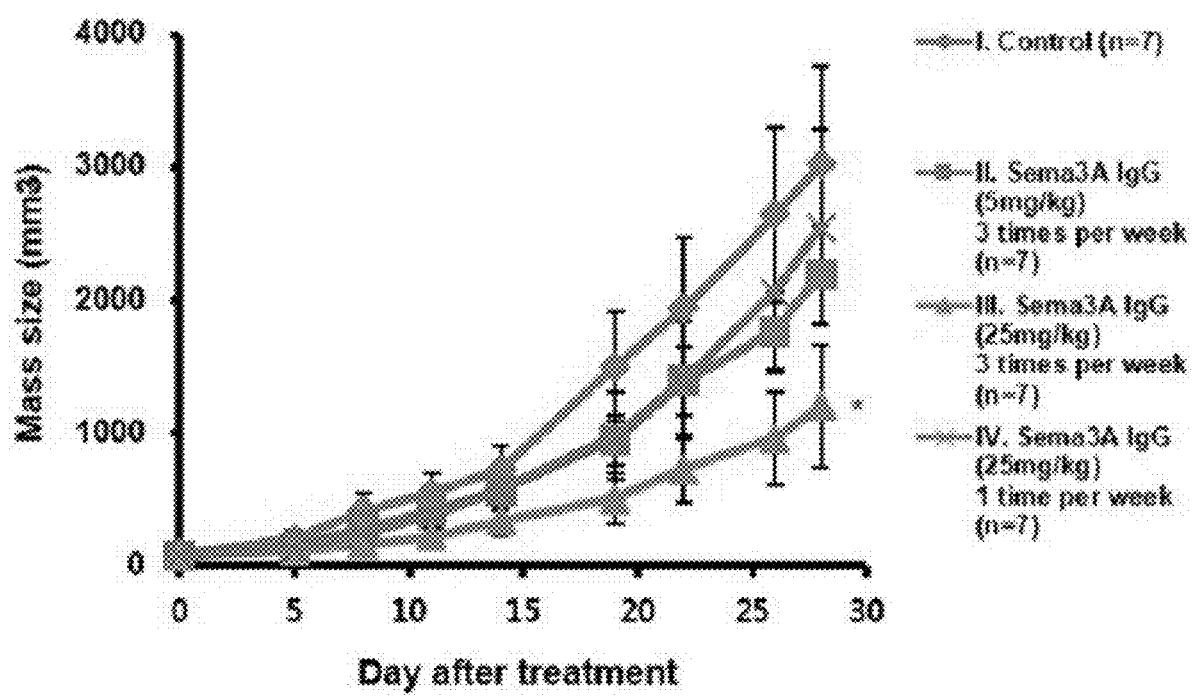
FIG. 24 shows the results confirming reductions in tumor size by anti-Sema3A IgG in animal models.
Figure 25:
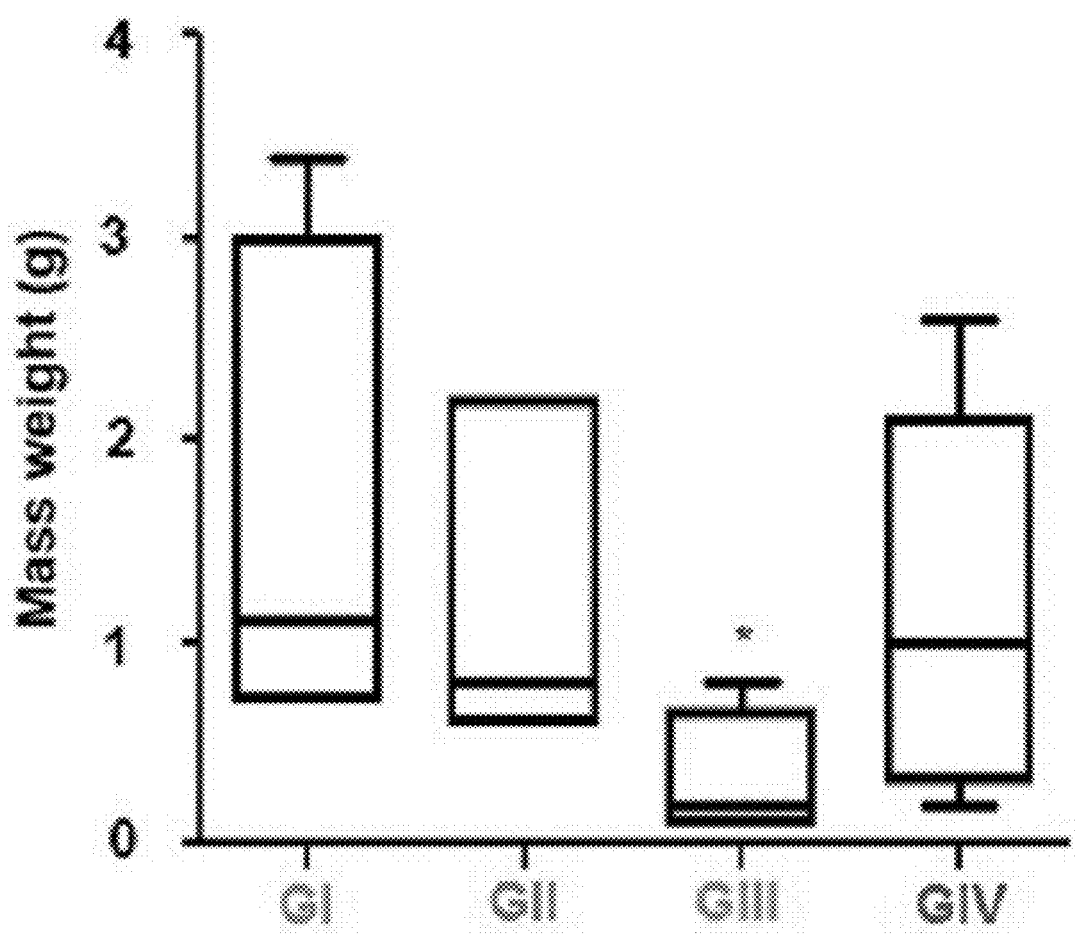
FIG. 25 shows the measurement results on tumor weight changes by anti-Sema3A IgG in animal models.

As the results of confirmation of the sizes of the tumor after injecting with 5 mg/kg and 25 mg/kg of anti-Sema3A F11 (i.v.) for 3 weeks, it was confirmed that the tumor size was reduced to 60% in the group injected with 25 mg/kg (3 times/week) as compared to the control (FIG. 24). Also, the changes of the tumor weight of individual groups were similarly calculated (FIG. 25).

Figure 26:
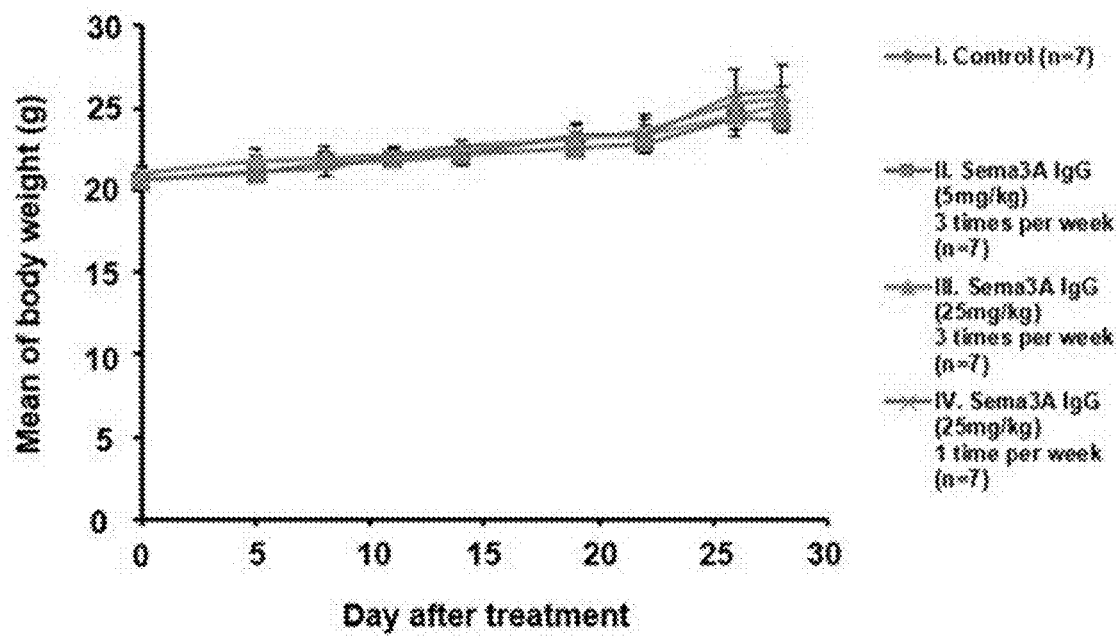
FIG. 26 shows the measurement results on body weight changes according to the administration of anti-Sema3A IgG in animal models.

Specific changes of the body weight by anti-Sema3A antibody injected were not confirmed (FIG. 26). Immunofluorescence was performed in control group and Group 3 tissues (F11 25 mg/kg, 3 times/week) which exhibited the highest efficacy, and it was confirmed that Sema3A and p-ERK were significantly reduced in the tissues of the groups treated with anti-Sema3A.

Figure 27:
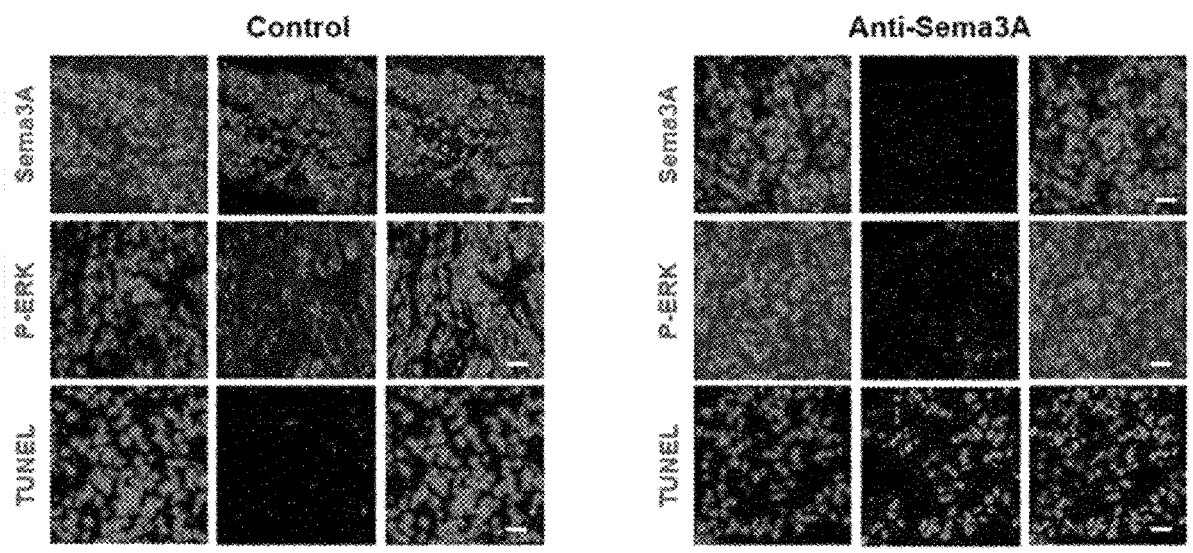
FIG. 27 shows the results confirming apoptotic effects by subjecting immunofluorescence staining after administration of anti-Sema3A IgG in animal models.

Apoptosis effects were also observed due to an increase of TUNEL positive cells as compared to the control (FIG. 27). Many publications have reported that Sema3A is involved in TAM infiltration (Casazza A, et al. Cancer cell. 2013; 24(6):695-709/Hu ZQ, et al. Oncotarget. 2016).

Figure 28:
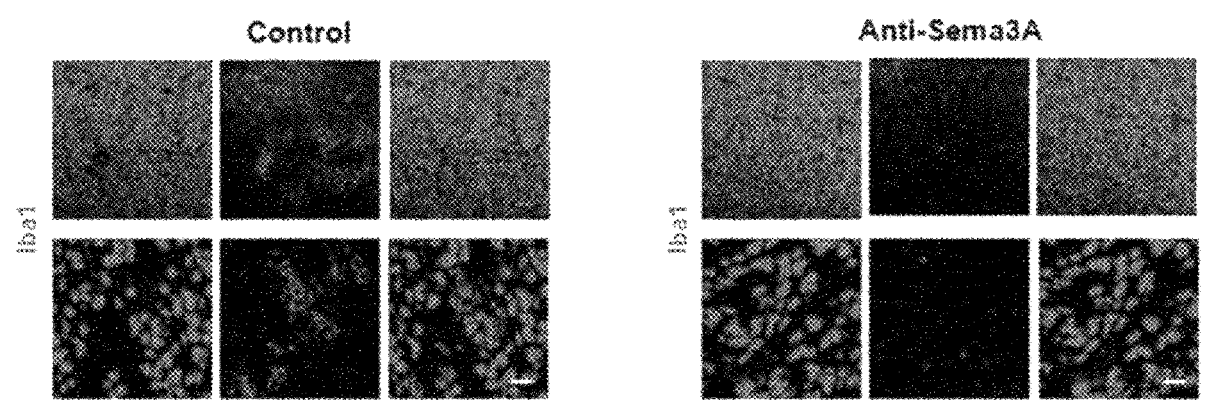
FIG. 28 shows the results confirming TAM distribution after administration of anti-Sema3A IgG in animal models.

Thus, to confirm this, the reduction of TAM distribution by Sema3A antibody was confirmed through staining Ibal which is a macrophage marker (FIG. 28).

This application contains references to amino acid sequences and/or nucleic acid sequences which have been submitted herewith as the sequence listing text file. The aforementioned sequence listing is hereby incorporated by reference in its entirety pursuant to 37 C.F.R. § 1.52(e).

What is claimed is:

1. An antibody or antigen binding fragment thereof that binds to human Semaphorin 3A (Sema3A) comprising:
   (a) a heavy chain variable region comprising the following heavy chain CDR amino acid sequences:
   CDRH1 consisting of the amino acid sequence of SEQ ID NO: 13,
   CDRH2 consisting of the amino acid sequence of SEQ ID NO: 14, and
   CDRH3 consisting of the amino acid sequence of SEQ ID NO: 15; and
   (b) a light chain variable region comprising the following light chain CDR amino acid sequences:
   CDRL1 consisting of the amino acid sequence of SEQ ID NO: 16,
   CDRL2 consisting of the amino acid sequence of SEQ ID NO: 17, and CDRL3 consisting of the amino acid sequence of SEQ ID NO: 18.

2. The antibody or antigen binding fragment thereof according to claim 1, wherein the heavy chain variable region comprises the amino acid sequence of SEQ ID NO: 23.

3. The antibody or antigen binding fragment thereof according to claim 1, wherein the light chain variable region comprises the amino acid sequence of SEQ ID NO: 24.

4. A composition comprising:
  (a) the antibody or antigen binding fragment thereof that binds to human Sema3A of claim 1; and
  (b) a pharmaceutically acceptable carrier.

5. A method for treating a cancer associated with Sema3A overexpression in a subject, the method comprising administering the composition of claim 4 to a subject.

6. The method according to claim 5, wherein the cancer is breast cancer, colon cancer, lung cancer, stomach cancer, liver cancer, blood cancer, bone cancer, pancreatic cancer, skin cancer, brain cancer, cervical cancer, nasopharyngeal cancer, laryngeal cancer, colon cancer, ovarian cancer, rectal cancer, colorectal cancer, vaginal cancer, small intestine cancer, endocrine cancer, thyroid cancer, parathyroid cancer, ureter cancer, urinary tract cancer, prostate cancer, bronchial cancer, bladder cancer, kidney cancer or marrow cancer.

* * * * *